United States Patent
Shimizu et al.

(10) Patent No.: US 11,407,703 B2
(45) Date of Patent: Aug. 9, 2022

(54) METHOD FOR CONVERTING HYDROXYL GROUP OF ALCOHOL

(71) Applicant: Takasago International Corporation, Tokyo (JP)

(72) Inventors: Hideo Shimizu, Kanagawa (JP); Kiyoto Hori, Kanagawa (JP); Hironori Maeda, Kanagawa (JP)

(73) Assignee: Takasago International Corporation, Tokyo (JP)

(*) Notice: Subject to any disclaimer, the term of this patent is extended or adjusted under 35 U.S.C. 154(b) by 6 days.

(21) Appl. No.: 17/051,261

(22) PCT Filed: May 8, 2019

(86) PCT No.: PCT/JP2019/018447
§ 371 (c)(1),
(2) Date: Oct. 28, 2020

(87) PCT Pub. No.: WO2019/216355
PCT Pub. Date: Nov. 14, 2019

(65) Prior Publication Data
US 2021/0047254 A1 Feb. 18, 2021

(30) Foreign Application Priority Data
May 9, 2018 (JP) .............................. JP2018-090639

(51) Int. Cl.
| | | |
|---|---|---|
| C07C 45/71 | (2006.01) | |
| B01J 31/00 | (2006.01) | |
| B01J 31/22 | (2006.01) | |
| C07C 49/12 | (2006.01) | |
| C07C 49/17 | (2006.01) | |
| C07C 49/203 | (2006.01) | |
| C07C 49/784 | (2006.01) | |

(52) U.S. Cl.
CPC .............. *C07C 45/71* (2013.01); *B01J 31/22* (2013.01); *C07C 49/12* (2013.01); *C07C 49/17* (2013.01); *C07C 49/203* (2013.01); *C07C 49/784* (2013.01)

(58) Field of Classification Search
CPC .......... C07C 45/71; C07C 49/12; B01J 31/22
See application file for complete search history.

(56) References Cited

FOREIGN PATENT DOCUMENTS

| CN | 101693726 A | 4/2010 |
|---|---|---|
| GB | 1 241 103 | 7/1971 |
| JP | 47-038413 B1 | 9/1972 |
| JP | 2009-137876 A | 6/2009 |
| JP | 2012-229189 A | 11/2012 |

OTHER PUBLICATIONS

M'hamedi et al. Bright green PhOLEDS using cyclometalated diiridium (III) complexes with bridging oxamidato ligands as phosphorescent dopants. Journal of Materials Chemistry C, vol. 5, 6777-6789. (Year: 2017).*
Zhang et al. [2+2] Photodimerization in the Solid State Aided by Molecular Templates of Rectangular Macrocycles Bearing Oxamidato Ligands. Organometallics, vol. 29, 2842-2849. (Year: 2010).*
Nixon et al,. "Benzyl Alcohol as an Alkylating Agent Using the Ruthenium-Catalyzed Borrowing Hydrogen Strategy (4,4-Dimethyl-3-oxo-2-benzylpentaenitrile)," Org. Synth., 2009, 86:28-35.
Series of Experimental Chemistry, vol. 21, The Chemical Society of Japan, Maruzen, 2004, 206-227 and 275-287, with brief English explanation.
Trost, B.M., Ed., Science of Synthesis, 2001, pp. 617-744 and 931-972.
Turlington et al., "Oxygen Atom Transfer to a Half-Sandwich Iridium Complex: Clean Oxidation Yielding a Molecular Product," Journal of the American Chemical Society, Feb. 26, 2014, 136:3981-3994.
Williams, Jonathan M.J., "OH Activation for Nucleophilic Substitution," Sustainable Catalysis: Challenges and Practices for the Pharmaceutical and Fine Chemical Industries, Peter J. Dunn, Ed., 2013, Chapter 7, 121-137.
Yamada et al., "A Solid-Phase Self-Organized Catalyst of Nanopalladium with Main-Chain Viologen Polymers: alpha-Alkylation of Ketones with Primary Alcohols," Organic Letters, 2006, 8(7): 1375-1378.
Yamaguchi et al., Ligand Platforms in Homogenous Catalytic Reactions with Metals, Practice and Applications for Green Organic Transformations, 2015, Chapter 2 (27-53); Chapter 4 (87-106); Chapter 7 (159-182); and Chapter 10 (278-333).

* cited by examiner

*Primary Examiner* — Sikarl A Witherspoon
(74) *Attorney, Agent, or Firm* — Foley & Lardner LLP

(57) ABSTRACT

The present invention relates to: a method for converting a hydroxyl group of an alcohol; and a catalyst which makes the method possible. A method for converting a hydroxyl group of an alcohol according to the present invention is characterized by producing a compound represented by $CH(R^1)(R^2)Nu$ (wherein $R^1$, $R^2$ and Nu are as defined below) by reacting an alcohol represented by $CH(R^1)(R^2)$ OH (wherein each of $R^1$ and $R^2$ represents a hydrogen atom, an optionally substituted alkyl group, or the like) and a compound having an active proton, which is represented by H-Nu (wherein Nu represents a group represented by $-CHX^1\text{-}EWG^1$ or $-NR^3R^4$; $X^1$ represents a hydrogen atom or the like; $EWG^1$ represents an electron-withdrawing group; and each of $R^3$ and $R^4$ represents a hydrogen atom, an optionally substituted alkyl group, or the like), with each other in the presence of a complex of a group 7-11 metal of the periodic table and at least one solid base that is selected from the group consisting of layered double hydroxides, composite oxides and calcium hydroxide.

19 Claims, No Drawings

METHOD FOR CONVERTING HYDROXYL GROUP OF ALCOHOL

CROSS-REFERENCE TO RELATED APPLICATIONS

This application is the U.S. National Stage of PCT/JP2019/018447, filed May 8, 2019, which claims priority to JP 2018-090639, filed May 9, 2018.

TECHNICAL FIELD

The present invention relates to a method for converting a hydroxyl group of an alcohol, and a catalyst allowing efficient conversion of such a hydroxyl group.

BACKGROUND ART

Ketones, amines and other compounds having active protons may be elongated by alkylation, and this reaction is important in the production of various valuable substances such as pharmaceutical compounds, flavors and fragrances. For this purpose, alkyl halides are commonly used as alkylating agents, but alkyl halides are expensive and have some problems because they are likely to cause excessive reaction and produce a stoichiometric amount of salts as by-products, etc. For this reason, recent attempts have been made to catalytically convert a hydroxyl group of a relatively inexpensive alcohol, i.e., to use an alcohol as an alkylating agent (Non-patent Literatures 1 and 6).

For example, as known from Non-patent Literature 2, there is a technique using a catalyst composed of carbonyldihydridotris(triphenylphosphine)ruthenium(II) ([RuH$_2$(CO)(PPh$_3$)$_3$]), 4,5-bis(diphenylphosphino)-9,9-dimethylxanthene (Xantphos) and piperidinium acetate to catalyze the conversion of benzyl alcohol and 4,4-dimethyl-3-oxopentanenitrile into 4,4-dimethyl-3-oxo-2-benzylpentanenitrile.

In addition, Patent Literature 1 discloses a method in which an alkylene glycol and a compound containing a carbonyl group are reacted using a catalyst composed of chloro(1,5-cyclooctadiene)iridium(I) dimer ([IrCl(cod)]$_2$), triphenylphosphine and potassium hydroxide to thereby obtain a compound having carbonyl groups at the both ends of the alkylene group.

CITATION LIST

Patent Literature

Patent Literature t 1: JP 2009-137876 A

Non-Patent Literature

Non-patent Literature 1: Sustainable Catalysis: Challenges and Practices for the Pharmaceutical and Fine Chemical Industries, 1st Ed. John Wiley & Sons, 2013, pp 121-137

Non-patent Literature 2: Organic Synthesis 2009, 86, 28.

Non-patent Literature 3: Ligand Platforms in Homogeneous Catalytic Reaction with Metals, Yamaguchi, R., Fujita, K. Eds: Wiley, 2014.

Non-patent Literature 4: Science of Synthesis, Trost, B. M. Ed: Thieme, 2001.

Non-patent Literature 5: Encyclopedia of Experimental Chemistry, volume 21, edited by The Chemical Society of Japan: MARUZEN Co., Ltd., Japan, 2004

Non-patent Literature 6: Organic Letters 2006, Vol. 8, No. 7, 1375-1378

SUMMARY OF INVENTION

Technical Problem

However, in general, conventional techniques were substrate-specific and their catalytic activity was inadequate for practical use. Under these circumstances, there has been a demand for the development of a method for converting a hydroxyl group of an alcohol, which achieves higher catalytic activity, and a catalyst which makes this method possible.

Solution to Problem

The inventors of the present invention have found that a combination of a metal complex of Groups 7 to 11 in the periodic table and a layered double hydroxide has good catalytic activity in the conversion of a hydroxyl group of an alcohol. Moreover, as a result of further studies, the inventors of the present invention have found that a combination of a metal complex of Groups 7 to 11 in the periodic table and a solid base selected from the group consisting of a composite oxide and calcium hydroxide has good catalytic activity in the conversion of a hydroxyl group of an alcohol. These findings led to the completion of the present invention.

Namely, the present invention relates to a method for converting a hydroxyl group of an alcohol and a metal complex which makes this method possible, as shown below.

[1] A method for converting a hydroxyl group of an alcohol, comprising reacting:

in the presence of a metal complex of Groups 7 to 11 in the periodic table and at least one solid base selected from the group consisting of a layered double hydroxide, a composite oxide and calcium hydroxide;

an alcohol represented by the following general formula (1):

[Formula 1]

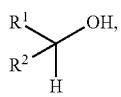

(1)

wherein:

R$^1$ and R$^2$ are each independently a hydrogen atom, an optionally substituted alkyl group, an optionally substituted aryl group, an optionally substituted heterocyclyl group or an optionally substituted aralkyl group, where at least one of R$^1$ and R$^2$ may have a hydroxyl group as a substituent, and/or R$^1$ and R$^2$ may be joined together to form a ring; with a compound having an active proton represented by the following general formula (2):

[Formula 2]

H-Nu (2), wherein:

Nu is a group represented by —CHX$^1$-EWG$^1$ or —NR$^3$R$^4$, where X$^1$ is a hydrogen atom or a substituent, EWG$^1$ is an electron-withdrawing group, and R$^3$ and R$^4$ are each independently a hydrogen atom, an optionally substituted alkyl group, an optionally substituted aryl group, an optionally substituted heterocyclyl group or an optionally substituted aralkyl group, where R$^3$ and R$^4$ may be joined together to form a ring; or when R$^1$ in general formula (1) is attached to X$^1$ or R$^3$ in Nu in general formula (2) such that the alcohol and the compound having an active proton form a single molecule, the reaction occurs within the molecule;

to produce a compound represented by the following general formula (3):

[Formula 3]

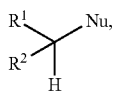

(3)

wherein:

R$^1$, R$^2$ and Nu are as defined above, where R$^1$ and X$^1$ or R$^3$ in Nu may be joined together to form a ring.

[2] The method for converting a hydroxyl group of [1] above, wherein the solid base is a layered double hydroxide.

[3] The method for converting a hydroxyl group of [2] above, wherein the layered double hydroxide is a hydrotalcite-type compound.

[4] The method for converting a hydroxyl group of any one of [1] to [3] above, wherein the solid base is a composite oxide comprising two or more metal elements, at least one of which is a metal element selected from the group consisting of aluminum, magnesium and calcium.

[5] The method for converting a hydroxyl group of any one of [1] to [4] above, wherein the compound having an active proton represented by general formula (2) is a carbonyl compound represented by the following general formula (2-1):

[Formula 4]

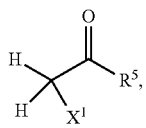

(2-1)

wherein:

X$^1$ is as defined above, and

R$^5$ is a hydrogen atom, an optionally substituted alkyl group, an optionally substituted alkenyl group, an optionally substituted alkynyl group, an optionally substituted aryl group, an optionally substituted heterocyclyl group, an optionally substituted aralkyl group, an optionally substituted alkoxy group, an optionally substituted aryloxy group, an optionally substituted amino group or an optionally substituted carbonyl group, wherein X$^1$ and R$^5$ may be joined together to form a ring.

In one embodiment of the present invention, the compound having an active proton represented by general formula (2) may be a nitrile represented by the following general formula (2-2):

[Formula 5]

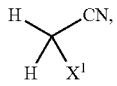

(2-2)

wherein:

X$^1$ is as defined above.

Moreover, in another embodiment of the present invention, the compound having an active proton represented by general formula (2) may be an amine represented by the following general formula (2-3):

[Formula 6]

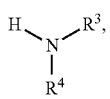

(2-3)

wherein:

R$^3$ and R$^4$ are as defined above.

[6] The method for converting a hydroxyl group of any one of [1] to [5] above, wherein the metal complex of Groups 7 to 11 in the periodic table is an iridium complex or a ruthenium complex.

[7] The method for converting a hydroxyl group of [6] above, wherein the iridium complex is:

a compound represented by the following general formula (4-1) or a dimer thereof:

[Formula 7]

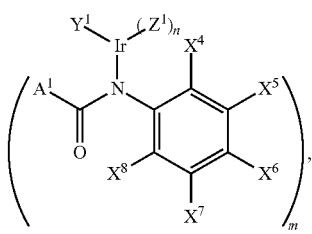

(4-1)

wherein:

Y$^1$ is an optionally substituted cyclopentadienyl group or an optionally substituted indenyl group, Z$^1$ is a hydrido or anionic group, A$^1$ is an optionally substituted aryl group, an optionally substituted heterocyclyl group or an optionally substituted carbonyl group, wherein A may partially coordinate to the iridium atom, X$^4$, X$^5$, X$^6$, X$^7$ and X$^8$ are each independently a hydrogen atom or a substituent, where X$^4$ and X$^5$, X$^5$ and X$^6$, X$^6$ and X$^7$ as well as X$^7$ and X$^8$ may each be joined together to form a ring, and/or Y$^1$ and A$^1$ as well as Y$^1$ and X$^4$ may each be joined together to form a ring, and m is 1 or 2, and n is 1 or 0, provided that n is 1 when m is 1, and n is 0 when m is 2; or a compound represented by the following general formula (4-2):

[Formula 8]

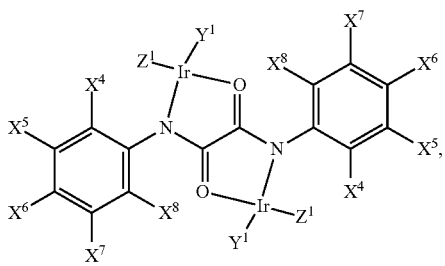

(4-2)

wherein:
$Y^1$, $Z^1$, $X^4$, $X^5$, $X^6$, $X^7$ and $X^8$ are as defined above.

[8] The method for converting a hydroxyl group according to [6] or [7] above, wherein the iridium complex is formed within the reaction system by mixing an iridium compound represented by the following general formula (5-1) or a dimer thereof:

$$[Y^1 IrZ^1{}_2] \quad (5\text{-}1),$$

wherein:
$Y^1$ is an optionally substituted cyclopentadienyl group or an optionally substituted indenyl group, and
$Z^1$ is a hydrido or anionic group; with
an anilide represented by the following general formula (6-1):

[Formula 9]

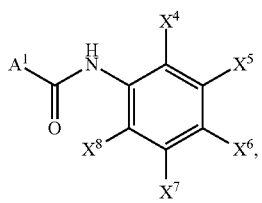

(6-1)

wherein:
$A^1$ is an optionally substituted aryl group, an optionally substituted heterocyclyl group or an optionally substituted carbonyl group, and
$X^4$, $X^5$, $X^6$, $X^7$ and $X^8$ are each independently a hydrogen atom or a substituent,
where $X^4$ and $X^5$, $X^5$ and $X^6$, $X^6$ and $X^7$ as well as $X^7$ and $X^8$ may each be joined together to form a ring; or with
an anilide represented by the following general formula (6-2):

[Formula 10]

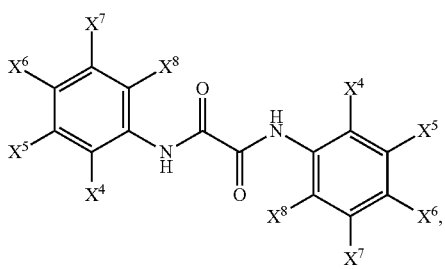

(6-2)

wherein:
$X^4$, $X^5$, $X^6$, $X^7$ and $X^8$ are as defined above.

[9] The method for converting a hydroxyl group of [6] above, wherein the ruthenium complex is:
a compound represented by the following general formula (4-3) or a dimer thereof:

[Formula 11]

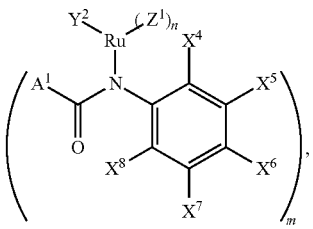

(4-3)

wherein:
$Y^2$ is an optionally substituted arene,
$Z^1$ is a hydrido or anionic group,
$A^1$ is an optionally substituted aryl group, an optionally substituted heterocyclyl group or an optionally substituted carbonyl group, where $A^1$ may partially coordinate to the ruthenium atom,
$X^4$, $X^5$, $X^6$, $X^7$ and $X^8$ are each independently a hydrogen atom or a substituent,
where $X^4$ and $X^5$, $X^5$ and $X^6$, $X^6$ and $X^7$ as well as $X^7$ and $X^8$ may each be joined together to form a ring, and/or $Y^2$ and $A^1$ as well as $Y^1$ and $X^4$ may each be joined together to form a ring, and
m is 1 or 2, and n is 1 or 0, provided that n is 1 when m is 1, and n is 0 when m is 2; or
a compound represented by the following general formula (4-4):

[Formula 12]

(4-4)

wherein:
$Y^2$, $Z^1$, $X^4$, $X^5$, $X^6$, $X^7$ and $X^8$ are as defined above.

[10] The method for converting a hydroxyl group of [9] above, wherein the ruthenium complex is formed within the reaction system by mixing a ruthenium compound represented by the following general formula (5-3) or a dimer thereof:

$$[Y^2 RuZ^1{}_2] \quad (5\text{-}3),$$

wherein:

$Y^2$ is an optionally substituted arene, and $Z^1$ is a hydrido or anionic group; with an anilide represented by the following general formula (6-1):

[Formula 13]

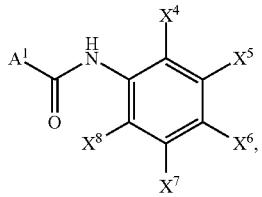
(6-1)

wherein:

$A^1$ is an optionally substituted aryl group, an optionally substituted heterocyclyl group or an optionally substituted carbonyl group, $X^4$, $X^5$, $X^6$, $X^7$ and $X^8$ are each independently a hydrogen atom or a substituent, where $X^4$ and $X^5$, $X^5$ and $X^6$, $X^6$ and $X^7$ as well as $X^7$ and $X^8$ may each be joined together to form a ring; or with an anilide represented by the following general formula (6-2):

[Formula 14]

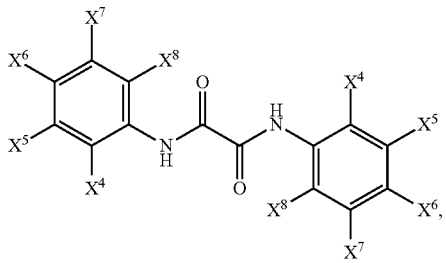
(6-2)

wherein:

$X^4$, $X^5$, $X^6$, $X^7$ and $X^8$ are as defined above.

[11] The method for converting a hydroxyl group of any one of [5] to [10] above, wherein the carbonyl compound represented by general formula (2-1) is acetone.

It should be noted that in one embodiment of the present invention, the alcohol represented by general formula (1) is preferably a diol represented by the following general formula (1-1):

[Formula 15]

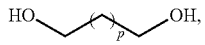
(1-1)

wherein:

p is an integer of 0 to 48.

Moreover, in one embodiment of the present invention, the alcohol represented by general formula (1) is preferably a diol represented by the following formula (1-1a):

[Formula 16]

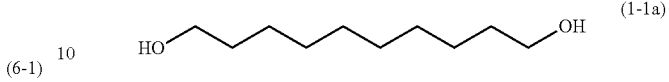
(1-1a)

and the compound represented by general formula (3) is preferably a diketone represented by the following formula (3-2a):

[Formula 17]

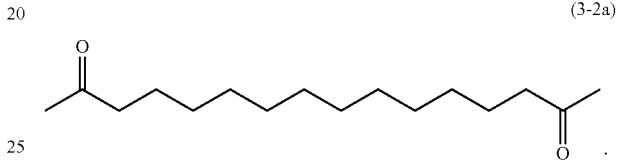
(3-2a)

[12] An iridium complex selected from the group consisting of:

a compound represented by the following general formula (4-1a) or a dimer thereof:

[Formula 18]

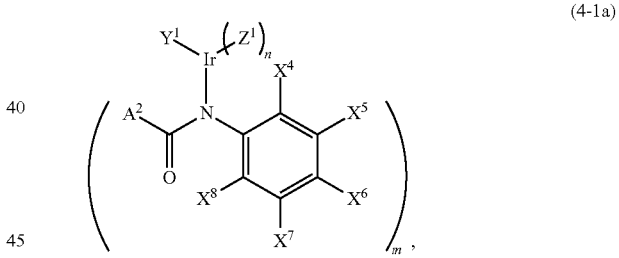
(4-1a)

wherein:

$Y^1$ is an optionally substituted cyclopentadienyl group or an optionally substituted indenyl group, $Z^1$ is a hydrido or anionic group, $A^2$ is an optionally substituted aryl group or an optionally substituted carbonyl group, where $A^2$ may partially coordinate to the iridium atom, $X^4$, $X^5$, $X^6$, $X^7$ and $X^8$ are each independently a hydrogen atom or a substituent, where $X^4$ and $X^5$, $X^5$ and $X^6$, $X^6$ and $X^7$ as well as $X^7$ and $X^8$ may each be joined together to form a ring, and/or $Y^1$ and $A^2$ as well as $Y^1$ and $X^4$ may each be joined together to form a ring, and m is 1 or 2, and n is 1 or 0, provided that n is 1 when m is 1, and n is 0 when m is 2; and a compound represented by the following general formula (4-2):

[Formula 19]

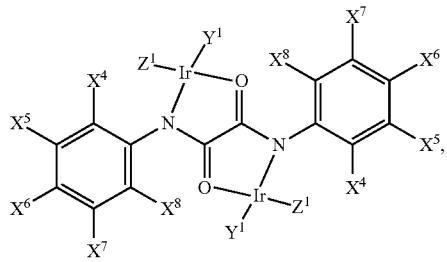

(4-2)

wherein:

$Y^1$, Z, $X^4$, $X^5$, $X^6$, $X^7$ and $X^8$ are as defined above, except for the case where $Y^1$ is pentamethylcyclopentadienyl, $Z^1$ is a chlorine atom, $X^4$, $X^5$, $X^7$ and $X^8$ are each a hydrogen atom, and $X^6$ is a hydrogen atom or a methyl group.

[13] The iridium complex of [12] above, which is a catalyst for use in the reaction of converting a hydroxyl group of an alcohol.

[14] A ruthenium complex selected from the group consisting of:

a compound represented by the following general formula (4-3) or a dimer thereof:

[Formula 20]

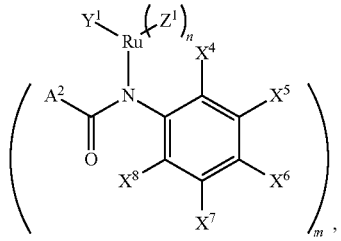

(4-3)

wherein:

$Y^2$ is an optionally substituted arene, $Z^1$ is a hydrido or anionic group, $A^1$ is an optionally substituted aryl group, an optionally substituted heterocyclyl group or an optionally substituted carbonyl group, where $A^1$ may partially coordinate to the ruthenium atom, $X^4$, $X^5$, $X^6$, $X^7$ and $X^8$ are each independently a hydrogen atom or a substituent, where $X^4$ and $X^5$, $X^5$ and $X^6$, $X^6$ and $X^7$ as well as $X^7$ and $X^8$ may each be joined together to form a ring, and/or $Y^1$ and $A^1$ as well as $Y^1$ and $X^4$ may each be joined together to form a ring, and m is 1 or 2, and n is 1 or 0, provided that n is 1 when m is 1, and n is 0 when m is 2; or a compound represented by the following general formula (4-4):

[Formula 21]

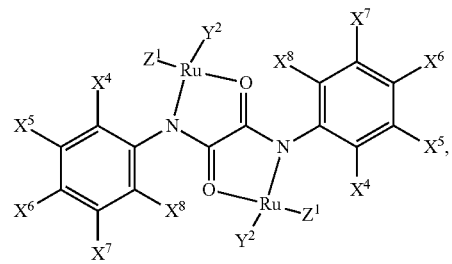

(4-4)

wherein:

$Y^2$, $Z^1$, $X^4$, $X^5$, $X^6$, $X^7$ and $X^8$ are as defined above.

[15] The ruthenium complex of [14] above, which is a catalyst for use in the reaction of converting a hydroxyl group of an alcohol.

Advantageous Effects of Invention

The present invention enables the provision of a novel method for converting a hydroxyl group of an alcohol, and a metal complex which makes this method possible. According to a preferred embodiment of the present invention, high catalytic activity can be achieved.

DESCRIPTION OF EMBODIMENTS

A detailed explanation will be given below of the method of the present invention for converting a hydroxyl group of an alcohol and the metal complex of the present invention.

[1] Method for converting a hydroxyl group of an alcohol

A method for converting a hydroxyl group according to the present invention is characterized in that the method comprising reacting:

in the presence of a metal complex of Groups 7 to 11 in the periodic table and at least one solid base selected from the group consisting of a layered double hydroxide, a composite oxide and calcium hydroxide;

an alcohol represented by the following general formula (1):

[Formula 22]

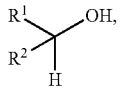

(1)

wherein:

$R^1$ and $R^2$ are each independently a hydrogen atom, an optionally substituted alkyl group, an optionally substituted aryl group, an optionally substituted heterocyclyl group or an optionally substituted aralkyl group, where at least one of $R^1$ and $R^2$ may have a hydroxyl group as a substituent, and/or $R^1$ and $R^2$ may be joined together to form a ring; with a compound having an active proton represented by the following general formula (2):

[Formula 23]

H-Nu (2), wherein:

Nu is a group represented by —CHX$^1$-EWG$^1$ or —NR$^3$R$^4$, where X$^1$ is a hydrogen atom or a substituent, EWG$^1$ is an electron-withdrawing group, and R$^3$ and R$^4$ are each independently a hydrogen atom, an optionally substituted alkyl group, an optionally substituted aryl group, an optionally substituted heterocyclyl group or an optionally substituted aralkyl group, where R$^3$ and R$^4$ may be joined together to form a ring; or when R$^1$ in general formula (1) is attached to X$^1$ or R$^3$ in Nu in general formula (2) such that the alcohol and the compound having an active proton form a single molecule, the reaction occurs within the molecule;

to produce a compound represented by the following general formula (3):

[Formula 24]

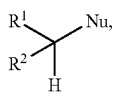

(3)

wherein:

R$^1$, R$^2$ and Nu are as defined above, where R$^1$ and X$^1$ or R$^3$ in Nu may be joined together to form a ring.

According to the present invention, in the presence of a metal complex of Groups 7 to 11 in the periodic table and at least one solid base selected from the group consisting of a layered double hydroxide, a composite oxide and calcium hydroxide, an alcohol is reacted with a compound having an active proton, or when these compounds form a single molecule, the reaction occurs within the molecule to directly convert a hydroxyl group of the alcohol, whereby the compound having an active proton can be alkylated. The method of the present invention for converting a hydroxyl group will be described in more detail below.

[Metal Complex of Groups 7 to 11 in the Periodic Table]

In the present invention, a metal complex comprising a metal element of Groups 7 to 11 in the periodic table is used as a catalyst. Such a metal element of Groups 7 to 11 in the periodic table comprises one or more members selected from manganese, technetium, rhenium, iron, ruthenium, osmium, cobalt, rhodium, iridium, nickel, palladium, platinum, copper, silver and gold. The metal complex of Groups 7 to 11 in the periodic table to be used in the present invention is not limited in any way, as long as it is a complex comprising any of these metal elements. Examples include metal complexes described in Ligand Platforms in Homogeneous Catalytic Reaction with Metals, Yamaguchi, R., Fujita, K. Eds: Wiley, 2014 (Non-patent Literature 3) and Science of Synthesis, Trost, B. M. Ed: Thieme, 2001 (Non-patent Literature 4). Among them, a ruthenium complex and an iridium complex are preferred, with an iridium complex being particularly preferred.

[Iridium Complex]

Examples of an iridium complex for use in the present invention include the following complexes: tris(acetylacetonato)iridium(III) ([Ir(acac)$_3$]), chloro(1,5-cyclooctadiene) iridium(I) dimer ([IrCl(cod)]$_2$), methoxy(1,5-cyclooctadiene)iridium(I) dimer ([Ir(OMe)(cod)]$_2$), chlorobis (cyclooctene)iridium(I) dimer ([IrCl(coe)$_2$]$_2$), dichloro (pentamethylcyclopentadienyl)iridium(III) dimer ([Cp*IrCl$_2$]$_2$), dibromo-(pentamethylcyclopentadienyl) iridium(III) dimer ([Cp*IrBr$_2$]$_2$), diiodo(pentamethyl-cyclopentadienyl)iridium(III) dimer ([Cp*IrI$_2$]$_2$), bis(1,5-cyclooctadiene)iridium(I) tetrafluoroborate ([Ir(cod)$_2$]BF$_4$), tris(dipivaloylmethanato)iridium(III) ([Ir(dpm)$_3$]), (indenyl) (cyclooctadiene)iridium(I) ((cod)Ir(indenyl)), etc., wherein Cp* represents a 1,2,3,4,5-pentamethylcyclopentadienyl group.

Other examples of an iridium complex include those having a ligand L.

Examples of such a ligand L include a phosphine ligand L$^1$, a nitrogen-containing ligand L$^2$ and a carbene ligand L$^3$, etc.

A phosphine ligand L$^1$ may be exemplified by a monodentate phosphine ligand and a bidentate phosphine ligand.

Examples of a monodentate phosphine ligand include triphenylphosphine, tri(4-tolyl)phosphine, tri(3,5-xylyl) phosphine, tricyclohexylphosphine, tri(tert-butylphosphine), 2-diphenylphosphino-2'-methoxy-1,1'-binaphthyl (MOP), etc.

Examples of a bidentate phosphine ligand include 1,1'-bis(diphenyl-phosphino)ferrocene (DPPF), 1,1-bis(diphenylphosphino)methane (DPPM), 1,2-bis(diphenylphosphino)ethane (DPPE), 1,3-bis(diphenylphosphino)propane (DPPP), 1,4-bis(diphenylphosphino)butane (DPPE), 1,5-bis (diphenylphosphino)benzene, 2,2'-bis(diphenylphosphino)-1,1'-binaphthalene (BINAP), 5,5'-bis(diphenylphosphino)-4,4'-bi-1,3-benzodioxole (SEGPHOS), 5,5'-bis[bis(3,5-dimethylphenyl)phosphino]-4,4'-bi-1,3-benzodioxole (DM-SEGPHOS), 5,5'-bis[bis(3,5-bis(1,1-dimethylethyl)-4-methoxyphenyl)phosphino]-4,4'-bi-1,3-benzodioxole (DTBM-SEGPHOS), etc.

A nitrogen-containing ligand L$^2$ may be exemplified by a monodentate or bidentate nitrogen-containing ligand. Specific examples include a monodentate amine ligand, a bidentate amine ligand, a monodentate amide ligand or a bidentate amide ligand, etc.

Examples of a monodentate amine ligand include pyridine, 4-dimethylaminopyridine, ethylamine, diethylamine, triethylamine, tributylamine, quinuclidine, etc.

Examples of a bidentate amine ligand include 2-picolylamine, ethylenediamine (EDA), tetramethylethylenediamine, 1,2-diphenylethylenediamine (DPEN), N-(p-toluenesulfonyl)-1,2-diphenylethylenediamine (Ts-DPEN), N-(methanesulfonyl)-1,2-diphenylethylenediamine (Ts-DPEN), 1,1-bis(4-methoxyphenyl)-3-methylbutane-1,2-diamine (DAIPEN), etc.

Examples of a monodentate or bidentate amide ligand include formamide, acetamide, benzamide, acetoanilide, oxamide, N,N'-dialkyloxamides containing 4 to 20 carbon atoms (e.g., N,N'-dimethyloxamide, N,N'-diethyloxamide, N,N'-dibutyl-oxamide), or an anilide represented by the following general formula (6-1):

[Formula 25]

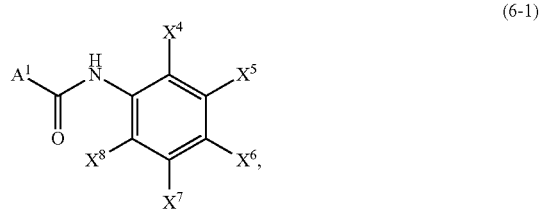

(6-1)

wherein:

A¹ is an optionally substituted aryl group, an optionally substituted heterocyclyl group or an optionally substituted carbonyl group, $X^4$, $X^5$, $X^6$, $X^7$ and $X^8$ are each independently a hydrogen atom or a substituent, where $X^4$ and $X^5$, $X^5$ and $X^6$, $X^6$ and $X^7$ as well as $X^7$ and $X^8$ may each be joined together to form a ring; or an anilide represented by the following general formula (6-2):

[Formula 26]

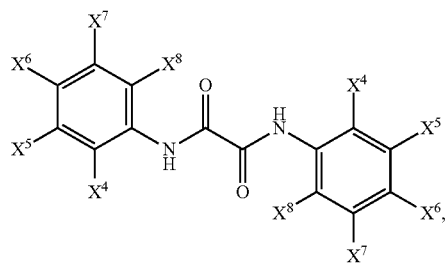

(6-2)

wherein:

$X^4$, $X^5$, $X^6$, $X^7$ and $X^8$ are each independently a hydrogen atom or a substituent, where $X^4$ and $X^5$, $X^5$ and $X^6$, $X^6$ and $X^7$ as well as $X^7$ and $X^8$ may each be joined together to form a ring.

It should be noted that these anilides represented by general formula (6-1) and general formula (6-2) are the same compounds as anilides represented by general formula (6-1) and general formula (6-2), respectively, which are used in the preparation of an iridium complex.

Examples of an anilide serving as a ligand include the following compounds, by way of example.

[Formula 27]

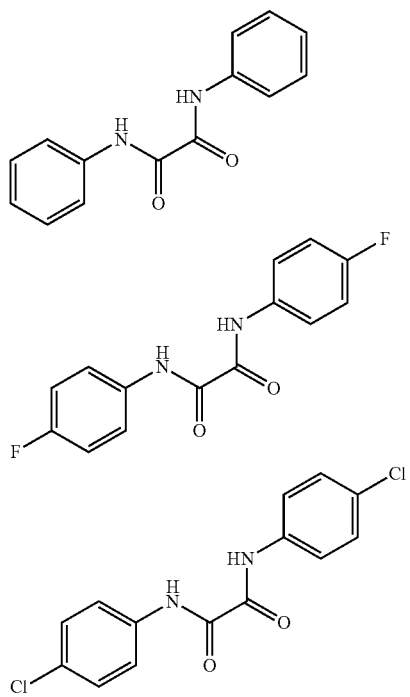

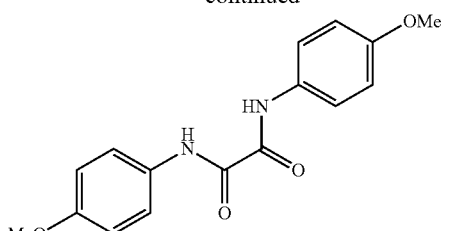

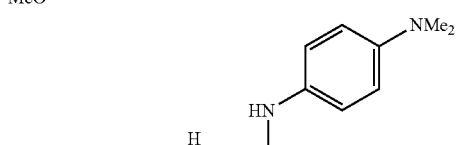

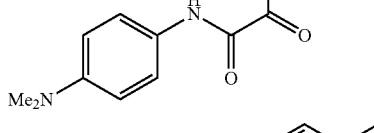

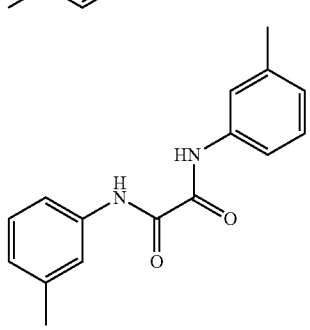

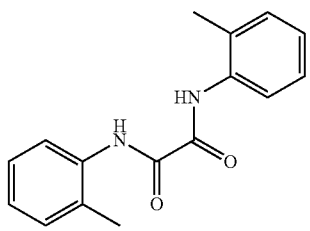

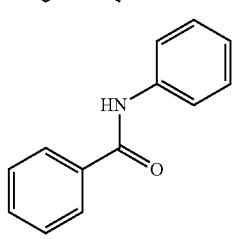

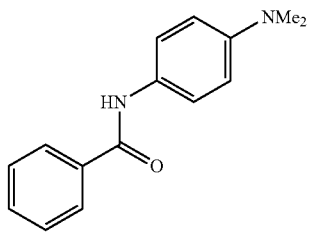

-continued
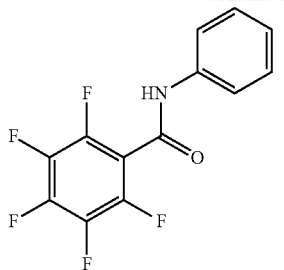
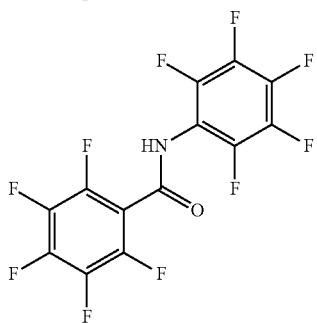
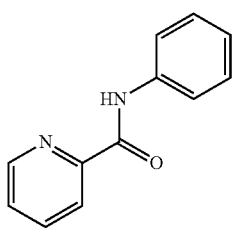
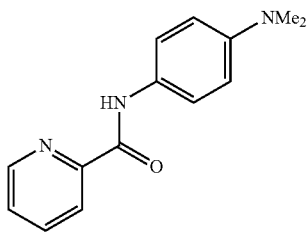
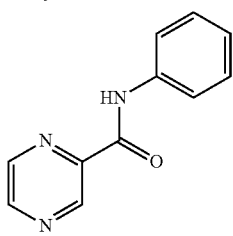
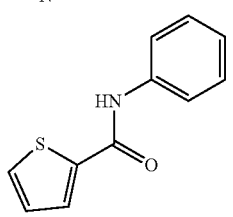
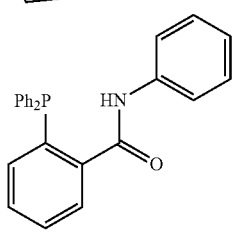
-continued
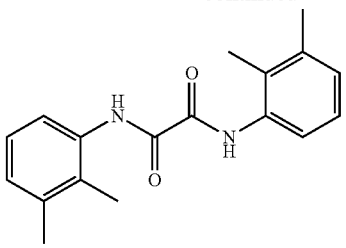
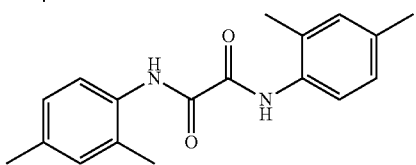
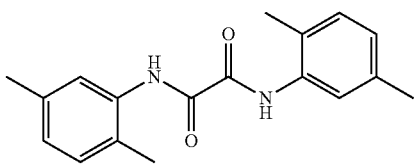
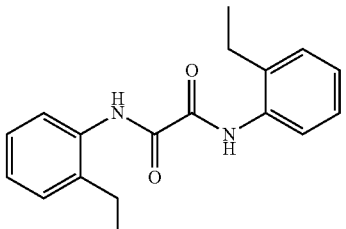
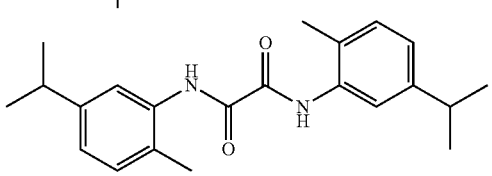
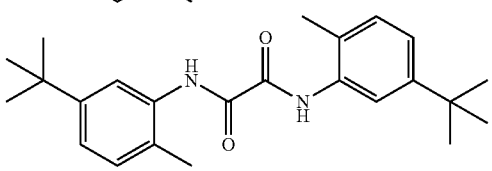
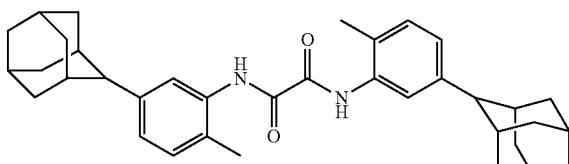
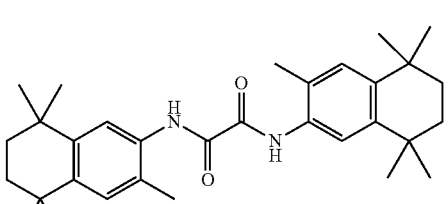
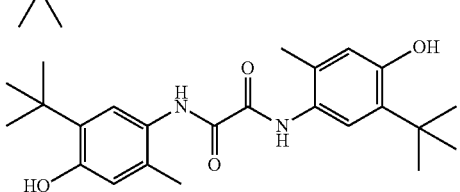

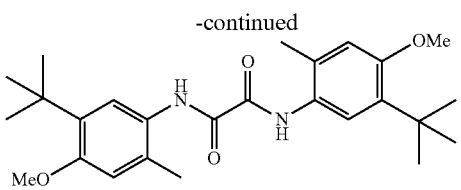

A carbene ligand $L^3$ may be exemplified by an N-heterocyclic carbene ligand. Specific examples include 1,3-dimethylimidazol-2-yliden, 1,3-diisopropylimidazol-2-yliden, 1,3-dibutylimidazol-2-yliden, 1,3-bis(2,4,6-trimethiylphenyl)imidazol-2-yliden, 1,3-dimethylbenzoimidazol-2-yliden, 1,3-dimethyldihydroimidazol-2-yliden, etc.

As a ligand L, a bidentate or tridentate compound may also be used which has multiple sites selected from phosphine, a nitrogen-containing site and a carbine site within the same molecule. Specific examples include 2-(diphenylphosphino)-ethylamine, bis[(2-diphenylphosphino)ethyl]amine, etc.

If these ligands L have chirality, they may be in racemic form, in meso form or in optically active form.

Specific examples of iridium complexes having a ligand L include the following compounds: $[IrL^1_b Cl]_2$, $[IrL^1_b Br]_2$, $[IrL^1_b I]_2$, $[Ir(cod)L^1_b]BF_4$, $[Ir(cod)L^1_b]ClO_4$, $[Ir(cod)L^1_b]PF_6$, $[Ir(cod)Lib]BPh_4$, $[Ir(cod)L^1_b]OTf$, $[Ir(nbd)L^1_b]BF_4$, $[Ir(nbd)L^1_b]ClO_4$, $[Ir(nbd)L^1_b]PF_6$, $[Ir(nbd)L^1_b]BPh_4$, $[Ir(nbd)L^1_b]OTf$, $Cp^*IrClL^2_c$, $Cp^*IrCl_2L^2_{0.5c}$, $Cp^*IrClL^2_{0.5c}$, $Cp^*IrL^2_c$, $(Cp^*IrCl)_2L^2_c$, $Cp^*IrCl_2L^3$, $Cp^*Ir(OTf)_2L^3$, etc.

In the above compounds, b=2 when $L^1$ is a monodentate phosphine ligand, b=1 when $L^1$ is a bidentate phosphine ligand, c=2 when $L^2$ is a monodentate nitrogen-containing ligand, and c=1 when $L^2$ is a bidentate nitrogen-containing ligand. Moreover, when $L^2$ is a nitrogen-containing compound, the nitrogen atom in $L^2$ may directly coordinate to the iridium atom, or alternatively, a proton on the nitrogen atom in $L^2$ may be eliminated to form a metal amide with iridium.

Moreover, a preferred iridium complex may be specifically exemplified by an iridium complex selected from the group consisting of:

a compound represented by the following general formula (4-1):

[Formula 28]

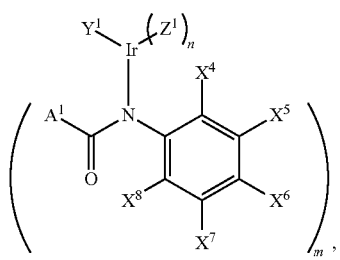

wherein:
$Y^1$ is an optionally substituted cyclopentadienyl group or an optionally substituted indenyl group,
$Z^1$ is a hydrido or anionic group,
$A^1$ is an optionally substituted aryl group, an optionally substituted heterocyclyl group or an optionally substituted carbonyl group, where $A^1$ may partially coordinate to the iridium atom, $X^4$, $X^5$, $X^6$, $X^7$ and $X^8$ are each independently a hydrogen atom or a substituent,
where $X^4$ and $X^5$, $X^5$ and $X^6$, $X^6$ and $X^7$ as well as $X^7$ and $X^8$ may each be joined together to form a ring, or $Y^1$ and $A^1$ as well as $Y^1$ and $X^4$ may each be joined together to form a ring, and
m is 1 or 2, and n is 1 or 0, provided that n is 1 when m is 1, and n is 0 when m is 2; and a compound represented by the following general formula (4-2):

[Formula 29]

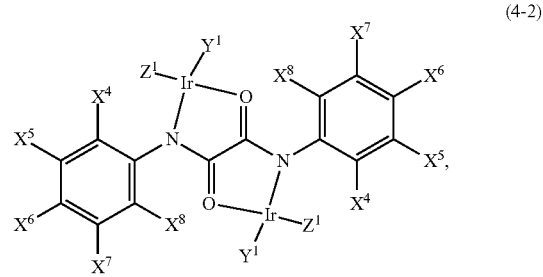

wherein:
$Y^1$, $Z^1$, $X^4$, $X^5$, $X^6$, $X^7$ and $X^8$ are as defined above.

In addition, another preferred iridium complex may be specifically exemplified by a compound represented by the following general formula (4-1a):

[Formula 30]

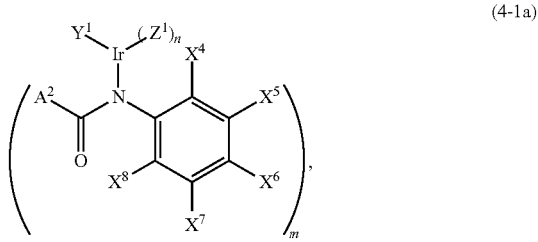

wherein:
$Y^1$, $Z^1$, $X^4$, $X^5$, $X^6$, $X^7$, $X^8$, m and n are as defined above,
$A^2$ is an optionally substituted aryl group or an optionally substituted carbonyl group, where $A^2$ may partially coordinate to the iridium atom, and/or $Y^1$ and $A^2$ as well as $Y^1$ and $X^4$ may each be joined together to form a ring.

It should be noted that these iridium complexes may each form a multimer (e.g., a dimer) via the hydrido group, the anionic group or the ligand.

As intended herein, an optionally substituted cyclopentadienyl group refers to a group configured such that 0 to 5 hydrogen atoms in a pentadienyl group are replaced with a substituent(s), as exemplified by a pentadienyl group, a 1,2,3,4,5-pentamethyl-cyclopentadienyl group (Cp*), a 1-hydroxymethyl-2,3,4,5-tetramethylcyclopentadienyl group, a 1-hydroxyethyl-2,3,4,5-tetraethylcyclopentadienyl group, etc.

Likewise, an optionally substituted indenyl group refers to a group configured such that 0 to 7 hydrogen atoms in an indenyl group are replaced with a substituent(s), as exemplified by an indenyl group, a 1,2,3-trimethylindenyl group, a 1,2,3,4,5,6,7-heptamethylindenyl group, etc.

Examples of an anionic group include a hydroxyl group, an oxo group, an alkoxy group, an aryloxy group, a fluoro group, a chloro group, a bromo group, an iodo group, an acetoxy group, a trifluoroacetoxy group, a trifluoromethanesulfonate group, a tetrafluoroborate group, a tetrahydroborate group, a tetrakis(pentafluorophenyl)borate group, a hexafluorophosphate group, a tetrakis[3,5-bis(trifluoromethyl)phenyl]borate group, etc.

Specific examples of an alkoxy group include a methoxy group, an ethoxy group, an isopropoxy group, etc.

Specific examples of an aryloxy group include a phenoxy group, etc.

An aryl group may be exemplified by a monocyclic, polycyclic or fused polycyclic aryl group preferably containing 6 to 18 carbon atoms, more preferably containing 6 to 14 carbon atoms. Specific examples include a phenyl group, a naphthyl group, an anthryl group, a phenanthryl group, a biphenyl group, etc.

A heterocyclyl group may be exemplified by a heteroaryl group or a heterocycloalkyl group, which contains 2 to 15 carbon atoms and contains at least one, preferably 1 to 3 heteroatoms such as a nitrogen atom, an oxygen atom and/or a sulfur atom.

A heteroaryl group may be exemplified by a 5- or 6-membered monocyclic heteroaryl group, a polycyclic or fused polycyclic heteroaryl group. Specific examples include a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphthyridyl group, a cinnolyl group, a benzoimidazolyl group, a benzoxazolyl group, a benzothiazolyl group, an acridyl group, an acridinyl group, etc.

A heterocycloalkyl group may be exemplified by a 3- to 6-membered heterocycloalkyl group. Specific examples include an aziridino group, an azetidino group, a pyrrolidino group, a piperidino group, an oxolano group, an oxano group, a morpholino group, etc.

An optionally substituted carbonyl group refers to a group represented by —CO—$R^7$, —CO—$OR^8$ or —CO—$NR^9R^{10}$, wherein $R^7$, $R^8$, $R^9$ and $R^{10}$ each independently represent a hydrogen atom, an optionally substituted alkyl group, an optionally substituted aryl group, an optionally substituted heterocyclyl group, or an optionally substituted aralkyl group.

As intended herein, substituents may be of any various types including, but not limited to, an alkyl group, an alkenyl group, an alkynyl group, an aryl group, a heterocyclyl group, an aralkyl group, an alkoxy group, an aryloxy group, a halogeno group, a cyano group, a nitro group, an oxo group, an optionally substituted carbonyl group, a carboxyl group, a sulfonyl group, a sulfenyl group, a sulfinyl group, a sulfo group, a mercapto group, a substituted silyl group, an optionally protected hydroxyl group, an optionally protected amino group, a substituted phosphino group, a substituted phosphonyl group, etc. The aryl group, heterocyclyl group, alkoxy group, aryloxy group and optionally substituted carbonyl group intended here are as defined above. Moreover, these substituents may further be substituted with other substituents.

For example, as intended herein, substituents on an optionally substituted alkyl group, an optionally substituted alkenyl group, an optionally substituted alkynyl group, an optionally substituted aryl group, an optionally substituted heterocyclyl group, an optionally substituted aralkyl group, an optionally substituted alkoxy group, an optionally substituted aryloxy group and an optionally substituted amino group are preferably an alkyl group, an alkoxy group, an alkenyl group, an alkynyl group, an aryloxy group, a halogeno group, an optionally protected hydroxyl group, a halogeno group, an optionally substituted carbonyl group and an optionally protected amino group.

Likewise, as intended herein, substituents on an optionally substituted cyclopentadienyl group and an optionally substituted indenyl group are preferably a methyl group and an ethyl group, with a methyl group being more preferred.

Substituents on $X^4$, $X^5$, $X^6$, $X^7$ and $X^8$ are preferably an alkyl group, an alkoxy group, a halogeno group and an optionally protected amino group.

An alkyl group may be exemplified by a linear or branched alkyl group and a cycloalkyl group. Examples of a linear or branched alkyl group include those containing 1 to 50 carbon atoms, preferably 1 to 20 carbon atoms, as exemplified by a methyl group, an ethyl group, a n-propyl group, an isopropyl group, a n-butyl group, an isobutyl group, a s-butyl group, a tert-butyl group, a n-pentyl group, a n-hexyl group, a n-octyl group, etc. Examples of a cycloalkyl group include monocyclic, polycyclic or fused polycyclic cycloalkyl groups containing 3 to 20 carbon atoms, more preferably 3 to 10 carbon atoms, as exemplified by a cyclopropyl group, a cyclopentyl group, a cyclohexyl group, etc.

An alkenyl group may be exemplified by a linear or branched alkenyl group. Examples of a linear or branched alkenyl group include those containing 1 to 50 carbon atoms, preferably 1 to 20 carbon atoms, as exemplified by a vinyl group, a 1-propenyl group, a 1-butenyl group, a 1-hexenyl group, a 1-octyl group, a 1-decenyl group, etc.

An alkynyl group may be exemplified by a linear or branched alkynyl group. Examples of a linear or branched alkynyl group include those containing 1 to 50 carbon atoms, preferably 1 to 20 carbon atoms, as exemplified by an ethynyl group, a 1-propynyl group, a 1-butynyl group, etc.

An aralkyl group refers to a group configured such that at least one hydrogen atom in an alkyl group as mentioned above is replaced with an aryl group as mentioned above. Preferred examples include aralkyl groups containing 7 to 15 carbon atoms, as specifically exemplified by a benzyl group, a 1-phenylethyl group, a 2-phenylethyl group, a 1-phenylpropyl group, a 3-naphthylpropyl group, etc.

A halogeno group may be exemplified by a fluoro group, a chloro group, a bromo group, and an iodo group.

A substituted silyl group refers to a group configured such that three hydrogen atoms in a silyl group are each independently replaced with an alkyl group as mentioned above, a cycloalkyl group as mentioned above, an aryl group as mentioned above, an aralkyl group as mentioned above, etc. Specific examples include a trimethylsilyl group, a triethylsilyl group, a tert-butyldimethylsilyl group, a tert-butyldiphenylsilyl group, a triphenylsilyl group, etc.

An optionally protected hydroxyl group may be exemplified by an unprotected hydroxyl group or a hydroxyl group which may be protected with a protecting group for hydroxyl groups commonly used for peptide synthesis and other purposes, such as a silyl group (e.g., a trimethylsilyl group, a tert-butyldimethylsilyl group, a tert-butyldiphenylsilyl group), a benzyl group or a methoxymethyl group, as shown in Protective Groups in Organic Synthesis Second Edition, JOHN WILEY & SONS, INC. 1991.

An optionally protected amino group may be exemplified by an unprotected amino group; a mono- or di-alkylamino group (e.g., an N-methylamino group, an N,N-dimethylamino group, an N,N-diethylamino group, an N,N-diisopropylamino group, an N-cyclohexylamino group); a mono- or di-arylamino group (e.g., an N-phenylamino group, an N,N-diphenylamino group, an N-naphthylamino group, an N-naphthyl-N-phenylamino group); a mono- or di-aralkylamino group (e.g., an N-benzylamino group, an N,N-dibenzylamino group); an acylamino group (e.g., a formylamino group, an acetylamino group, a propionylamino group, a pivaloylamino group, a pentanoylamino group, a hexanoylamino group, a benzoylamino group); an alkoxycarbonylamino group (e.g., a methoxycarbonylamino group, an ethoxycarbonylamino group, a n-propoxy-carbonylamino group, a n-butoxycarbonylamino group, a tert-butoxycarbonylamino group, a pentyloxycarbonylamino group, a hexyloxycarbonylamino group); an aryloxycarbonylamino group (e.g., a phenyloxycarbonylamino group); an aralkyloxycarbonylamino group (e.g., a benzyloxycarbonylamino group), etc. Further examples of an optionally protected amino group include amino groups protected with protecting groups for amino groups commonly used for peptide synthesis and other purposes as shown in the above literature.

A substituted phosphino group refers to a group configured such that two hydrogen atoms in a phosphino group are each replaced with an alkyl group as mentioned above, a cycloalkyl group as mentioned above, an aryl group as mentioned above, an aralkyl group as mentioned above, etc. Specific examples include a diphenylphosphino group, a bis(4-methylphenyl)phosphino group, a bis(3,5-dimethylphenyl)phosphino group, a dicyclohexylphosphino group, etc.

A substituted phosphonyl group refers to a group configured such that two hydrogen atoms in a phosphonyl group are each replaced with an alkyl group as mentioned above, a cycloalkyl group as mentioned above, an aryl group as mentioned above, an aralkyl group as mentioned above, etc. Specific examples include a dimethylphosphonyl group, a diethylphosphonyl group, a diphenylphosphonyl group, etc.

In one embodiment of the present invention, preferred is an iridium complex wherein $Y^1$ is an optionally substituted cyclopentadienyl group, $Z^1$ is an anionic group (e.g., a halogeno group), and $X^4$, $X^5$, $X^6$, $X^7$ and $X^8$ are each independently a hydrogen atom or a substituent (e.g., an alkyl group, an alkoxy group, a hydroxyl group, a halogeno group, an optionally protected amino group).

In one embodiment of the present invention, preferred is an iridium complex wherein $Y^1$ is an optionally substituted cyclopentadienyl group, $Z^1$ is an anionic group (e.g., a halogeno group), $A^1$ is an optionally substituted phenyl group, $A^1$ may partially coordinate to the iridium atom, and $X^4$, $X^5$, $X^6$, $X^7$ and $X^8$ are each independently a hydrogen atom or a substituent (e.g., an alkyl group, an alkoxy group, a halogeno group, an optionally protected amino group).

In one embodiment of the present invention, preferred is an iridium complex wherein $Y^1$ is an optionally substituted cyclopentadienyl group, $Z^1$ is an anionic group (e.g., a halogeno group), $A^1$ is an optionally substituted heterocyclyl group (e.g., a pyridyl group), $A^1$ may partially coordinate to the iridium atom, and $X^4$, $X^5$, $X^6$, $X^7$ and $X^8$ are each independently a hydrogen atom or a substituent (preferably an alkyl group, an alkoxy group, a hydroxyl group, a halogeno group, an optionally protected amino group).

In one embodiment of the present invention, preferred is an iridium complex wherein $Y^1$ is an optionally substituted cyclopentadienyl group, $Z^1$ is an anionic group (e.g., a halogeno group), $A^1$ is an optionally substituted carbonyl group, e.g., $-CO-NR^9R^{10}$ (wherein $R^9$ and $R^{10}$ each independently represent a hydrogen atom, an optionally substituted alkyl group, an optionally substituted aryl group, an optionally substituted heterocyclyl group, or an optionally substituted aralkyl group), $A^1$ may partially coordinate to the iridium atom, and $X^4$, $X^5$, $X^6$, $X^7$ and $X^8$ are each independently a hydrogen atom or a substituent (preferably an alkyl group, an alkoxy group, a halogeno group, an optionally protected amino group). In this case, one ligand may coordinate to two iridium atoms.

Preferred specific examples of an iridium complex include, but are not limited to, the following compounds, by way of example.

[Formula 31A]

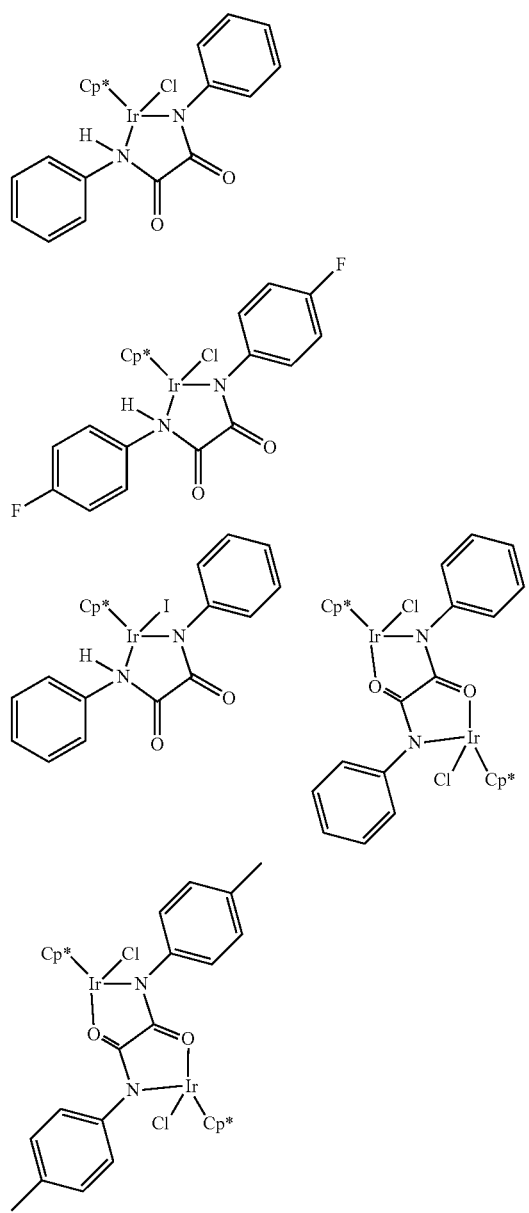

-continued
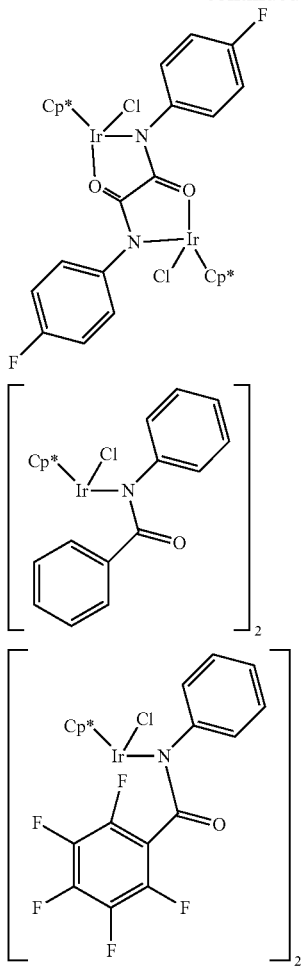
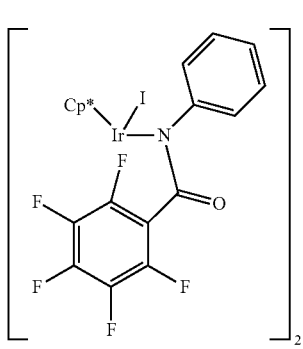
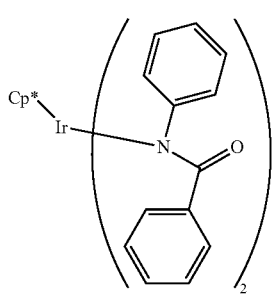
-continued
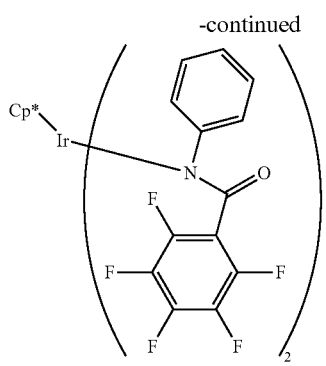
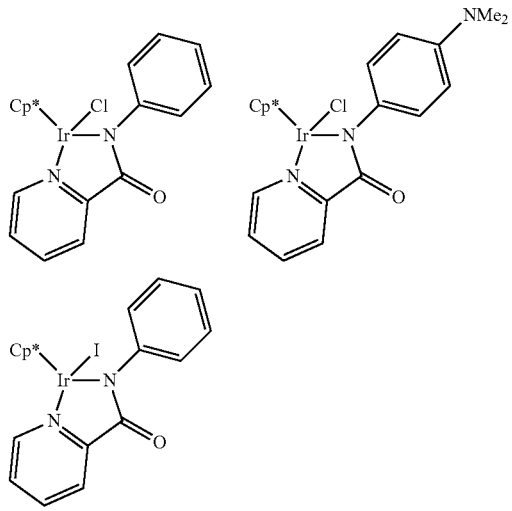
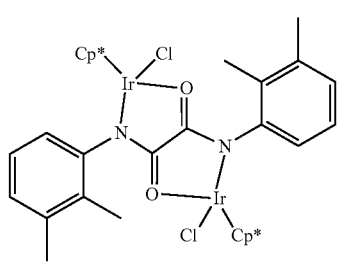
Cp*: 1,2,3,4,5-pentamethylcyclopentadienyl
[Formula 31B]
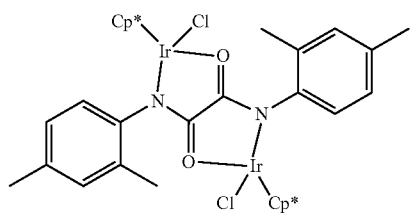

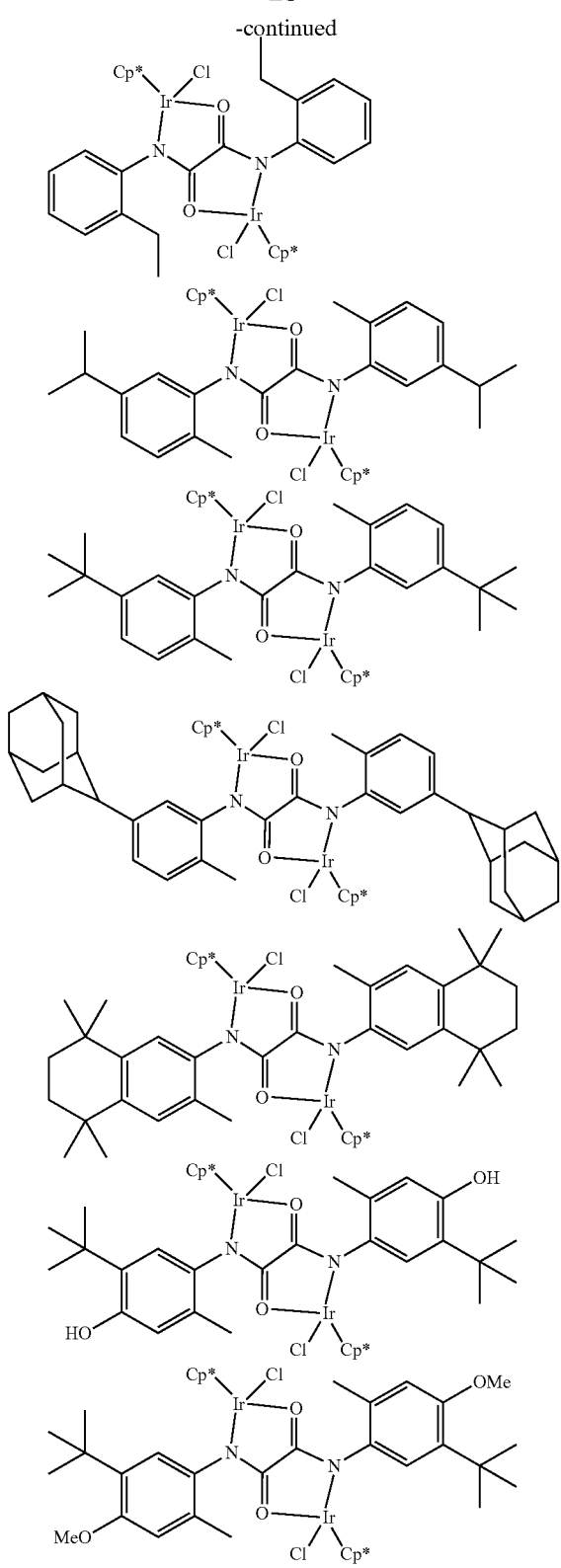

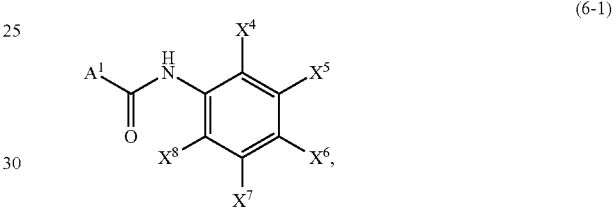

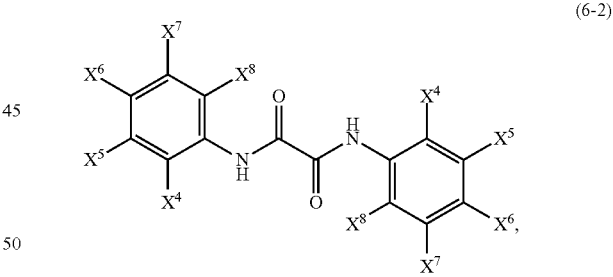

These metal complexes can be synthesized, for example, by the method described in Science of Synthesis, Trost, B. M. Ed: Thieme, 2001 (Non-patent Literature 4) or the method described in Encyclopedia of Experimental Chemistry, volume 21, edited by The Chemical Society of Japan: MARUZEN Co., Ltd., Japan, 2004 (Non-patent Literature 5). More specifically, they can be prepared by mixing an iridium compound and a ligand in the presence of a base.

Such an iridium compound may include not only the above iridium complexes, but also inorganic iridium compounds. Specific examples of inorganic iridium compounds include iridium(III) chloride hydrate ($IrCl_3 \cdot nH_2O$), chloroiridate(IV) hydrate ($H_2IrCl_6 \cdot nH_2O$), iridium(IV) nitrate ($Ir(NO_3)_4$), ammonium chloroiridate(IV) (($NH_4)_2IrCl_6$), etc.

The above metal complexes may be those prepared in advance, those prepared at the time of use, or those prepared within the reaction system.

When an iridium complex is prepared within the reaction system, for example, an iridium compound represented by the following general formula (5-1) or a dimer thereof:

$$[Y^1IrZ^1{}_2] \quad (5\text{-}1),$$

wherein:

$Y^1$ and $Z^1$ are as defined above; is mixed with an anilide represented by the following general formula (6-1):

[Formula 32]

wherein:

$A^1$, $X^4$, $X^1$, $X^6$, $X^7$ and $X^8$ are as defined above; or with an anilide represented by the following general formula (6-2):

[Formula 33]

wherein:

$X^4$, $X^5$, $X^6$, $X^7$ and $X^8$ are as defined above;

to form an iridium complex within the reaction system.

In one embodiment of the present invention, when an iridium complex is prepared within the reaction system, for example, an iridium compound represented by the following general formula (5-2) or a dimer thereof:

$$[Cp^*IrX_2] \quad (5\text{-}2),$$

wherein:

Cp* is 1,2,3,4,5-pentamethylcyclopentadienyl, and

X is a chloro group, a bromo group, or an iodo group; is mixed with an anilide represented by the following general formula (6-1):

[Formula 34]

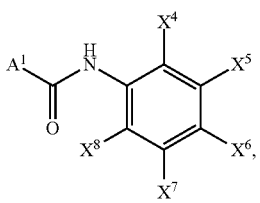

(6-1)

wherein:

$A^1$, $X^4$, $X^5$, $X^6$, $X^7$ and $X^8$ are as defined above; or with an anilide represented by the following general formula (6-2):

[Formula 35]

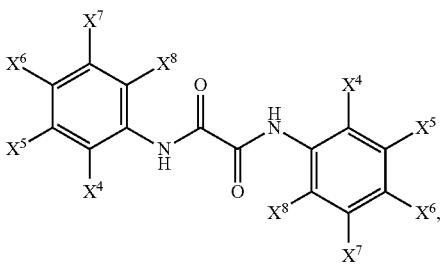

(6-2)

wherein:

$X^4$, $X^5$, $X^6$, $X^7$ and $X^8$ are as defined above;

to form an iridium complex within the reaction system.

In one embodiment of the present invention, such an anilide may be an anilide represented by the following general formula (6-1a):

[Formula 36]

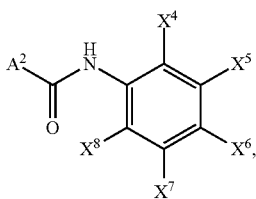

(6-1a)

wherein:

$A^2$, $X^4$, $X^5$, $X^6$, $X^7$ and $X^8$ are as defined above.

Examples of an anilide serving as a ligand areas described above.

The amount of the ligand to be used is preferably 0.1 to 200 equivalents (molar equivalents), more preferably 0.5 to 100 equivalents, and even more preferably 0.5 to 50 equivalents per iridium atom.

[Ruthenium Complex]

Examples of a ruthenium complex for use in the present invention include the following complexes: dichlorotris(triphenylphosphine)ruthenium(II) ([RuCl$_2$(PPh$_3$)$_3$]), dibromotris(triphenylphosphine)ruthenium(II) ([RuBr$_2$(PPh$_3$)$_3$]), diiodotris(triphenylphosphine)ruthenium(II) ([RuI$_2$(PPh$_3$)$_3$]), dodecacarbonyltriruthenium(0) ([Ru$_3$(CO)$_{12}$]), dichloro(benzene)ruthenium(II) dimer ([RuCl$_2$(benzene)]$_2$), dibromo(benzene)-ruthenium(II) dimer ([RuBr$_2$(benzene)]$_2$), diiodo(benzene)ruthenium(II) dimer ([RuI$_2$(benzene)]$_2$), dichloro(mesitylene)ruthenium(II) dimer ([RuCl$_2$(mesitylene)]$_2$), dibromo(mesitylene)ruthenium(II) dimer ([RuBr$_2$(mesitylene)]$_2$), diiodo(mesitylene)-ruthenium(II) dimer ([RuI$_2$(mesitylene)]$_2$), dichloro(p-cymene)ruthenium(II) dimer ([RuCl$_2$(p-cymene)]$_2$), dibromo(p-cymene)ruthenium(II) dimer ([RuBr$_2$(p-cymene)]$_2$), diiodo(p-cymene)ruthenium(II) dimer ([RuI$_2$(p-cymene)]$_2$), dichloro(hexamethylbenzene)ruthenium(II) dimer ([RuCl$_2$(C$_6$(CH$_3$)$_6$)]$_2$), dibromo(hexamethylbenzene)-ruthenium(II) dimer ([RuBr$_2$(C$_6$(CH$_3$)$_6$)]$_2$), diiodo(hexamethylbenzene)ruthenium(II) dimer ([RuI$_2$(C$_6$(CH$_3$)$_6$)]$_2$), carbonylchlorohydridotris(triphenylphosphine)ruthenium(II) ([RuHCl(CO)(PPh$_3$)$_3$]), tris(acetylacetonato)ruthenium(III) ([Ru(acac)$_3$]), tris(dipivaloylmethanato)ruthenium(III) ([Ru(dpm)$_3$]), dichloro(cyclooctadiene)-ruthenium ([RuCl$_2$(cod)]$_a$), dibromo(cyclooctadiene)ruthenium ([RuBr$_2$(cod)]$_a$), diiodo(cyclooctadiene)ruthenium ([RuI$_2$(cod)]$_a$), dichloro(norbornadiene)ruthenium ([RuCl$_2$(nbd)]$_a$), dibromo(norbornadiene)ruthenium ([RuBr$_2$(nbd)]$_a$), diiodo-(norbornadiene)ruthenium ([Ru$_2$(nbd)]$_a$), etc., wherein a is an integer of 1 to 3.

Other examples of a ruthenium complex include those having a ligand L which is as defined in [Iridium complex] above.

Specific examples of ruthenium complexes having a ligand L include the following compounds, by way of example: Ru(OAc)$_2$L$^1_b$, Ru(OCOCF$_3$)$_2$L$^1_b$, Ru$_2$Cl$_4$(L$^1$)$_{2b}$NEt$_3$, [RuCl(benzene)L$^1_b$]Cl, [RuBr(benzene)L$^1_b$]Br, [RuI(benzene)L$^1_b$]I, [RuCl(p-cymene)L$^1_b$]Cl, [RuBr(p-cymene)L$^1_b$]Br, [RuI(p-cymene)L$^1_b$]I, [[RuClL$^1_b$]$_2$(μ-Cl)$_3$][Me$_2$NH$_2$], [[RuClL$^1_b$]$_2$(μ-Cl)$_3$][Et$_2$NH$_2$], RuCl$_2$L$^1_b$, RuBr$_2$L$^1_b$, RuI$_2$L$^1_b$, RuCl$_2$L$^1_b$L$^2_c$, RuBr$_2$L$^1_b$L$^2_c$, RuI$_2$L$^1_b$L$^2_c$, RuClL$^2_c$(p-cymene), RuClL$^2_c$(mesitylene), dichlorobis[2-(diphenylphosphino)ethylamine]ruthenium, carbonylchlorohydrido[bis(2-diphenylphosphinoethyl)amino]ruthenium (Ru-MACHO), carbonylhydrido-(tetrahydroborate)[bis(2-diphenylphosphinoethyl)amino]ruthenium (Ru-MACHO—BH), etc.

In the above compounds, b=2 when $L^1$ is a monodentate phosphine ligand, b=1 when $L^1$ is a bidentate phosphine ligand; c=2 when $L^2$ is a monodentate nitrogen-containing ligand, and c=1 when $L^2$ is a bidentate nitrogen-containing ligand.

Moreover, a preferred ruthenium complex may be specifically exemplified by a ruthenium complex selected from the group consisting of:

a compound represented by the following general formula (4-3) or a dimer thereof:

[Formula 37]

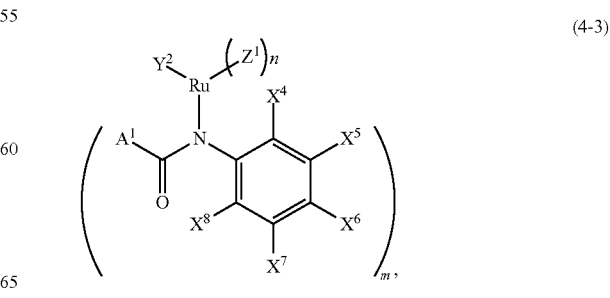

(4-3)

wherein:

Y² is an optionally substituted arene,

Z¹ is a hydrido or anionic group,

A¹ is an optionally substituted aryl group, an optionally substituted heterocyclyl group or an optionally substituted carbonyl group, where A¹ may partially coordinate to the ruthenium atom, X⁴, X⁵, X⁶, X⁷ and X⁸ are each independently a hydrogen atom or a substituent, where X⁴ and X⁵, X⁵ and X⁶, X⁶ and X⁷ as well as X⁷ and X⁸ may each be joined together to form a ring, and/or Y¹ and A¹ as well as Y¹ and X⁴ may each be joined together to form a ring, and m is 1 or 2, and n is 1 or 0, provided that n is 1 when in is 1, and n is 0 when m is 2; or a compound represented by the following general formula (4-4):

[Formula 38]

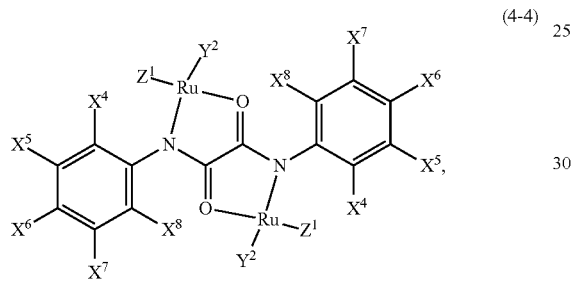

(4-4)

wherein:

Y², Z¹, X⁴, X⁵, X⁶, X⁷ and X⁸ are as defined above.

It should be noted that these ruthenium complexes may each form a multimer (e.g., a dimer) via the hydrido group, the anionic group or the ligand.

As intended herein, an arene may be exemplified by benzene, naphthalene, etc. Examples of substituents on an optionally substituted arene include an alkyl group, an alkoxy group, an alkenyl group, an alkynyl group, an aryloxy group, a halogeno group, an optionally protected hydroxyl group, a halogeno group, an optionally substituted carbonyl group, and an optionally protected amino group. Specific examples of an optionally substituted arene include benzene, p-cymene, mesitylene, 1,2,3,4,5,6-hexamethylbenzene, etc.

It should be noted that Z¹, A¹, X⁴, X⁵, X⁶, X⁷, X⁸, m and n in the above formulae are the same as defined for iridium complexes.

In one embodiment of the present invention, preferred is a ruthenium complex of general formula (4-4) wherein Y² is an optionally substituted arene, Z¹ is an anionic group (e.g., a halogeno group), and X⁴, X⁵, X⁶, X⁷ and X⁸ are each independently a hydrogen atom or a substituent (e.g., an alkyl group, an alkoxy group, a halogeno group, an optionally protected amino group).

Preferred specific examples of a ruthenium complex include, but are not limited to, the following compounds, by way of example.

[Formula 39]

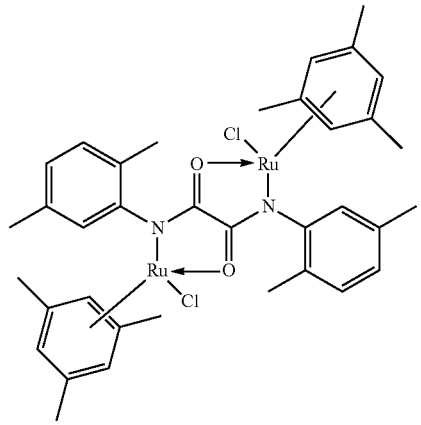

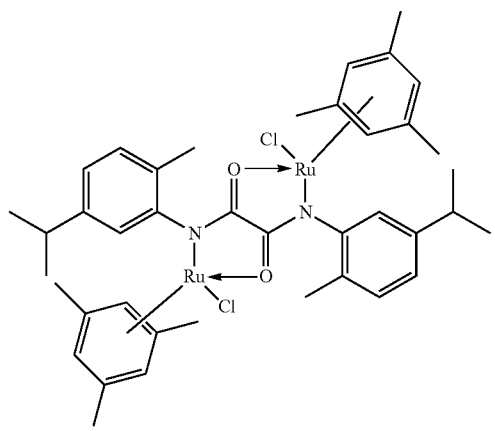

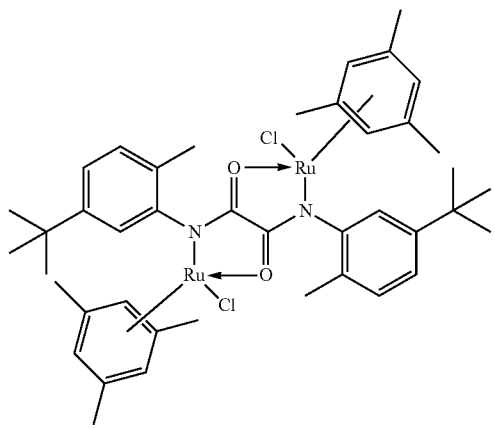

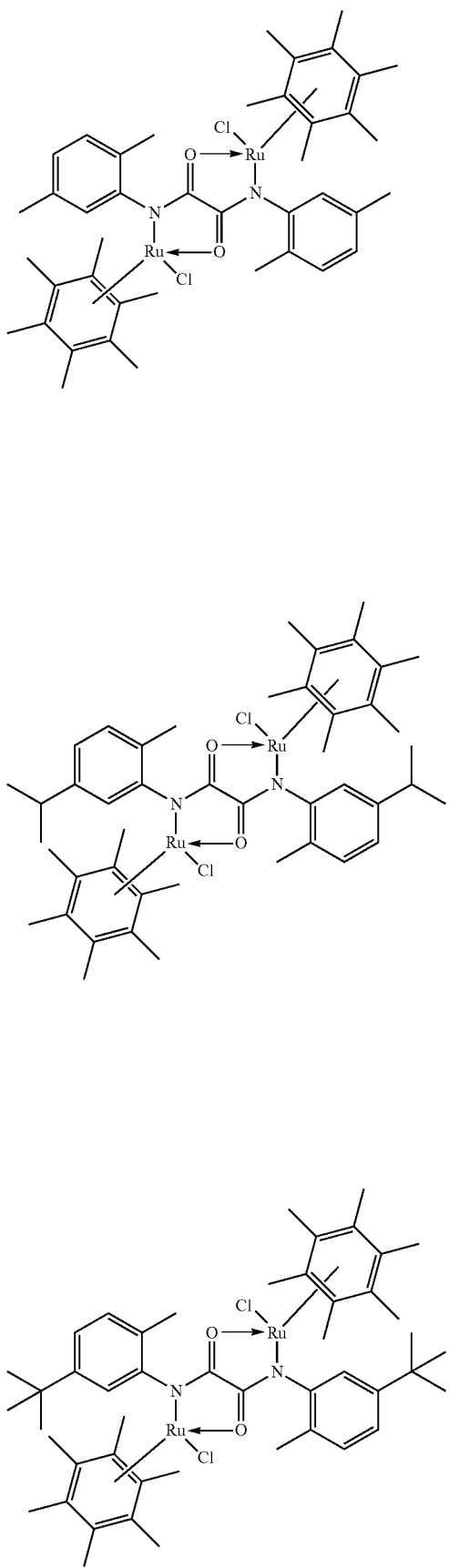
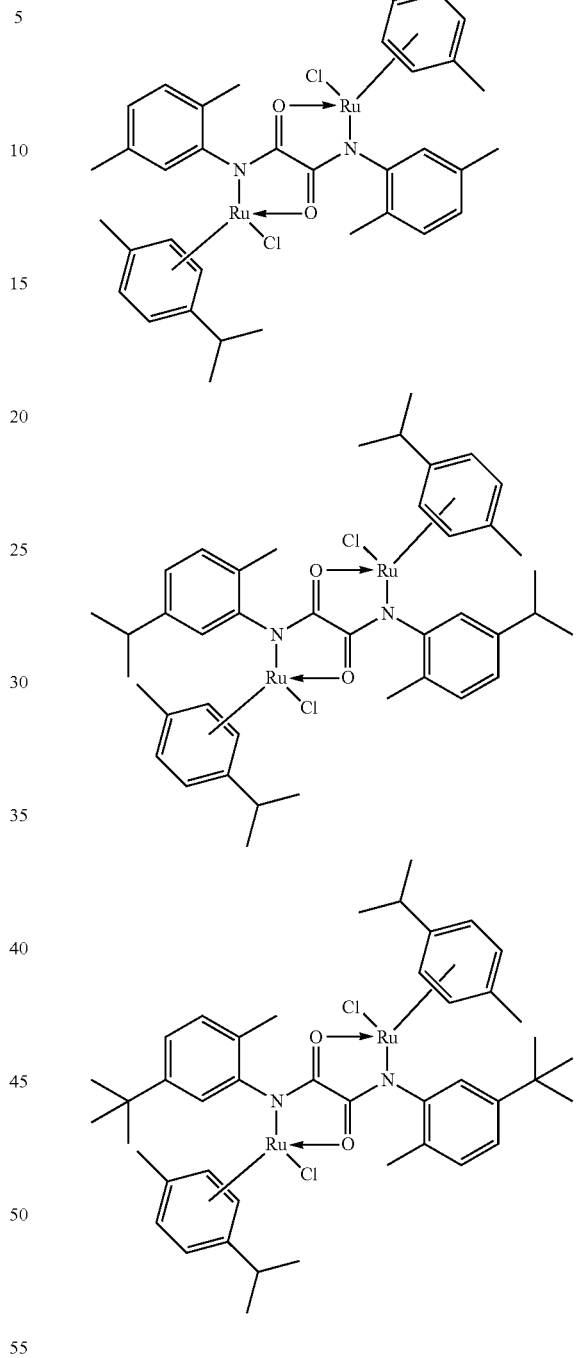

These metal complexes can be synthesized, for example, by the method described in Science of Synthesis, Trost, B. M. Ed: Thieme, 2001 (Non-patent Literature 4) or the method described in Encyclopedia of Experimental Chemistry, volume 21, edited by The Chemical Society of Japan: MARUZEN Co., Ltd., Japan, 2004 (Non-patent Literature 5). More specifically, they can be prepared by mixing a ruthenium compound and a ligand in the presence of a base.

The above metal complexes may be those prepared in advance, those prepared at the time of use, or those prepared within the reaction system.

When a ruthenium complex is prepared within the reaction system, for example, a ruthenium compound represented by the following general formula (5-3) or a dimer thereof:

$$[Y^2RuZ^1{}_2] \quad (5\text{-}3),$$

wherein $Y^2$ and $Z^1$ are as defined above; is mixed with an anilide represented by the following general formula (6-1):

[Formula 40]

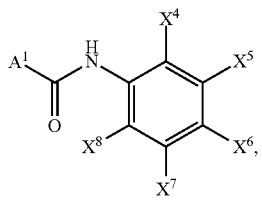
(6-1)

wherein:

$A^1$, $X^4$, $X^5$, $X^6$, $X^7$ and $X^8$ are as defined above; or with an anilide represented by the following general formula (6-2):

[Formula 41]

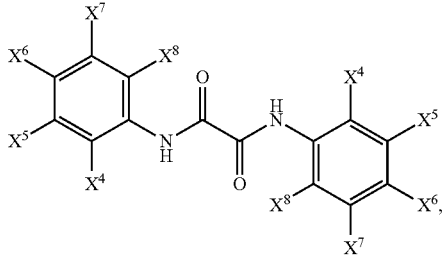
(6-2)

wherein:

$X^4$, $X^5$, $X^6$, $X^7$ and $X^8$ are as defined above;

to form a ruthenium complex within the reaction system.

In one embodiment of the present invention, when a ruthenium complex is prepared within the reaction system, for example, a ruthenium compound represented by the following general formula (5-4) or a dimer thereof:

$$[Y^2RuX_2] \quad (5\text{-}4),$$

wherein:

$Y^2$ is as defined above, and

X is a chloro group, a bromo group, or an iodo group; is mixed with an anilide represented by the following general formula (6-1):

[Formula 42]

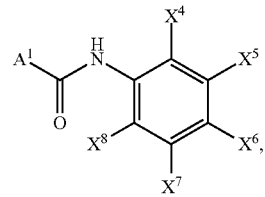
(6-1)

wherein:

$A^1$, $X^4$, $X^5$, $X^6$, $X^7$ and $X^8$ are as defined above; or with an anilide represented by the following general formula (6-2):

[Formula 43]

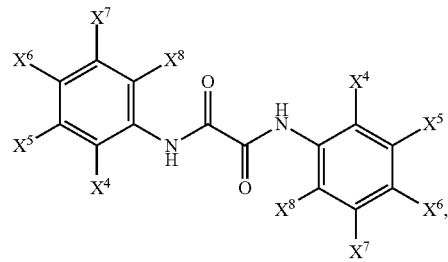
(6-2)

wherein:

$X^4$, $X^5$, $X^6$, $X^7$ and $X^8$ are as defined above;

to form a ruthenium complex within the reaction system.

In one embodiment of the present invention, such an anilide may be an anilide represented by the following general formula (6-1a):

[Formula 44]

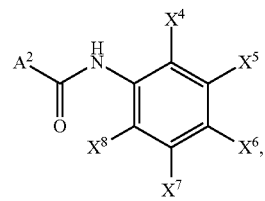
(6-1a)

wherein:

$A^2$, $X^4$, $X^5$, $X^6$, $X^7$ and $X^8$ are as defined above.

Examples of an anilide serving as a ligand are as described above.

The amount of the ligand to be used is preferably 0.1 to 200 equivalents (molar equivalents), more preferably 0.5 to 100 equivalents, and even more preferably 0.5 to 50 equivalents per ruthenium atom.

[Solid Base]

The solid base to be used in the present invention is not limited in any way, as long as it is at least one selected from the group consisting of a layered double hydroxide, a composite oxide and calcium hydroxide.

[Layered Double Hydroxide]

In one embodiment of the present invention, a layered double hydroxide is used as a solid base. Such a layered double hydroxide is preferably a hydrotalcite-type compound represented by general formula (7):

$$[(M^1)_{y-x}(M^2)_x(OH)_{2y}(A)_{x/k} \cdot zH_2O] \tag{7}$$

In general formula (7), $M^1$ represents a divalent ion of one metal selected from the group consisting of Mg, Fe, Zn, Ca, Li, Ni, Co and Cu or divalent ions of multiple metals selected at any ratio from these metals, and $M^2$ represents a trivalent ion of one metal selected from the group consisting of Al, Fe and Mn or trivalent ions of multiple metals selected at any ratio from these metals.

A represents an interlayer anion, and k represents the valency of A. Examples of an interlayer anion include anions such as carbonate ion, sulfate ion, fluoride ion, chloride ion, bromide ion, iodide ion, hydroxide ion, and acetate ion. Moreover, x, y and z each represent a natural number and they satisfy the following requirement: $x<y$ and $0 \leq z<y$.

Among them, preferred as layered double hydroxides are those having one or more metal elements selected from the group consisting of aluminum, magnesium and calcium.

Specific examples of layered double hydroxides include desautelsite, hydrotalcite, iowaite, pyroaurite, takovite, wermlandite, and zaccagnite, etc.

Among them, preferred is hydrotalcite represented by general formula (7a):

$$[Mg_{y-x}Al_x(OH)_{2y}(A)_{x/k} \cdot zH_2O] \tag{7a},$$

wherein: x, y, k and z are as defined above; and particularly preferred is $Mg_6Al_2(CO_3)(OH)_{16} \cdot 4H_2O$.

A layered double hydroxide may be prepared by mixing a basic solution into an aqueous solution containing a mixture of a divalent metal salt and a trivalent metal salt. A hydrotalcite-type compound can be synthesized, for example, by the method described in U.S. Pat. No. 4,351,814 or the method described in U.S. Pat. No. 4,904,457 or 5,250,279. More specifically, it may be prepared by adding aqueous sodium hydroxide and aqueous sodium carbonate dropwise to a mixed aqueous solution of magnesium chloride and aluminum chloride, by way of example. Alternatively, commercially available hydrotalcite may be used for this purpose.

[Composite Oxide]

In one embodiment of the present invention, a composite oxide is used as a solid base. Such a composite oxide has two or more metal elements, and at least one of these metal elements is preferably selected from the group consisting of aluminum, magnesium and calcium. Specific examples of a composite oxide include sodium aluminate, calcium aluminate, magnesium silicate, calcium silicate, aluminum silicate, magnesium aluminosilicate, and magnesium aluminometasilicate, etc.

[Calcium Hydroxide]

In one embodiment of the present invention, calcium hydroxide is used as a solid base. According to a preferred embodiment of the present invention, even when used alone as a solid base, calcium hydroxide can exert high catalytic activity in the reaction of converting a hydroxyl group of an alcohol.

It should be noted that these solid bases may be used either alone or in combination.

[Alcohol]

The alcohol to be used in the present invention is represented by the following general formula (1):

[Formula 45]

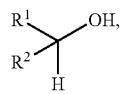
(1)

wherein:

$R^1$ and $R^2$ are each independently a hydrogen atom, an optionally substituted alkyl group, an optionally substituted aryl group, an optionally substituted heterocyclyl group or an optionally substituted aralkyl group, where at least one of $R^1$ and $R^2$ may have a hydroxyl group as a substituent, and/or $R^1$ and $R^2$ may be joined together to form a ring.

It should be noted that the alkyl group, aryl group, heterocyclyl group, aralkyl group and substituent intended here are as defined above.

In one embodiment of the present invention, it is preferred that $R^1$ is an optionally substituted alkyl group or an optionally substituted aryl group, $R^1$ may have a hydroxyl group as a substituent, and $R^2$ is a hydrogen atom.

When $R^1$ and $R^2$ are joined together to form a ring, the above ring may have a saturated or unsaturated ring structure, as exemplified by an optionally substituted cycloalkyl group, etc.

When at least one of $R^1$ and $R^2$ has a hydroxyl group as a substituent, the alcohol is a polyhydric alcohol. Examples of a polyhydric alcohol include a compound represented by the following general formula (1-1):

[Formula 46]

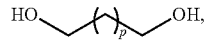
(1-1)

wherein:

p is an integer of 0 to 48; by way of example.

In this case, p is preferably 0 to 24, more preferably 3 to 20, and even more preferably 5 to 12.

Preferred specific examples include the following compound.

[Formula 47]

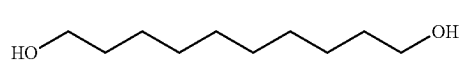
(1-1a)

[Compound Having an Active Proton]

The compound having an active proton to be used in the present invention is represented by the following general formula (2):

[Formula 48]

H-Nu (2), wherein:

Nu is a group represented by —$CHX^1$-$EWG^1$ or —$NR^3R^4$, where $X^1$ is a hydrogen atom or a substituent, $EWG^1$ is an electron-withdrawing group, and $R^3$ and $R^4$ are each independently a hydrogen atom, an optionally substituted alkyl group, an optionally substituted aryl group, an optionally substituted heterocyclyl group or an optionally substituted aralkyl group, where $R^3$ and $R^4$ may be joined together to form a ring.

The substituent, alkyl group, aryl group, heterocyclyl group and aralkyl group intended in general formula (2) are as defined above. When $R^3$ and $R^4$ are joined together to form a ring, the above ring may have a saturated ring structure, as exemplified by an optionally substituted heterocycloalkyl group, etc.

Examples of an electron-withdrawing group include an optionally substituted carbonyl group, an optionally substituted aryl group, an optionally substituted heteroaryl group, an optionally substituted sulfonyl group, an optionally substituted sulfinyl group, an optionally substituted ammonium group, an optionally substituted phosphonium group, a nitro group, a cyano group, etc. The optionally substituted carbonyl group, aryl group, heteroaryl group and substituent intended here are as defined above.

The compound having an active proton may be exemplified by a carbonyl compound represented by the following general formula (2-1):

[Formula 49]

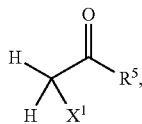

(2-1)

wherein:

$X^1$ is as defined above, and $R^5$ is a hydrogen atom, an optionally substituted alkyl group, an optionally substituted alkenyl group, an optionally substituted alkynyl group, an optionally substituted aryl group, an optionally substituted heterocyclyl group, an optionally substituted aralkyl group, an optionally substituted alkoxy group, an optionally substituted aryloxy group, an optionally substituted amino group or an optionally substituted carbonyl group, where $X^1$ and $R^5$ may be joined together to form a ring.

The substituent, alkyl group, alkenyl group, alkynyl group, aryl group, heterocyclyl group, aralkyl group, alkoxy group, aryloxy group and optionally substituted carbonyl group intended here are as defined above. When $X^1$ and $R^5$ are joined together to form a ring, the above ring may have a saturated or unsaturated ring structure, as exemplified by an optionally substituted cycloalkyl group, etc.

Specific examples of the carbonyl compound represented by general formula (2-1) include acetone, 2-butanone, 2-pentanone, 3-pentanone, acetophenone, propiophenone, ethyl acetate, butyl acetate, phenyl acetate, cyanomethyl acetate, methyl acetoacetata, methyl lactate, and cyclohexanone, etc.

The compound having an active proton may also be exemplified by a nitrile represented by the following general formula (2-2):

[Formula 50]

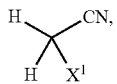

(2-2)

wherein:

$X^1$ is as defined above.

Specific examples of the nitrile represented by general formula (5) include acetonitrile, propionitrile, butyronitrile, phenylacetonitrile, and malonitrile, etc.

The compound having an active proton may further be exemplified by an amine represented by the following general formula (2-3):

[Formula 51]

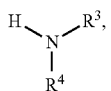

(2-3)

wherein:

$R^3$ and $R^4$ are as defined above.

Specific examples of the compound represented by general formula (2-3) include ammonia, methylamine, dimethylamine, ethylamine, diethylamine, piperidine, morpholine, aniline, etc.

[Mode of Reaction]

In the method of the present invention for converting a hydroxyl group of an alcohol, a solvent may be used as appropriate in consideration of the physical and chemical properties of the alcohol, the compound having an active proton, the metal complex and the solid base.

Examples of such a solvent include hydrocarbon-based solvents (e.g., toluene, xylene, mesitylene, decane); ester-based solvents (e.g., ethyl acetate, butyl acetate); amide-based solvents (e.g., N-methylpyrrolidone); ether-based solvents (e.g., isopropyl ether, methyl tert-butyl ether, tetrahydrofuran, methyltetrahydrofuran, 1,4-dioxane); alcohol-based solvents (e.g., isopropyl alcohol, tert-butyl alcohol, amyl alcohol); ketone-based solvents (e.g., cyclohexanone, diacetone alcohol); halogenated solvents (e.g., methylene chloride), etc. These solvents may be used either alone or in combination. The amount of the solvent to be used is not limited in any way and may be determined as appropriate. In general, it is preferably 0 to 100 times (by mass) the amount of the alcohol.

In the method of the present invention for converting a hydroxyl group of an alcohol, the amount of the compound having an active proton to be used is preferably 0.01 to 100 equivalents (molar equivalents), more preferably 0.05 to 20 equivalents, and even more preferably 0.1 to 15 equivalents relative to the alcohol.

The amount of the metal complex to be used (calculated as a metal atom) is preferably 0.0001 to 100 mol %, more preferably 0.001 to 10 mol %, and even more preferably 0.005 to 1 mol % relative to the alcohol.

The amount of at least one solid base to be used, which is selected from the group consisting of a layered double hydroxide, a composite oxide and calcium hydroxide, is generally preferably 0.1% to 500% (by mass), more preferably 1% to 100% (by mass), and even more preferably 2% to 50% (by mass) relative to the alcohol.

In one embodiment of the present invention, when the alcohol is a polyhydric alcohol, only one hydroxyl group may be converted or a plurality of hydroxyl groups may be converted.

Moreover, in one embodiment of the present invention, when the compound having an active proton has a hydroxyl group as one of its substituents, the compound may be cyclized through intramolecular reaction. Alternatively, when the compound having an active proton has a plurality of active protons, the reaction may occur at a single site or multiple sites.

Moreover, when $R^1$ in general formula (1) is attached to $X^1$ or $R^3$ in Nu in general formula (2) such that the alcohol and the compound having an active proton form a single molecule, the reaction may occur within the molecule.

In the method of the present invention for converting a hydroxyl group of an alcohol, a compound represented by general formula (3) can be produced:

[Formula 52]

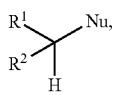

(3)

wherein:
$R^1$, $R^2$ and Nu are as defined above, where $R^1$ and $X^1$ or $R^3$ in Nu may be joined together to form a ring.

When $R^1$ and $X^1$ or $R^3$ in Nu are joined together to form a ring, the above ring may have a saturated or unsaturated ring structure, as exemplified by an optionally substituted cycloalkyl group, an optionally substituted aryl group, an optionally substituted heterocyclyl group, etc.

The compound produced by the method of the present invention for converting a hydroxyl group of an alcohol may be either a single compound or a mixture.

For example, when the compound having an active proton is the carbonyl compound represented by general formula (2-1) and the alcohol is the diol represented by general formula (1-1), the resulting product may be either one of the following general formulae (3-1) and (3-2) or a mixture thereof.

[Formula 53]

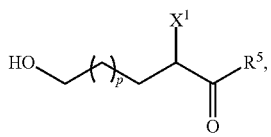

(3-1)

wherein:
$X^1$, $R^5$ and p are as defined above;

[Formula 54]

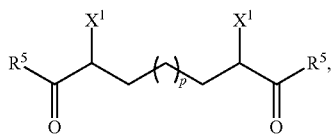

(3-2)

wherein:
$X^1$, $R^5$ and p are as defined above.

Moreover, for example, when the compound having an active proton is the amine represented by general formula (2-3) and the alcohol is the diol represented by general formula (1-1), the resulting product may be either one of the following general formulae (3-3) and (3-4) or a mixture thereof.

[Formula 55]

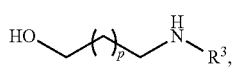

(3-3)

wherein:
$R^3$ and p are as defined above;

[Formula 56]

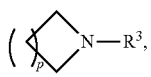

(3-4)

wherein:
$R^3$ and p are as defined above.

In one embodiment of the method of the present invention for converting a hydroxyl group of an alcohol, the compound having an active proton is the carbonyl compound represented by general formula (2-1), wherein $X^1$ is a hydrogen atom, and $R^5$ is a methyl group,
the alcohol represented by general formula (1) is a diol represented by the following formula (1-1a):

[Formula 57]

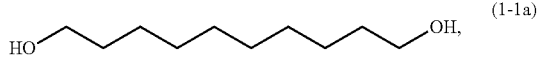

(1-1a)

the product represented by general formula (3) is a diketone represented by the following formula (3-2a):

[Formula 58]

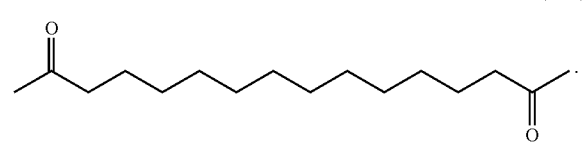

(3-2a)

In the method of the present invention for converting a hydroxyl group of an alcohol, additives may be added when required.

Examples of additives include the compounds described in Chemical Reviews 2016, 116, 4006-4123, as exemplified by water, acids, bases, inorganic salts, organic salts, phosphine compounds, amine compounds, amide compounds, etc.

Acids include inorganic acids such as hydrochloric acid, sulfuric acid and so on, as well as organic acids such as acetic acid, trifluoroacetic acid, p-toluenesulfonic acid, trifluoromethylsulfonic acid, camphorsulfonic acid and so on.

Bases include inorganic bases such as lithium hydroxide, sodium hydroxide, potassium hydroxide, magnesium hydroxide, calcium hydroxide, barium hydroxide, sodium carbonate, magnesium carbonate, potassium carbonate, calcium carbonate, cesium carbonate, magnesium oxide, and calcium oxide, as well as organic bases such as triethylamine, diazabicycloundecene, pyridine, N,N-dimethylaminopyridine, and 2,6-lutidine.

Inorganic salts include lithium chloride, sodium chloride, potassium chloride, lithium bromide, lithium iodide, lithium tetrafluoroborate, etc.

Organic salts include sodium acetate, ammonium acetate, tetrabutylammonium chloride, tetrabutylammonium bromide, tetrabutylammonium iodide, tetrabutylphosphonium iodide, etc.

Phosphine compounds include compounds as defined above for the phosphine ligand.

Amine compounds include compounds as defined above for the amine ligand.

Amide compounds include compounds as defined above for the amide ligand.

The amount of the additives to be used is preferably 0% to 200% (by mass), and more preferably 0% to 100% (by mass) relative to the alcohol.

During the reaction, water generated may be removed as appropriate by using physical means such as azeotropy or by using a desiccant such as a molecular sieve.

The reaction temperature is not limited in any way, but it is preferably 0° C. to 250° C., and more preferably room temperature to 200° C.

The reaction may be carried out under normal pressure, under elevated pressure or under reduced pressure.

The reaction atmosphere is not limited in any way, and the reaction may be carried out under a nitrogen atmosphere, under an argon atmosphere, under air atmosphere, under a carbon dioxide gas atmosphere, under a hydrogen gas atmosphere, etc.

After completion of the reaction, the product may be purified, for example, by filtration, extraction, concentration, crystallization, distillation, column chromatography and other techniques or any combination thereof.

The mode of this reaction may be either a batch or continuous mode.

EXAMPLES

The present invention will be further described in more detail by way of the following illustrative examples, although the present invention is not limited to these examples. It should be noted that the instruments shown below were used for various measurements in this Example section.

Nuclear magnetic resonance spectrometry (NMR): 400-MR-DD2 (400 MHz) (Agilent Technology) or Avance III 500 (500 MHz) (Bruker)

Internal standard: deuterochloroform (tetramethylsilane)

Mass spectrometry (HRMS): Impact II spectrometer (BRUKER)

Gas chromatography (GC): GC 4000 Plus (GL Sciences Inc., Japan) Column: HP-5 (30 m×0.320 mm×0.25 µm) (Agilent)

Inlet temperature: 250° C., detector temperature: 250° C., temperature rise condition: 100° C. (15° C./minute) to 300° C., or Inlet temperature: 230° C., detector temperature: 310° C., temperature rise condition: 100° C. (10° C./minute) to 300° C., or Inlet temperature: 230° C., detector temperature: 310° C., temperature rise condition: 50° C. (kept for 10 minutes and then 10° C./minute) to 200° C. (20° C./minute) to 300° C.

[Example 1] Synthesis of Hexadecane-2,15-dione ([Cp*IrCl$_2$]$_2$ and N,N'-diphenyloxamide)

[Formula 59]

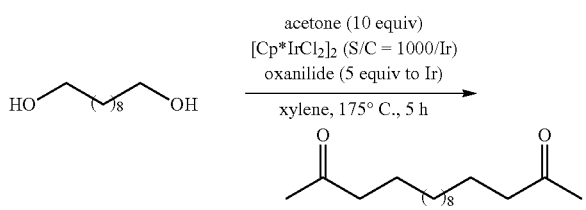

A 200 mL autoclave was charged with decane-1,10-diol (7.09 g, 40.7 mmol), hydrotalcite (Mg$_6$Al$_2$(CO$_3$)(OH)$_{16}$·4H$_2$O) (2.54 g, 35 wt % relative to decane-1,10-diol), [Cp*IrCl$_2$]$_2$ (16.2 mg, 1/1000 equivalents calculated as Ir relative to decane-1,10-diol) and N,N'-diphenyloxamide (48.7 mg, 5 equivalents relative to Ir), and then purged with nitrogen. Under a nitrogen stream, xylene (50 mL) and acetone (30 mL, 10 equivalents relative to decane-1,10-diol) were introduced into the autoclave, followed by initiation of heating and stirring. After stirring at 170° C. to 175° C. for 5 hours, the autoclave was cooled. The reaction mixture was analyzed by gas chromatography, indicating that 13-hydroxytridecan-2-one (3%) and hexadecane-2,15-dione (79%) were produced (expressed in GC area %). It should be noted that the quantitative yield of hexadecane-2,15-dione was 61%.

Example 2

After distilling off the solvent from the reaction mixture of Example 1, butyl acetate (70 mL) was added to the residue. After warming to 50° C., the mixture was cooled to −5° C. under stirring and matured for 1 hour. The generated solid was collected by filtration, washed with butyl acetate (20 mL) and then dried to obtain hexadecane-2,15-dione (5.99 g) at a GC purity of 96% (yield: 56%).

$^1$H-NMR (400 MHz, CDCl$_3$): δ=2.41 (t, J=7.6 Hz, 4H), 2.13 (s, 6H), 1.62-1.50 (m, 4H), 1.32-1.20 (m, 16H)

[Example 3] Synthesis of Hexadecane-2,15-dione ([Cp*IrCl$_2$]$_2$ and 1,2,3,4,5-pentafluorobenzanilide)

Example 1 was repeated using 1,2,3,4,5-pentafluorobenzanilide (59.2 mg, 5 equivalents relative to Ir) instead of N,N'-diphenyloxamide, thus indicating that 13-hydroxytridecan-2-one (2%) and hexadecane-2,15-dione (73%) were produced (expressed in GC area %). It should be noted that the quantitative yield of hexadecane-2,15-dione was 55%.

[Example 4] Synthesis of Hexadecane-2,15-dione ([Cp*IrCl$_2$]$_2$ and N-phenylpicolinamide)

Example 1 was repeated using N-phenylpicolinamide (40.0 mg, 5 equivalents relative to Ir) instead of N,N'- diphenyloxamide, thus indicating that 13-hydroxytridecan-2-one (4%) and hexadecane-2,15-dione (72%) were produced (expressed in GC area %). It should be noted that the quantitative yield of hexadecane-2,15-dione was 53%.

[Example 5] Synthesis of Hexadecane-2,15-dione ([Cp*IrCl$_2$]$_2$ and N,N'-diphenyloxamide; 160° C.)

Example 1 was repeated to carry out the reaction at a reaction temperature of 155° C. to 160° C., thus indicating that 13-hydroxytridecan-2-one (16%) and hexadecane-2,15-dione (66%) were produced (expressed in GC area %). It should be noted that the quantitative yield of hexadecane-2,15-dione was 49%.

[Example 6] Synthesis of Hexadecane-2,15-dione ([Cp*IrCl$_2$]$_2$ and 1,2,3,4,5-pentafluorobenzanilide; 160° C.)

Example 5 was repeated using 1,2,3,4,5-pentafluorobenzanilide (58.3 mg, 5 equivalents relative to Ir) instead of N,N'-diphenyloxamide, thus indicating that 13-hydroxytridecan-2-one (16%) and hexadecane-2,15-dione (62%) were produced (expressed in GC area %). It should be noted that the quantitative yield of hexadecane-2,15-dione was 51%.

[Example 7] Synthesis of Hexadecane-2,15-dione ([Cp*IrCl$_2$]$_2$ and Benzanilide; 160° C.)

Example 5 was repeated using benzanilide (40.3 mg, 5 equivalents relative to Ir) instead of N,N'-diphenyloxamide, thus indicating that 13-hydroxytridecan-2-one (42%) and hexadecane-2,15-dione (30%) were produced (expressed in GC area %). It should be noted that the quantitative yield of hexadecane-2,15-dione was 23%.

[Example 8] Synthesis of 13-hydroxytridecan-2-one ([Cp*IrCl$_2$]$_2$ and N-phenylthiophene-2-carboxamide; 160° C.)

Example 5 was repeated using N-phenylthiophene-2-carboxamide (41.5 mg, 5 equivalents relative to Ir) instead of N,N'-diphenyloxamide, thus indicating that 13-hydroxytridecan-2-one (70%) and hexadecane-2,15-dione (8%) were produced (expressed in GC area %). It should be noted that the quantitative yield of hexadecane-2,15-dione was 6%.

[Example 9] Synthesis of Hexadecane-2,15-dione ([Cp*IrCl$_2$]$_2$ and N,N'-diphenyloxamide; No Solvent)

A 200 mL autoclave was charged with decane-1,10-diol (20.0 g, 114.8 mmol), hydrotalcite (Mg$_6$Al$_2$(CO$_3$)(OH)$_{16}$.4H$_2$O) (7.0 g, 35 wt % relative to decane-1,10-diol), [Cp*IrCl$_2$]$_2$ (22.9 mg, 1/2000 equivalents calculated as Ir relative to decane-1,10-diol) and N,N'-diphenyloxamide (206.8 mg, 15 equivalents relative to Ir), and then purged with nitrogen. Under a nitrogen stream, acetone (101 mL, 12 equivalents relative to decane-1,10-diol) and isopropyl alcohol (1.75 mL) were introduced into the autoclave, followed by initiation of heating and stirring. After stirring at 155° C. to 160° C. for 5 hours, the autoclave was cooled. The reaction mixture was analyzed by gas chromatography, indicating that 13-hydroxytridecan-2-one (22%) and hexadecane-2,15-dione (60%) were produced (expressed in GC area %). It should be noted that the quantitative yield of hexadecane-2,15-dione was 45%.

[Example 10] Synthesis of Hexadecane-2,15-dione ([Cp*IrCl$_2$]$_2$ and N,N'-di-p-tolyloxamide; No Xylene Solvent)

Example 9 was repeated using N,N'-di-p-tolyloxamide (228.9 mg) instead of N,N'-diphenyloxamide, thus indicating that 13-hydroxytridecan-2-one (41%) and hexadecane-2,15-dione (35%) were produced (expressed in GC area %). It should be noted that the quantitative yield of hexadecane-2,15-dione was 26%.

[Example 11] Synthesis of Hexadecane-2,15-dione (Ir-1; S/C (Substrate/Catalyst Molar Ratio Calculated as Metal Atoms)=5000)

A 200 mL autoclave was charged with decane-1,10-diol (7.08 g, 40.6 mmol), hydrotalcite (Mg$_6$Al$_2$(CO$_3$)(OH)$^{16}$.4H$_2$O) (2.50 g, 35 wt % relative to decane-1,10-diol) and chloro[N-[4-(dimethylamino)phenyl]-2-pyridinecarboxamidato](pentamethyl-cyclopentadienyl)iridium(III) (Ir-1) (5.0 mg, 1/5000 equivalents calculated as Ir relative to decane-1,10-diol), and then purged with nitrogen. Under a nitrogen stream, xylene (50 mL) and acetone (30 mL, relative to decane-1,10-diol) were introduced into the autoclave, followed by initiation of heating and stirring. After stirring at 170° C. to 175° C. for 5 hours, the autoclave was cooled. The reaction mixture was analyzed by gas chromatography, indicating that 13-hydroxytridecan-2-one (3%) and hexadecane-2,15-dione (69%) were produced (expressed in GC area %). It should be noted that the quantitative yield of hexadecane-2,15-dione was 46%.

[Example 12] Synthesis of Hexadecane-2,15-dione (Ir-1; S/C=1000)

Example 11 was repeated to carry out the reaction at a reaction temperature of 155° C. to 160° C. using Ir-1 in an amount of 24.6 mg (1/1000 equivalents calculated as Ir relative to decane-1,10-diol), thus indicating that 13-hydroxytridecan-2-one (10%) and hexadecane-2,15-dione (70%) were produced (expressed in GC area %). It should be noted that the quantitative yield of hexadecane-2,15-dione was 57%.

[Example 13] Synthesis of Hexadecane-2,15-dione (Ir-1; S/C=1000, 12 Hours)

Example 12 was repeated to carry out the reaction for a reaction time of 12 hours, thus indicating that 13-hydroxytridecan-2-one (5%) and hexadecane-2,15-dione (4) (78%) were produced (expressed in GC area %). It should be noted that the quantitative yield of hexadecane-2,15-dione was 62%.

[Reference Example 1] Synthesis of [Cp*$_2$Ir$_2$Cl$_{12}$ (μ-N,N'-di-p-tolyloxamidato)]

[Formula 60]

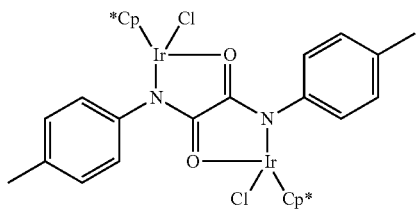

A 20 mL Schlenk tube was charged with N,N'-di-p-tolyloxamide (34.8 mg, 0.130 mmol), [Cp*IrCl$_2$]$_2$ (100.7 mg, 0.252 mmol; calculated as Ir) and potassium carbonate (69.3 mg, 0.253 mmol), and then purged with nitrogen. Acetonitrile (10 mL) was added to the Schlenk tube, followed by heating at 60° C. for 5 hours under stirring to give a yellow solid. After the reaction supernatant was removed with a syringe, the solid was washed with acetonitrile (5 mL) and dried under reduced pressure. Dichloromethane (5 mL) was added to the solid, followed by celite filtration and washing with dichloromethane (5 mL). After distilling off the solvent, the residue was dried under reduced pressure to obtain the titled compound (90.4 mg) as a yellow solid (yield: 72%).

$^1$H-NMR (400 MHz, CDCl$_3$): δ 7.49 (d, J=8.0 Hz, 4H), 7.07 (d, J=8.0 Hz, 4H), 2.34 (s, 6H), 1.33 (s, 30H);

$^{13}$C-NMR (126 MHz, CDCl$_3$): σ 171.81 (C), 142.81 (C), 134.39 (C), 128.33 (CH), 125.96 (CH), 83.95 (C), 21.12 (CH3), 8.59 (CH3);

HRMS (APCI): m/z calc'd for C$_{36}$H$_{44}$ClIr$_2$N$_2$O$_2$ [M-Cl]$^+$ 957.2344; measured 957.2334.

[Reference Example 2] Synthesis of [Cp*$_2$Ir$_2$Cl$_2$(μ-N,N'-diphenyloxamidato)]

[Formula 61]

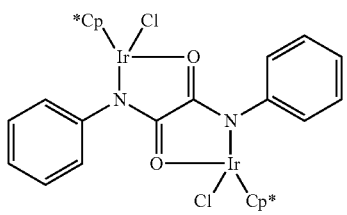

A 20 mL Schlenk tube was charged with N,N'-diphenyloxamide (60.0 mg, 0.250 mmol), [Cp*IrCl$_2$]$_2$ (201.6 mg, 0.506 mmol; calculated as Ir) and potassium carbonate (139.1 mg, 1.01 mmol), and then purged with nitrogen. Acetonitrile (10 mL) was added to the Schlenk tube, followed by heating at 60° C. for 5 hours under stirring to give a yellow solid. After the reaction supernatant was removed with a syringe, the solid was washed twice with acetonitrile (5 mL), three times with distilled water (5 mL) and then with acetonitrile (5 mL). The solid was dried under reduced pressure to obtain the titled compound (113.3 mg) as a yellow solid (yield: 46%).

$^1$H-NMR (500 MHz, CDCl$_3$): 7.65-7.55 (m, 4H), 7.35-7.25 (m, 4H), 7.15-7.05 (m, 2H), 1.33 (s, 30H);

$^{13}$C-NMR (126 MHz, CDCl$_3$): σ 171.87 (C), 145.45 (C), 127.82 (CH), 126.20 (CH), 125.03 (CH), 84.02 (C), 8.57 (CH3);

HRMS (APCI): m/z calc'd for C$_{34}$H$_{40}$ClIr$_2$N$_2$O$_2$ [M]$^+$ 929.2031; measured=929.2019.

[Example 14] Synthesis of [Cp*$_2$Ir$_2$Cl$_2$(μ-N,N'-bis(4-fluorophenyl)oxamidato)]

[Formula 62]

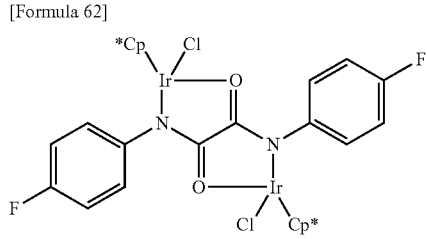

A 20 mL Schlenk tube was charged with N,N'-bis(4-fluorophenyl)oxamide (69.2 mg, 0.250 mmol), [Cp*IrCl$_2$]$_2$ (198.7 mg, 0.499 mmol; calculated as Ir) and potassium carbonate (141.1 mg, 1.02 mmol), and then purged with nitrogen. Acetonitrile (10 mL) was added to the Schlenk tube, followed by heating at 60° C. for 4 hours under stirring to give a yellow solid. After the reaction supernatant was removed with a syringe, the solid was washed twice with acetonitrile (5 mL) and dried under reduced pressure. Dichloromethane (5 mL) was added to the solid, followed by celite filtration and washing with dichloromethane (5 mL). After distilling off the solvent, the residue was dried under reduced pressure to obtain the titled compound (162.9 mg) as a yellow solid (yield: 65%).

1H-NMR (400 MHz, CDCl$_3$): δ 7.65-7.55 (m, 4H), 6.91 (dd, J=8.4 Hz, 4H), 1.35 (s, 30H)

[Example 15] Synthesis of Hexadecane-2,15-dione ([Cp*$_2$Ir$_2$Cl$_2$(μ-N,N'-di-p-tolyloxamidato)]

A 200 mL autoclave was charged with decane-1,10-diol (20.0 g, 114.7 mmol), hydrotalcite (Mg$_6$Al$_2$(CO$_3$)(OH)$_{16}$·4H$_2$O) (7.00 g, 35 wt % relative to decane-1,10-diol) and [Cp*$_2$Ir$_2$Cl$_2$(μ-N,N'-di-p-tolyloxamidato)] synthesized in Reference Example 1 (29.1 mg, about 1/2000 equivalents calculated as Ir relative to decane-1,10-diol), and then purged with nitrogen. Under a nitrogen stream, acetone (101 mL, 12 equivalents relative to decane-1,10-diol) and 2-propanol (1.75 mL, 0.2 equivalents relative to decane-1,10-diol) were introduced into the autoclave, followed by initiation of heating and stirring. After stirring at 155° C. to 160° C. for 5 hours, the autoclave was cooled. The reaction mixture was analyzed by gas chromatography, indicating that 13-hydroxytridecan-2-one (26%) and hexadecane-2,15-dione (4) (52%) were produced (expressed in GC area %). It should be noted that the quantitative yield of hexadecane-2,15-dione was 38%.

[Example 16] Synthesis of Hexadecane-2,15-dione ([Cp*$_2$Ir$_2$Cl$_2$(μ-N,N'-bis(4-fluorophenyl)oxamidato)])

Under the same conditions as used in Example 15, [Cp*$_2$Ir$_2$Cl$_2$(μ-N,N'-bis(4-fluorophenyl)oxamidato)] synthesized in Example 14 (34.3 mg, about 1/1670 equivalents calculated as Ir relative to decane-1,10-diol) was used instead of [Cp*$_2$Ir$_2$Cl$_2$(μ-N,N'-di-p-tolyloxamidato)]. The reaction mixture was analyzed by gas chromatography, indicating that 13-hydroxytridecan-2-one (25%) and hexadecane-2,15-dione (4) (52%) were produced (expressed in GC area %). It should be noted that the quantitative yield of hexadecane-2,15-dione was 38%.

[Example 17] Synthesis of [Cp*IrCl(N-2,3,4,5,6-pentafluoro-N-phenyl-benzamidato)] (A) (Synthesis of a Mixture Containing Compound (A) as a Major Component)

A 20 mL Schlenk tube was charged with N-2,3,4,5,6-pentafluoro-N-phenylbenzamide (L$^4$) (72.6 mg, 0.252 mmol), [Cp*IrCl$_2$]$_2$ (100.0 mg, 0.251 mmol; calculated as Ir) and potassium carbonate (33.0 mg, 0.239 mmol), and then purged with nitrogen. Acetonitrile (10 mL) was added to the Schlenk tube, followed by stirring at 30° C. for 4 hours. After distilling off the acetonitrile, the residue was diluted with dichloromethane (5 mL), followed by celite filtration and further washing with dichloromethane (5 mL). The filtrate was concentrated to obtain a mixture of (A), (B), [Cp*IrCl$_2$]$_2$ and L$^4$ (161.3 mg). $^{19}$FNMR analysis indicated that the ratio of (A)+(B) to (L$^4$) was 79:21, and $^1$HNMR analysis indicated that the ratio of (A):(B):[Cp*IrCl$_2$]$_2$ was 54:11:35 (calculated as Ir).

[Formula 63]

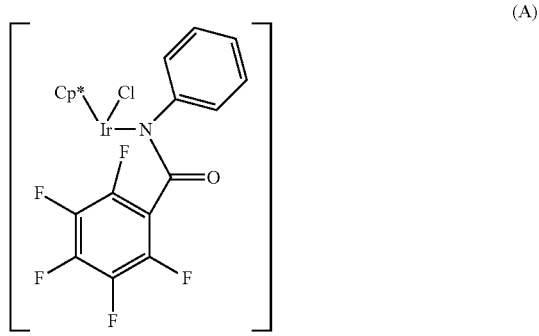

(A)

$^1$H-NMR (400 MHz, CDCl$_3$): δ 7.21 (dd, J=7.2, 7.2 Hz, 2H), 7.25-7.15 (m, 1H), 7.00 (d, J=7.2 Hz, 2H), 1.66 (s, 15H)

$^{19}$F-NMR (376 MHz, CDCl$_3$): δ −139.55 (d, 2F), −152.58 (t, 1F), −162.33 (dd, 2F)

[Formula 64]

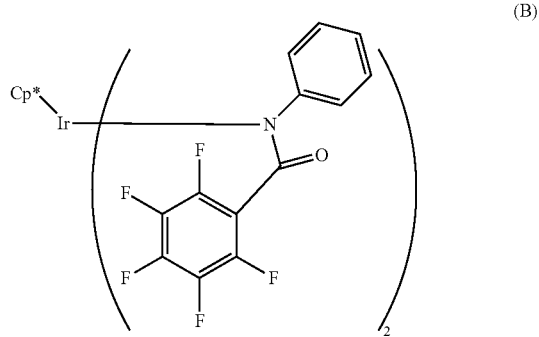

(B)

$^1$H-NMR (400 MHz, CDCl$_3$): δ 7.15-7.05 (m, 4H), 7.05-6.95 (m, 2H), 6.92 (d, J=8.0 Hz, 4H), 1.64 (s, 15H)

$^{19}$F-NMR (376 MHz, CDCl$_3$): δ −149.89 (d, 4F), −155.20 (t, 2F), −163.05 (dd, 4F)

[Example 18] Synthesis of [Cp*Irbis(N-2,3,4,5,6-pentafluoro-N-phenyl-benzamidato)] (B) (Synthesis of a Mixture Containing Compound (B) as a Major Component)

A 20 mL Schlenk tube was charged with N-2,3,4,5,6-pentafluoro-N-phenylbenzamide (L$^4$) (143 mg, 0.499 mmol), [Cp*IrCl$_2$]$_2$ (100 mg, 0.251 mmol; calculated as Ir) and potassium carbonate (69.7 mg, 0.504 mmol), and then purged with nitrogen. Acetonitrile (10 mL) was added to the Schlenk tube, followed by stirring at 30° C. for 8 hours. After distilling off the solvent, the residue was diluted with dichloromethane (5 mL), followed by celite filtration and further washing with dichloromethane (5 mL). The filtrate was concentrated to obtain a black solid. Then, dichloromethane (1 mL) and hexane (5 mL) were added to the resulting black solid, and the mixture was stirred, allowed to stand overnight and then filtered. The filtrate was concentrated and dried to obtain a mixture of (B) and (L$^4$) (230 mg). $^{19}$FNMR analysis indicated that the molar ratio of (B) to (L$^4$) was 88:12.

Example 19

Under the same conditions as used in Example 15, the catalyst mixture synthesized in Example 17 (36.7 mg) was used instead of [Cp*$_2$Ir$_2$Cl$_2$(μ-N,N'-di-p-tolyloxamidato)]. The reaction mixture was analyzed by gas chromatography, indicating that 13-hydroxytridecan-2-one (48%) and hexadecane-2,15-dione (4) (5%) were produced (expressed in GC area %).

Example 20

Under the same conditions as used in Example 15, the catalyst mixture synthesized in Example 18 (57.4 mg) was used instead of [Cp*$_2$Ir$_2$Cl$_2$(μ-N,N'-di-p-tolyloxamidato)]. The reaction mixture was analyzed by gas chromatography, indicating that 13-hydroxytridecan-2-one (48%) and hexadecane-2,15-dione (4) (17%) were produced (expressed in GC area %).

[Example 21, Comparative Examples 1 to 4] Comparison Between Hydrotalcite and Solid Bases A 100 mL autoclave was charged with decane-1,10-diol (2.4 g, 13.8 mmol), hydrotalcite (Mg$_6$Al$_2$(CO$_3$)(OH)$_{16}$.4H$_2$O) or a solid base (0.84 g, 35 wt % relative to decane-1,10-diol) and Ir-1 (1.7 mg, 1/5000 equivalents calculated as Ir relative to decane-1,10-diol), and then purged with nitrogen. Under a nitrogen stream, xylene (17 mL) and acetone (10.1 mL, 10 equivalents relative to decane-1,10-diol) were introduced into the autoclave, followed by initiation of heating and stirring. After stirring at 160° C. for 5 hours, the autoclave was cooled. The reaction mixture was analyzed by gas chromatography to determine the quantitative yield.

TABLE 1

| | Hydrotalcite or solid base | Quantitative yield of hexadecane-2,15-dione |
|---|---|---|
| Example 21 | Hydrotalcite | 21 |
| Comparative Example 1 | Potassium carbonate | 0 |
| Comparative Example 2 | Magnesium hydroxide | 1 |
| Comparative Example 3 | Aluminum hydroxide | 0 |
| Comparative Example 4 | Zirconium hydroxide | 0 |

[Comparative Example 5] Reaction Using KOH as a Base

A 100 mL autoclave was charged with decane-1,10-diol (2.4 g, 13.8 mmol), Ir-1 (1.7 mg, 1/5000 equivalents calculated as Ir relative to decane-1,10-diol) and potassium hydroxide (3.1 mg, 20 equivalents relative to Ir), and then purged with nitrogen. Under a nitrogen stream, xylene (17 mL) and acetone (10.1 mL, 10 equivalents relative to decane-1,10-diol) were introduced into the autoclave, followed by initiation of heating and stirring. After stirring at 160° C. for 5 hours, the autoclave was cooled. The reaction mixture was analyzed by gas chromatography, indicating that the quantitative yield of hexadecane-2,15-dione was 1%.

[Comparative Example 6] Reaction Using Ir/HT

A 100 mL autoclave was charged with decane-1,10-diol (2.4 g, 13.8 mmol) and 0.2 wt % Ir/HT (a solid obtained such that iridium chloride and hydrotalcite were mixed in water until the aqueous phase became transparent, followed by filtration and drying) (1.32 g, 1/1000 equivalents calculated as Ir relative to decane-1,10-diol), and then purged with nitrogen. Under a nitrogen stream, xylene (17 mL) and acetone (10.1 mL, 10 equivalents relative to decane-1,10-diol) were introduced into the autoclave, followed by initiation of heating and stirring. After stirring at 160° C. for 5 hours, the autoclave was cooled. The reaction mixture was analyzed by gas chromatography, indicating that hexadecane-2,15-dione was not produced.

[Example 22] Synthesis of 1,3-diphenyl-propan-1-one

[Formula 65]

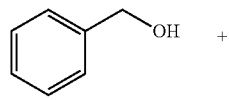

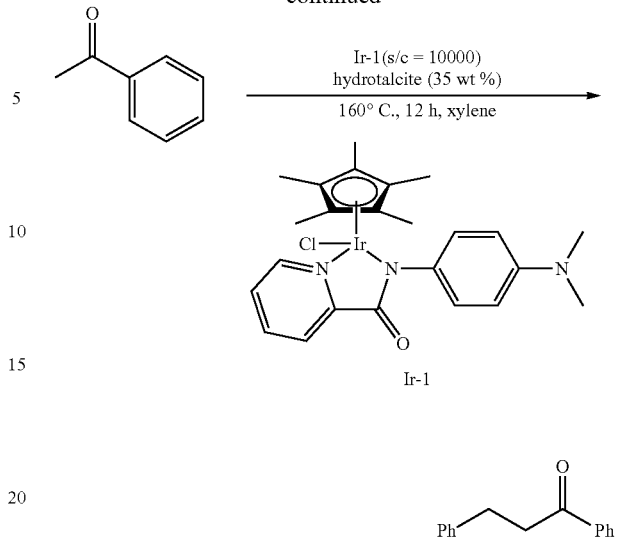

A 100 mL Schlenk tube equipped with a Dimroth condenser was charged with hydrotalcite ($Mg_6Al_2(CO_3)(OH)_{16} \cdot 4H_2O$) (910 mg) and Ir-1 (1.5 mg, 0.0025 mmol), and then purged with nitrogen, followed by addition of benzyl alcohol (2.6 mL, 25 mmol), acetophenone (3.0 mL, 25 mmol) and xylene (18 mL). The mixture was heated under reflux at 160° C. for 12 hours. After cooling, the reaction mixture was filtered and concentrated. The residue was purified by silica gel column chromatography to obtain 1,3-diphenyl-propan-1-one (4.5 g, yield: 86%).

$^1$H-NMR (400 MHz, $CDCl_3$): δ 7.96 (d, J=7.1 Hz, 2H), 7.56 (t, J=7.4 Hz, 1H), 7.47 (t, J=7.6 Hz, 2H), 7.32-7.20 (m, 5H), 3.32 (t, J=7.7 Hz, 2H), 3.07 (t, J=7.7 Hz, 2H)

[Comparative Example 7] Synthesis of 1,3-diphenyl-propan-1-one ([Cp*IrCl$_2$]$_2$; Sodium Bicarbonate)

A 100 mL Schlenk tube equipped with a Dimroth condenser was charged with sodium bicarbonate (36 mg, 0.04 mmol) and [Cp*IrCl$_2$]$_2$ (4.0 mg, 0.01 mmol; calculated as Ir), and then purged with nitrogen, followed by addition of benzyl alcohol (2.1 mL, 20 mmol), acetophenone (2.4 mL, 20 mmol) and xylene (14 mL). The mixture was heated under reflux at 160° C. for 5 hours. After cooling, the reaction mixture was filtered and analyzed by GC, indicating that the desired product was not produced.

[Comparative Example 8] Synthesis of 1,3-diphenyl-propan-1-one (Ir-1; Sodium Bicarbonate)

A 100 mL Schlenk tube equipped with a Dimroth condenser was charged with sodium bicarbonate (36 mg, 0.04 mmol) and Ir-1 (3.0 mg, 0.005 mmol), and then purged with nitrogen, followed by addition of benzyl alcohol (2.1 mL, 20 mmol), acetophenone (2.4 mL, 20 mmol) and xylene (14 mL). The mixture was heated under reflux at 160° C. for 5 hours. After cooling, the reaction mixture was filtered and analyzed by GC, indicating that the desired product was not produced.

[Example 23] Synthesis of 1-phenyl-octan-1-one

[Formula 66]

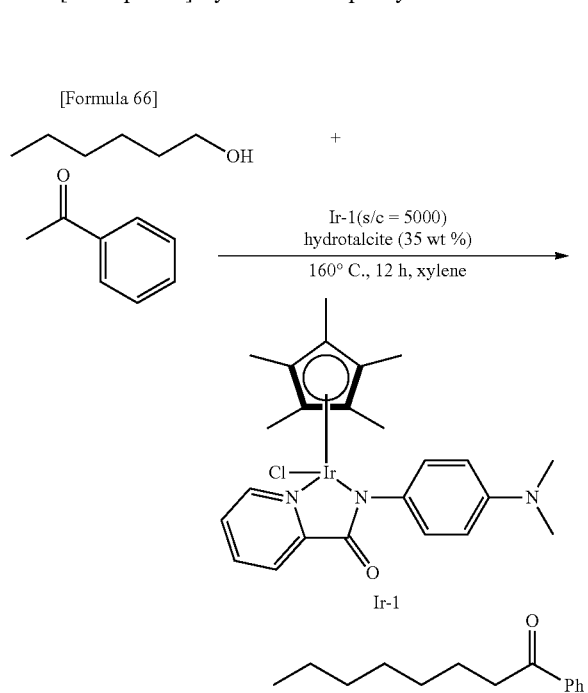

A 100 mL Schlenk tube equipped with a Dimroth condenser was charged with hydrotalcite ($Mg_6Al_2(CO_3)(OH)_{16} \cdot 4H_2O$) (1.4 g) and Ir-1 (4.8 mg, 0.008 mmol), and then purged with nitrogen, followed by addition of 1-hexanol (5.0 mL, 40 mmol), acetophenone (4.8 mL, 40 mmol) and xylene (28 mL). The mixture was heated under reflux at 160° C. for 12 hours. After cooling, the reaction mixture was filtered and concentrated. The residue was purified by silica gel column chromatography to obtain 1-phenyl-octan-1-one (6.3 g, yield: 77%).

$^1$H-NMR (400 MHz, $CDCl_3$): δ 7.96 (d, J=7.1 Hz, 2H), 7.55 (t, J=7.4 Hz, 1H), 7.45 (t, J=7.4 Hz, 2H), 2.96 (t, J=7.6 Hz, 2H), 1.75-1.70 (m, 2H), 1.40-1.28 (m, 8H), 0.88 (t, J=7.0 Hz, 3H)

[Comparative Example 9] Synthesis of 1-phenyl-octan-1-one ([Cp*IrCl$_2$]$_2$; Sodium Bicarbonate)

A 100 mL Schlenk tube equipped with a Dimroth condenser was charged with sodium bicarbonate (36 mg, 0.04 mmol) and [Cp*IrCl$_2$]$_2$ (3.3 mg, 0.0066 mmol; calculated as Ir), and then purged with nitrogen, followed by addition of 1-hexanol (2.5 mL, 20 mmol), acetophenone (2.4 mL, 20 mmol) and xylene (14 mL). The mixture was heated under reflux at 160° C. for 5 hours. After cooling, the reaction mixture was filtered and analyzed by GC, indicating that the desired product was not produced.

[Example 24] Synthesis of 1-phenyl-tridecan-1-one

[Formula 67]

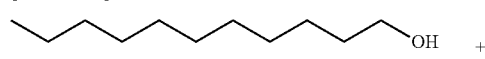

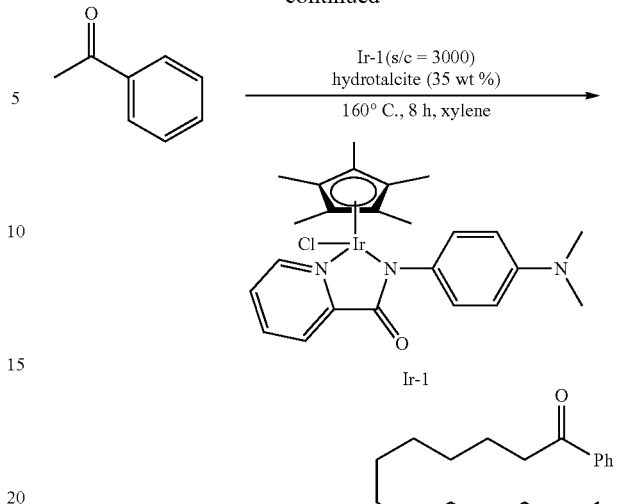

A 100 mL Schlenk tube equipped with a Dimroth condenser was charged with hydrotalcite ($Mg_6Al_2(CO_3)(OH)_{16} \cdot 4H_2O$) (1.2 g) and Ir-1 (4.0 mg, 0.0067 mmol), and then purged with nitrogen, followed by addition of 1-dodecanol (4.1 mL, 20 mmol), acetophenone (2.4 mL, 20 mmol) and xylene (24 mL). The mixture was heated under reflux at 160° C. for 8 hours. After cooling, the reaction mixture was filtered and concentrated. The residue was purified by silica gel column chromatography to obtain 1-phenyl-tridecan-1-one (4.4 g, yield: 80%).

$^1$H-NMR (400 MHz, $CDCl_3$): δ 7.87 (d, J=7.2 Hz, 2H), 7.45 (t, J=7.4 Hz, 1H), 7.35 (t, J=7.5 Hz, 2H), 2.86 (t, J=7.6 Hz, 2H), 1.71-1.04 (m, 18H), 0.79 (t, J=6.7 Hz, 3H)

[Comparative Example 10] Synthesis of 1-phenyl-tridecan-1-one ([Cp*IrCl$_2$]$_2$; Sodium Bicarbonate)

A 100 mL Schlenk tube equipped with a Dimroth condenser was charged with sodium bicarbonate (36 mg, 0.04 mmol) and [Cp*IrCl$_2$]$_2$ (3.3 mg, 0.0066 mmol; calculated as Ir), and then purged with nitrogen, followed by addition of 1-dodecanol (4.1 mL, 20 mmol), acetophenone (2.4 mL, 20 mmol) and xylene (14 mL). The mixture was heated under reflux at 160° C. for 5 hours. After cooling, the reaction mixture was filtered and analyzed by GC, indicating that the desired product was not produced.

[Example 25] Synthesis of tetradecan-2-one

A 200 ml mechanical autoclave was charged with hydrotalcite ($Mg_6Al_2(CO_3)(OH)_{16} \cdot 4H_2O$) (4.8 g) and Ir-1 (9.6 mg, 0.016 mmol), and then purged with nitrogen, followed by addition of 1-decanol (16.8 ml, 80 mmol), acetone (29.3 ml, 400 mmol) and xylene (130 ml). The mixture was reacted at 160° C. for 5 hours. After cooling, the reaction mixture was measured by gas chromatography, indicating that tridecan-2-one (76%) was obtained (expressed in GC area %).

[Example 26] Synthesis of N-benzylpyrrolidine

A 100 mL autoclave was charged with hydrotalcite ($Mg_6Al_2(CO_3)(OH)_{16} \cdot 4H_2O$) (63 mg) and [Cp*IrCl$_2$]$_2$ (40 mg, 0.10 mmol; calculated as Ir), and then purged with nitrogen, followed by addition of 1,4-butanediol (180, 2 mmol) and benzylamine (214 d, 2 mmol). The mixture was reacted at 160° C. for 5 hours. After cooling, the reaction mixture was filtered and concentrated. The residue was purified by silica gel column chromatography to obtain N-benzylpyrrolidine (82 mg, yield: 25%).

$^1$H-NMR (400 MHz, CDCl$_3$): δ 7.34-7.20 (m, 5H), 3.61 (s, 2H), 2.53-2.49 (m, 4H), 1.79-1.76 (m, 4H)

[Reference Example 3] Synthesis of N,N'-bis(5-tert-butyl-2-methylphenyl)-oxamide

[Formula 68]

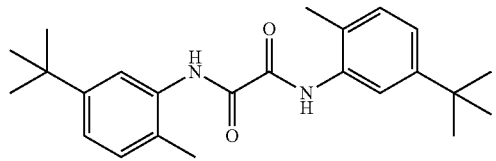

Under a nitrogen stream, a 300 mL three-necked flask equipped with a dropping funnel was charged with tetramethylammonium nitrate (1.48 g, 10.9 mmol) and dichloromethane (25 mL), followed by stirring at room temperature. Triflic anhydride (3.14 g, 11.1 mmol) was added dropwise, followed by washing with dichloromethane (10 mL). After the reaction mixture was cooled in a dry ice-acetone bath, a solution of 4-(tert-butyl)toluene (1.48 g, 9.98 mmol) in dichloromethane (15 mL) was added dropwise thereto while keeping the reaction mixture at −65° C. or less. The reaction mixture was stirred for 3 hours while gradually warming to room temperature. After 5% aqueous sodium bicarbonate (15 mL) was added to partition the reaction mixture, the dichloromethane layer was washed twice with water (25 mL). The dichloromethane layer was dried over anhydrous sodium sulfate and the solvent was then distilled off to obtain 4-tert-butyl-1-methyl-2-nitrobenzene (1.77 g, yield: 92%).

$^1$H-NMR (400 MHz, CDCl$_3$): σ=7.97 (s, 1H), 7.52 (d, J=8.0 Hz, 1H), 7.30-7.20 (m, 1H), 2.56 (s, 3H), 1.34 (s, 9H).

Into a 300 mL three-necked flask, 4-(tert-butyl)-1-methyl-2-nitrobenzene (1.77 g, 9.16 mmol) was introduced and diluted with methanol (40 mL), followed by addition of 10% Pd/C (174 mg). The container was purged with hydrogen and the mixture was stirred at 30° C. for 3 hours. The reaction mixture was filtered through celite and the celite was washed with methanol (10 mL), and the filtrate was then concentrated to obtain 5-tert-butyl-2-methylaniline (1.48 g, yield: 99%).

$^1$H-NMR (400 MHz, CDCl$_3$): σ=6.98 (d, J=8.0 Hz, 1H), 6.75 (dd, J=2.0, 8.0 Hz, 1H), 6.72 (d, J=2.0 Hz, 1H), 2.13 (s, 3H), 1.28 (s, 9H).

Under a nitrogen stream, a 300 mL three-necked flask equipped with a dropping funnel was charged with 5-(tert-butyl)-2-methylaniline (1.48 g, 9.1 mmol), THF (40 mL) and triethylamine (1.2 mL, 8.6 mmol), and then cooled to 5° C. to 10° C. in an ice bath. After a solution of oxalyl chloride (0.35 mL, 4.1 mmol) in THF (10 mL) was added dropwise to the flask, the mixture was stirred at room temperature for 4 hours. The resulting red to pink suspension was filtered and the cake was washed with THF (10 mL). After the filtrate was concentrated, the residue was diluted with methanol (25 mL) and then shaken. After the solid was collected by filtration, the solid was washed with methanol (10 mL) and dried under reduced pressure to obtain the titled compound (1.08 g) as a white to pale opalescent solid (yield: 69%).

$^1$H-NMR (500 MHz, CDCl$_3$): σ=9.37 (s, 2H), 8.17 (s, 2H), 7.20-7.15 (m, 4H), 2.35 (s, 6H), 1.35 (s, 18H);

$^{13}$C-NMR (126 MHz, CDCl$_3$): σ=157.70 (C), 150.32 (C), 134.11 (C), 130.31 (CH), 125.48 (C), 122.79 (CH), 118.43 (CH), 34.65 (C), 31.32 (CH3), 16.98 (CH3);

HRMS (APPI (Pos.)): m/z calc'd for C$_{24}$H$_{32}$N$_2$O$_2$ [M+H]$^+$ 381.2537; measured=381.2534.

[Reference Example 4] Synthesis of N,N'-bis(2-methylphenyl)oxamide

[Formula 69]

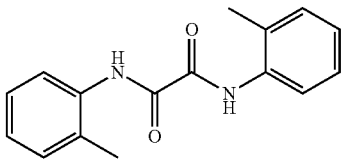

Under a nitrogen stream, a 500 mL three-necked flask equipped with a dropping funnel was charged with 2-methylaniline (2.36 g, 22.0 mmol), THE (200 mL) and triethylamine (2.9 mL, 20.9 mmol), and then cooled to 5° C. to 10° C. in an ice bath. After a solution of oxalyl chloride (0.86 mL, 10.0 mmol) in THE (50 mL) was added dropwise to the flask, the mixture was stirred at room temperature for 5 hours. The resulting white suspension was filtered. After the filtrate was concentrated, the residue was diluted with methanol (20 mL) and then shaken. After the solid was collected by filtration, the solid was washed twice with methanol (10 mL) and dried under reduced pressure to obtain the titled compound (1.91 g) as a white solid (yield: 71%).

$^1$H-NMR (500 MHz, CDCl$_3$): σ=9.37 (s, 2H), 8.10 (d, J=7.9 Hz, 2H), 7.32-7.25 (m, 4H), 7.15 (dd, J=6.5, 7.5 Hz, 2H), 2.39 (s, 6H); $^{13}$C-NMR (126 MHz, CDCl$_3$): 157.65 (C), 134.35 (C), 130.73 (CH), 128.43 (C), 127.02 (CH), 125.84 (CH), 121.22 (CH), 17.46 (CH3); HRMS (APPI (Pos.)): m/z calc'd for C$_{16}$H$_{16}$N$_2$O$_2$ [M]$^+$ 268.1206; measured=268.1200.

[Reference Example 5] Synthesis of N,N'-bis(3-methylphenyl)oxamide

[Formula 70]

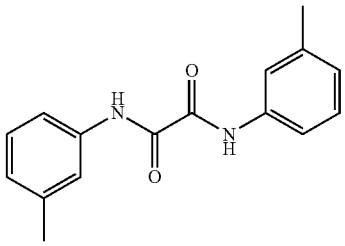

Under a nitrogen stream, a 500 mL three-necked flask equipped with a dropping funnel was charged with 3-methylaniline (2.34 g, 21.9 mmol), THF (200 mL) and triethylamine (2.9 mL, 20.9 mmol), and then cooled to 5° C. to 10° C. in an ice bath. After a solution of oxalyl chloride (0.86 mL, 10.0 mmol) in THE (50 mL) was added dropwise to the flask, the mixture was stirred at room temperature for 3 hours. The resulting white suspension was filtered and the cake was washed with a small volume of THE. After the filtrate was concentrated, the residue was diluted with methanol (20 mL) and then shaken. After the solid was collected by filtration, the solid was washed twice with methanol (10 mL) and dried under reduced pressure to obtain the titled compound (1.93 g) as a white solid (yield: 72%).

$^1$H-NMR (500 MHz, CDCl$_3$): 9.30 (s, 2H), 7.55-7.45 (m, 4H), 7.35-7.25 (m, 2H), 7.03 (d, J=7.6 Hz, 2H), 2.39 (s, 6H);

$^{13}$C-NMR (126 MHz, CDCl$_3$): 157.48 (C), 139.29 (C), 136.12 (C), 129.10 (CH), 126.38 (CH), 120.40 (CH), 116.93 (CH), 21.49 (CH3);

HRMS (APPI (Pos.)): m/z calc'd for $C_{16}H_{16}N_2O_2$ [M]$^+$ 268.1206; measured=268.1207.

[Reference Example 6] Synthesis of N,N'-bis(2,3-dimethylphenyl)oxamide

[Formula 71]

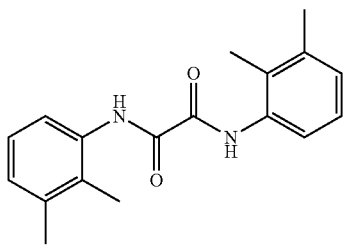

Under a nitrogen stream, a 500 mL three-necked flask equipped with a dropping funnel was charged with 2,3-dimethylaniline (2.7 mL, 22.2 mmol), THE (100 mL) and triethylamine (2.9 mL, 20.9 mmol), and then cooled to 5° C. to 10° C. in an ice bath. After a solution of oxalyl chloride (0.86 mL, 10.0 mmol) in THF (25 mL) was added dropwise to the flask, the mixture was stirred at room temperature for 4 hours. The resulting white suspension was filtered and the cake was washed with THE (10 mL). The solid collected by filtration was mixed with methanol (50 mL) and then shaken. After the solid was collected by filtration, the solid was washed with methanol (10 mL) and dried under reduced pressure to obtain the titled compound (2.45 g) as a white solid (yield: 83%).

$^1$H-NMR (500 MHz, CDCl$_3$): σ=9.37 (s, 2H), 7.82 (d, J=8.1 Hz, 2H), 7.18 (dd, J=7.5, 8.1 Hz, 2H), 7.07 (d, J=7.5 Hz, 2H), 2.34 (s, 6H), 2.26 (s, 6H);

$^{13}$C-NMR (126 MHz, CDCl$_3$): σ=157.94 (C), 137.68 (C), 134.07 (C), 127.98 (C), 127.81 (CH), 126.16 (CH), 119.94 (CH), 20.61 (CH3), 13.43 (CH3);

HRMS (APPI (Pos.)): m/z calc'd for $C_{18}H_{21}N_2O_2$ [M+H]$_+$ 297.1598; measured=297.1592.

[Reference Example 7] Synthesis of N,N'-bis(2,4-dimethylphenyl)oxamide

[Formula 72]

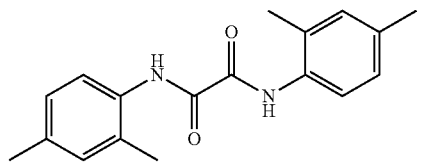

Under a nitrogen stream, a 500 mL three-necked flask equipped with a dropping funnel was charged with 2,4-dimethylaniline (2.7 mL, 21.6 mmol), THE (100 mL) and triethylamine (2.9 mL, 20.9 mmol), and then cooled to 5° C. to 10° C. in an ice bath. After a solution of oxalyl chloride (0.86 mL, 10.0 mmol) in THE (30 mL) was added dropwise to the flask, the mixture was stirred at room temperature for 3 hours. The resulting white suspension was filtered. The solid collected by filtration was mixed with methanol (50 mL) and then shaken. After the solid was collected by filtration, the solid was washed twice with methanol (10 mL) and dried under reduced pressure to obtain the titled compound (1.47 g) as a white solid (yield: 50%).

$^1$H-NMR (500 MHz, CDCl$_3$): σ=9.29 (s, 2H), 7.93 (d, J=8.2 Hz, 2H), 7.08 (d, J=8.2 Hz, 2H), 7.06 (s, 2H), 2.34 (s, 6H), 2.33 (s, 6H);

$^{13}$C-NMR (126 MHz, CDCl$_3$): σ=157.69 (C), 135.61 (C), 131.82 (C), 131.39 (CH), 128.52 (C), 127.50 (CH), 121.34 (CH), 20.95 (CH3), 17.43 (CH3);

HRMS (APPI (Pos.)): m/z calc'd for $C_{18}H_{20}N_2O_2$ [M]$^+$ 297.1519; measured=297.1518.

[Reference Example 8] Synthesis of N,N'-bis(2,5-dimethylphenyl)oxamide

[Formula 73]

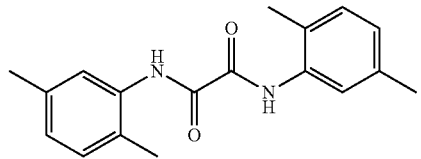

Under a nitrogen stream, a 500 mL three-necked flask equipped with a dropping funnel was charged with 2,4-dimethylaniline (2.8 mL, 21.6 mmol), THF (100 mL) and triethylamine (2.9 mL, 20.9 mmol), and then cooled to 5° C. to 10° C. in an ice bath. After a solution of oxalyl chloride (0.86 mL, 10.0 mmol) in THF (25 mL) was added dropwise to the flask, the mixture was stirred at room temperature for 4.5 hours. The resulting white suspension was filtered and the cake was washed with THF (10 mL). The solid collected by filtration was mixed with methanol (50 mL) and then shaken. After the solid was collected by filtration, the solid was washed with methanol (10 mL) and dried under reduced pressure to obtain the titled compound (1.62 g) as a white solid (yield: 54%).

$^1$H-NMR (500 MHz, CDCl$_3$): σ=9.34 (s, 2H), 7.94 (s, 2H), 7.12 (d, J=7.7 Hz, 2H), 6.96 (d, J=7.7 Hz, 2H), 2.37 (s, 6H), 2.34 (s, 6H);

$^{13}$C-NMR (126 MHz, CDCl$_3$): σ=157.63 (C), 136.89 (C), 134.17 (C), 130.51 (CH), 126.59 (CH), 125.19 (C), 121.65 (CH), 21.23 (CH3), 17.00 (CH3);

HRMS (APPI (Pos.)): m/z calc'd for C$_{18}$H$_{21}$N$_2$O$_2$ [M+H]$^+$ 297.1598; measured=297.151887.

[Reference Example 9] Synthesis of N,N'-bis(2-methylphenyl)oxamide

[Formula 74]

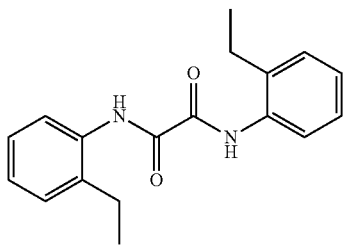

Under a nitrogen stream, a 500 mL three-necked flask equipped with a dropping funnel was charged with 2-ethylaniline (2.75 mL, 22.0 mmol), THF (100 mL) and triethylamine (2.9 mL, 20.9 mmol), and then cooled to 5° C. to 10° C. in an ice bath. After a solution of oxalyl chloride (0.86 mL, 10.0 mmol) in THF (25 mL) was added dropwise to the flask, the mixture was stirred at room temperature for 4 hours. The resulting white suspension was filtered and the cake was washed with THF. After the filtrate was concentrated, the residue was diluted with methanol (50 mL) and then shaken. After the solid was collected by filtration, the solid was washed with methanol (20 mL) and dried under reduced pressure to obtain the titled compound (2.52 g) as a white solid (yield: 85%).

$^1$H-NMR (500 MHz, CDCl$_3$): σ=9.46 (s, 2H), 8.13 (d, J=8.1 Hz, 2H), 7.35-7.25 (m, 4H), 7.19 (ddd, J=1.1, 7.5, 7.5 Hz, 2H), 2.74 (q, J=7.6 Hz, 4H), 1.31 (t, J=7.6 Hz, 6H);

$^{13}$C-NMR (126 MHz, CDCl$_3$): σ=157.75 (C), 134.24 (C), 133.71 (C), 128.92 (CH), 126.94 (CH), 126.04 (CH), 121.45 (CH), 24.28 (CH2), 13.97 (CH3);

HRMS (APCI (Pos.)): m/z calc'd for C$_{18}$H$_{21}$N$_2$O$_2$ [M+H]$^+$ 297.1598; measured=297.1596.

[Reference Example 10] Synthesis of N,N'-bis(5-isopropyl-2-methylphenyl)-oxamide

[Formula 75]

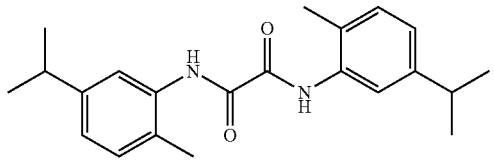

Under a nitrogen stream, a 200 mL three-necked flask equipped with a dropping funnel was charged with 5-isopropyl-2-methylaniline (1.0 mL, 6.4 mmol), THF (30 mL) and triethylamine (0.85 mL, 6.1 mmol), and then cooled to 5° C. to 10° C. in an ice bath. After a solution of oxalyl chloride (0.25 mL, 2.9 mmol) in THF (10 mL) was added dropwise to the flask, the mixture was stirred at room temperature for 4 hours. The resulting suspension was filtered and the cake was washed with THF (10 mL). After the filtrate was concentrated, the residue was diluted with methanol (30 mL) and then shaken. After the solid was collected by filtration, the solid was washed with methanol (10 mL) and dried under reduced pressure to obtain the titled compound (813 mg) as a white solid (yield: 80%).

$^1$H-NMR (500 MHz, CDCl$_3$): σ=9.37 (s, 2H), 8.02 (d, J=1.6 Hz, 2H), 7.17 (d, J=7.8 Hz, 2H), 7.02 (dd, J=1.6, 7.8 Hz, 2H), 2.93 (sept, J=6.9 Hz, 2H), 2.35 (s, 6H), 1.27 (d, J=6.9 Hz, 12H);

$^{13}$C-NMR (126 MHz, CDCl$_3$): σ=157.64 (C), 148.04 (C), 134.28 (C), 130.58 (CH), 125.61 (C), 123.80 (CH), 119.24 (CH), 33.91 (CH), 23.97 (CH3), 17.04 (CH3);

HRMS (APPI (Pos.)): m/z calc'd for C$_{22}$H$_{29}$N$_2$O$_2$ [M+H]$^+$ 353.2224; measured=353.2217.

[Reference Example 11] Synthesis of N,N'-bis(5-(adamantan-1-yl)-2-methyl-phenyl)oxamide

[Formula 76]

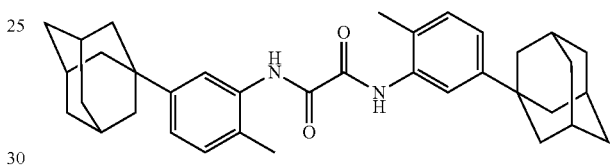

Under a nitrogen stream, a 300 mL three-necked flask equipped with a dropping funnel was charged with tetramethylammonium nitrate (1.43 g, 10.5 mmol) and dichloromethane (25 mL), followed by stirring at room temperature. Triflic anhydride (3.10 g, 11.0 mmol) was added dropwise, followed by washing with dichloromethane (10 mL). After the reaction mixture was cooled in a dry ice-acetone bath, a solution of 4-(adamantan-1-yl)toluene (2.26 g, 9.99 mmol) in dichloromethane (15 mL) was added dropwise thereto while keeping the reaction mixture at −65° C. or less. The reaction mixture was stirred for 2.5 hours while gradually warming to room temperature. After 5% aqueous sodium bicarbonate (25 mL) was added to partition the reaction mixture, the dichloromethane layer was washed twice with water (25 mL). The dichloromethane layer was dried over anhydrous sodium sulfate and the solvent was then distilled off to obtain 1-(4-methyl-3-nitrophenyl)adamantine (2.58 g, yield: 95%).

$^1$H-NMR (400 MHz, CDCl$_3$): σ=7.94 (d, J=2.0 Hz, 1H), 7.49 (dd, J=2.0, 8.4 Hz, 1H), 7.27 (d, J=8.4 Hz, 1H), 2.56 (s, 3H), 2.15-2.05 (m, 3H), 1.95-1.85 (m, 6H), 1.85-1.70 (6H).

Into a 500 mL three-necked flask, 1-(4-methyl-3-nitrophenyl)adamantine (2.58 g, 9.50 mmol) was introduced and diluted with ethanol (40 mL), followed by addition of 10% Pd/C (260 mg). The container was purged with hydrogen and the mixture was stirred at room temperature for 5 hours. After the reaction mixture was filtered through celite, the filtrate was concentrated and purified by silica gel chromatography (eluent: toluene) to obtain 5-(adamantan-1-yl)-2-methylaniline (1.36 g, yield: 59%).

$^1$H-NMR (400 MHz, CDCl$_3$): σ=7.00 (d, J=8.0 Hz, 1H), 6.73 (dd, J=1.6, 8.0 Hz, 1H), 6.69 (d, J=1.6 Hz, 1H), 3.56 (s, 2H), 2.14 (s, 3H), 2.10-2.00 (m, 3H), 1.90-1.85 (m, 6H), 1.80-1.70 (m, 6H).

Under a nitrogen stream, a 300 mL three-necked flask equipped with a dropping funnel was charged with 5-(adamantan-1-yl)-2-methylaniline (1.36 g, 5.6 mmol), THF (30 mL) and triethylamine (0.75 mL, 5.4 mmol), and then cooled to 5° C. to 10° C. in an ice bath. After a solution of oxalyl chloride (0.22 mL, 2.57 mmol) in THF (10 mL) was added dropwise to the flask, the mixture was stirred at room temperature for 4 hours. The resulting suspension was filtered and the cake was washed with THF. The solid collected by filtration was mixed with methanol (20 mL) and then shaken. After the solid was collected by filtration, the solid was washed with methanol (10 mL) and dried under reduced pressure to obtain the titled compound (868 mg) as a white solid (yield: 63%).

$^1$H-NMR (500 MHz, CDCl$_3$): σ=9.39 (s, 2H), 8.16 (d, J=1.9 Hz, 2H), 7.19 (d, J=8.1 Hz, 2H), 7.15 (dd, J=1.9 Hz, 8.1 Hz, 2H), 2.35 (s, 6H), 2.15-2.05 (m, 6H), 2.00-1.90 (m, 12H), 1.85-1.75 (m, 12H);

$^{13}$C-NMR (126 MHz, CDCl$_3$): σ=157.70 (C), 150.64 (C), 134.23 (C), 130.35 (CH), 125.40 (C), 122.37 (CH), 117.93 (CH), 43.23 (CH2), 36.86 (CH2), 36.15 (C), 28.99 (CH), 17.00 (CH3);

HRMS (APPI (Pos.)): m/z calc'd for C$_{36}$H$_{45}$N$_2$O$_2$ [M+H]$^+$ 537.3476; measured=537.3466.

[Example 27] Synthesis of [Cp*$_2$Ir$_2$Cl$_2$(μ-N,N'-bis (5-tert-butyl-2-methyl-phenyl)oxamidato)] (Ir-2)

[Formula 77]

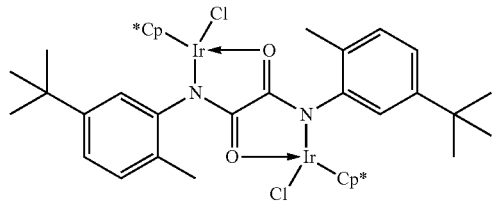

A 20 mL Schlenk tube was charged with N,N'-bis(5-tert-butyl-2-methyl-phenyl)oxamide (95.7 mg, 0.251 mmol), [Cp*IrCl$_2$]$_2$ (200.0 mg, 0.502 mmol; calculated as Ir) and potassium carbonate (139.1 mg, 1.01 mmol), and then purged with nitrogen. After addition of acetonitrile (10 mL), the mixture was stirred at 60° C. for 4 hours. The resulting suspension was allowed to stand, followed by decantation to remove the liquid phase. The solid was washed three times with acetonitrile (5 mL). Then, degassed water (5 mL) was added to the solid, followed by stirring. After the suspension was filtered, the solid was washed with degassed water (5 mL) and then washed twice with acetonitrile (5 mL). The solid collected by filtration was dried under reduced pressure to obtain the titled compound (245 mg) as a yellow solid (yield: 89%).

$^1$H-NMR (500 MHz, CDCl$_3$): σ=7.78 (s, 2H), 7.1-7.0 (m, 4H), 2.27 (s, 6H), 1.31 (s, 18H), 1.29 (s, 30H);

$^{13}$C-NMR (126 MHz, CDCl$_3$): σ=170.91 (C), 148.42 (C), 144.11 (C), 131.37 (C), 128.85 (CH), 122.58 (CH), 122.04 (CH), 83.74 (C), 34.49 (C), 31.54 (CH$_3$), 19.65 (CH$_3$), 8.55 (CH$_3$);

HRMS (APCI (Pos.)): m/z calc'd for C$_{44}$H$_{60}$ClIr$_2$N$_2$O$_2$ [M-Cl]$^+$ 1069.3596; measured=1069.3585.

[Example 28] Synthesis of [Cp*$_2$Ir$_2$Cl$_2$(μ-N,N'-bis (2-methylphenyl)-oxamidato)] (Ir-3)

[Formula 78]

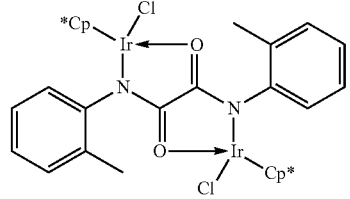

A 20 mL Schlenk tube was charged with N,N'-bis(2-methylphenyl)oxamide (67.6 mg, 0.252 mmol), [Cp*IrCl$_2$]$_2$ (200.0 mg, 0.502 mmol; calculated as Ir) and potassium carbonate (139.0 mg, 1.01 mmol), and then purged with nitrogen. After addition of acetonitrile (10 mL), the mixture was stirred at 60° C. for 4 hours. The resulting suspension was allowed to stand, followed by decantation to remove the liquid phase. The solid was washed twice with acetonitrile (5 mL). Then, degassed water (5 mL) was added to the solid, followed by stirring. After the suspension was filtered, the solid was washed with degassed water (5 mL) and then washed twice with acetonitrile (5 mL). The solid collected by filtration was dried under reduced pressure to obtain the titled compound (217 mg) as a yellow solid (yield: 87%).

$^1$H-NMR (500 MHz, CDCl$_3$): σ=7.72 (d, 2H, J=7.8 Hz), 7.15-7.10 (m, 4H), 7.07-7.02 (m, 2H), 2.31 (s, 6H), 1.30 (s, 30H);

$^{13}$C-NMR (126 MHz, CDCl$_3$): σ=170.86 (C), 144.52 (C), 134.68 (C), 129.32 (CH), 125.80 (CH), 125.46 (CH), 125.19 (CH), 83.88 (C), 20.12 (CH3), 8.48 (CH3);

HRMS (APCI): m/z calc'd for C$_{36}$H$_{44}$ClIr$_2$N$_2$O$_2$ [M-Cl]$^+$ 957.2344; measured 957.2338.

[Example 29] Synthesis of [Cp*$_2$Ir$_2$Cl$_2$(μ-N,N'-bis (3-methylphenyl)-oxamidato)] (Ir-4)

[Formula 79]

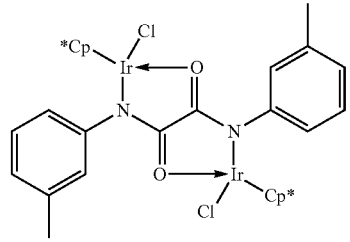

A 100 mL Schlenk tube was charged with N,N'-bis(3-methylphenyl)oxamide (336.7 mg, 1.25 mmol), [Cp*IrCl$_2$]$_2$ (1.00 g, 2.51 mmol; calculated as Ir) and potassium carbonate (695.0 mg, 5.02 mmol), and then purged with nitrogen. After addition of acetonitrile (50 mL), the mixture was stirred at 60° C. for 4 hours. The resulting suspension was allowed to stand, followed by decantation to remove the liquid phase. The solid was washed twice with acetonitrile (20 mL). Then, degassed water (20 mL) was added to the solid, followed by stirring. After the suspension was filtered, the solid was washed twice with degassed water (10 mL) and then washed twice with acetonitrile (5 mL). The solid was dried under reduced pressure to obtain the titled compound (1.00 g) as a yellow solid (yield: 81%).

$^1$H-NMR (500 MHz, CDCl$_3$): σ=7.45-7.40 (m, 4H), 7.20-7.10 (m, 2H), 6.91 (d, J=7.4 Hz, 2H), 2.34 (s, 6H), 1.34 (s, 30H);

$^{13}$C-NMR (126 MHz, CDCl$_3$): σ=171.89 (C), 145.38 (C), 137.38 (C), 127.49 (CH), 126.66 (CH), 125.74 (CH), 123.49 (CH), 83.98 (C), 21.43 (CH3), 8.56 (CH3);

HRMS (APCI): m/z calc'd for C$_{36}$H$_{44}$ClIr$_2$N$_2$O$_2$ [M-Cl]$^+$ 957.2344; measured 957.2330.

[Example 30] Synthesis of [Cp*$_2$Ir$_2$Cl$_2$(μ-N,N'-bis(2,3-dimethylphenyl)-oxamidato)] (Ir-5)

[Formula 80]

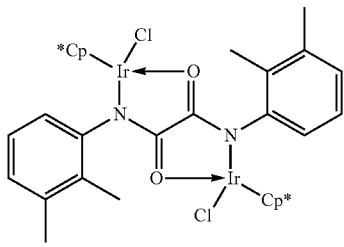

A 20 mL Schlenk tube was charged with N,N'-bis(2,3-dimethylphenyl)-oxamide (74.4 mg, 0.251 mmol), [Cp*IrCl$_2$]$_2$ (200.3 mg, 0.503 mmol; calculated as Ir) and potassium carbonate (138.4 mg, 1.00 mmol), and then purged with nitrogen. After addition of acetonitrile (10 mL), the mixture was stirred at 60° C. for 4 hours. The resulting suspension was allowed to stand, followed by decantation to remove the liquid phase. The solid was washed three times with acetonitrile (5 mL). Then, degassed water (5 mL) was added to the solid, followed by stirring. After the suspension was filtered, the solid was washed with degassed water (5 mL) and then washed twice with acetonitrile (5 mL). The solid collected by filtration was dried under reduced pressure to obtain the titled compound (236 mg) as a yellow solid (yield: 92%).

$^1$H-NMR (500 MHz, CDCl$_3$): σ=7.59 (d, 2H, 7.7 Hz), 7.02 (dd, 2H, J=7.7, 7.7 Hz), 6.94 (d, 2H, J=7.7 Hz), 2.31 (s, 6H), 2.17 (s, 6H), 1.29 (s, 30H);

$^{13}$C-NMR (126 MHz, CDCl$_3$): σ=171.07 (C), 144.50 (C), 135.97 (C), 133.03 (C), 126.59 (CH), 124.82 (CH), 123.42 (CH), 83.80 (C), 20.66 (CH3), 16.35 (CH3), 8.48 (CH3);

HRMS (APPI (Direct)): m/z calc'd for C$_{38}$H$_{48}$Cl$_2$Ir$_2$N$_2$O$_2$ [M]$^+$ 1020.2346; measured 1020.2334.

[Example 31] Synthesis of [Cp*$_2$Ir$_2$Cl$_2$(μ-N,N'-bis(2,4-dimethylphenyl)-oxamidato)] (Ir-6)

[Formula 81]

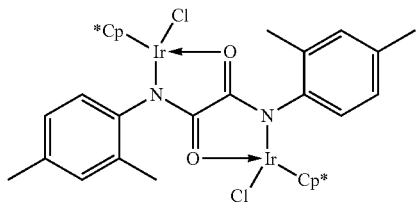

A 20 mL Schlenk tube was charged with N,N'-bis(2,4-dimethylphenyl)-oxamide (74.6 mg, 0.252 mmol), [Cp*IrCl$_2$]$_2$ (200.6 mg, 0.504 mmol; calculated as Ir) and potassium carbonate (139.0 mg, 1.01 mmol), and then purged with nitrogen. After addition of acetonitrile (10 mL), the mixture was stirred at 60° C. for 4 hours. The resulting suspension was allowed to stand, followed by decantation to remove the liquid phase. The solid was washed three times with acetonitrile (5 mL). Then, degassed water (5 mL) was added to the solid, followed by stirring. After the suspension was filtered, the solid was washed with degassed water (5 mL) and then washed twice with acetonitrile (5 mL). The solid collected by filtration was dried under reduced pressure to obtain the titled compound (194 mg) as a yellow solid (yield: 75%).

$^1$H-NMR (500 MHz, CDCl$_3$): σ=7.57 (d, 2H, 8.0 Hz), 6.93 (s, 2H), 6.91 (d, 2H, 8.0 Hz), 2.31 (s, 6H), 2.26 (s, 6H), 1.30 (s, 30H);

$^{13}$C-NMR (126 MHz, CDCl$_3$): σ=170.88 (C), 141.91 (C), 134.40 (C), 134.26 (C), 129.90 (CH), 126.07 (CH), 125.56 (CH), 83.79 (C), 21.00 (CH3), 20.09 (CH3), 8.50 (CH3);

HRMS (APPI (Direct)): m/z calc'd for C$_{38}$H$_{48}$Cl$_2$Ir$_2$N$_2$O$_2$ [M]$^+$ 1020.2346; measured 1020.2330.

[Example 32] Synthesis of [Cp*$_2$Ir$_2$Cl$_2$(μ-N,N'-bis(2,5-dimethylphenyl)-oxamidato)] (Ir-7)

[Formula 82]

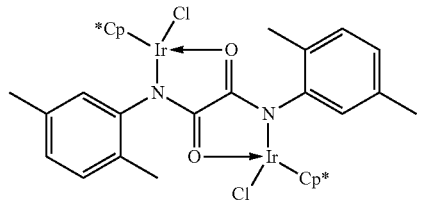

A 20 mL Schlenk tube was charged with N,N'-bis(2,5-dimethylphenyl)-oxamide (74.6 mg, 0.252 mmol), [Cp*IrCl$_2$]$_2$ (199.5 mg, 0.501 mmol; calculated as Ir) and potassium carbonate (138.7 mg, 1.00 mmol), and then purged with nitrogen. After addition of acetonitrile (10 mL), the mixture was stirred at 60° C. for 4 hours. The resulting suspension was allowed to stand, followed by decantation to remove the liquid phase. The solid was washed three times with acetonitrile (5 mL). Then, degassed water (5 mL) was added to the solid, followed by stirring. After the suspension was filtered, the solid was washed with degassed water (5 mL) and then washed twice with acetonitrile (5 mL). The solid collected by filtration was dried under reduced pressure to obtain the titled compound (222 mg) as a yellow solid (yield: 87%).

$^1$H-NMR (500 MHz, CDCl$_3$): σ=7.53 (s, 2H), 7.01 (d, 2H, J=7.6 Hz), 6.85 (d, 7.6 Hz), 2.29 (s, 6H), 2.26 (s, 6H), 1.29 (s, 30H);

$^{13}$C-NMR (126 MHz, CDCl$_3$): σ=170.80 (C), 144.31 (C), 134.73 (C), 131.63 (C), 129.11 (CH), 126.34 (CH), 125.93 (CH), 83.84 (C), 20.92 (CH3), 19.82 (CH3), 8.45 (CH3);

HRMS (APPI (Direct)): m/z calc'd for C$_{38}$H$_{48}$Cl$_2$Ir$_2$N$_2$O$_2$ [M]$^+$ 1020.2346; measured 1020.2340.

[Example 33] Synthesis of [Cp*$_2$Ir$_2$Cl$_2$(μ-N,N'-bis(2-ethylphenyl)oxamidato)](Ir-8)

[Formula 83]

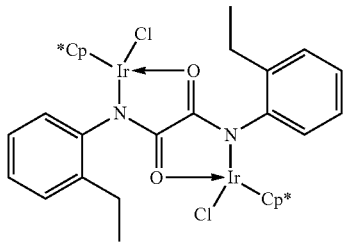

A 20 mL Schlenk tube was charged with N,N'-bis(2-ethylphenyl)oxamide (75.0 mg, 0.253 mmol), [Cp*IrCl$_2$]$_2$ (200.7 mg, 0.504 mmol; calculated as Ir) and potassium carbonate (139.2 mg, 1.01 mmol), and then purged with nitrogen. After addition of acetonitrile (10 mL), the mixture was stirred at 60° C. for 4 hours. The resulting suspension was allowed to stand, followed by decantation to remove the liquid phase. The solid was washed three times with acetonitrile (5 mL). Then, degassed water (5 mL) was added to the solid, followed by stirring. After the suspension was filtered, the solid was washed with degassed water (5 mL) and then washed twice with acetonitrile (5 mL). The solid was dried under reduced pressure to obtain the titled compound (237 mg) as a yellow solid (yield: 92%).

$^1$H-NMR (500 MHz, CDCl$_3$): σ=7.70-7.80 (m, 2H), 7.25-7.20 (m, 2H), 7.15-6.95 (m, 4H), 2.84 (qd, 2H, J=7.5, 15.0 Hz), 2.46 (qd, 2H, J=7.5 Hz, 15.0 Hz), 1.35-1.20 (m, 36H);

$^{13}$C-NMR (126 MHz, CDCl$_3$): σ=171.45 (C), 143.87 (C), 139.75 (C), 127.22 (CH), 125.91 (CH), 125.37 (CH), 125.30 (CH), 83.78 (C), 24.12 (CH2), 14.31 (CH3), 8.45 (CH3);

HRMS (APCI): m/z calc'd for C$_{38}$H$_{48}$ClIr$_2$N$_2$O$_2$ [M-Cl]$^+$ 985.2657; measured 985.2646.

[Example 34] Synthesis of [Cp*$_2$Ir$_2$Cl$_2$(μ-N,N'-bis(5-isopropyl-2-methyl-phenyl)oxamidato)] (Ir-9)

[Formula 84]

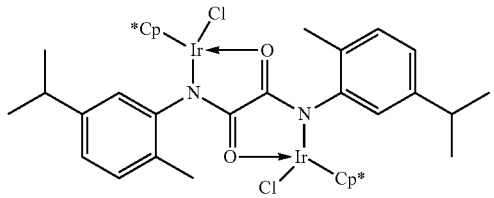

A 20 mL Schlenk tube was charged with N,N'-bis(5-isopropyl-2-methyl-phenyl)oxamide (88.6 mg, 0.251 mmol), [Cp*IrCl$_2$]$_2$ (199.7 mg, 0.501 mmol; calculated as Ir) and potassium carbonate (138.5 mg, 1.00 mmol), and then purged with nitrogen. After addition of acetonitrile (10 mL), the mixture was stirred at 60° C. for 4 hours. The resulting suspension was allowed to stand, followed by decantation to remove the liquid phase. The solid was washed three times with acetonitrile (5 mL). Then, degassed water (5 mL) was added to the solid, followed by stirring. After the suspension was filtered, the solid was washed with degassed water (5 mL) and then washed twice with acetonitrile (5 mL). The solid collected by filtration was dried under reduced pressure to obtain the titled compound (241 mg) as a yellow solid (yield: 89%).

$^1$H-NMR (500 MHz, CDCl$_3$): σ=7.58 (d, J=1.9 Hz, 2H), 7.05 (d, J=7.8 Hz, 2H), 6.92 (dd, J=1.9, 7.8 Hz, 2H), 2.87 (sept, J=6.9 Hz, 2H), 2.27 (s, 6H), 1.29 (s, 30H), 1.25 (d, J=6.9 Hz, 6H), 1.23 (d, J=6.9 Hz, 6H);

$^{13}$C-NMR (126 MHz, CDCl$_3$): σ=170.88 (C), 146.05 (C), 144.28 (C), 131.83 (C), 129.16 (CH), 123.73 (CH), 123.04 (CH), 83.79 (C), 33.69 (CH), 24.21 (CH3), 24.02 (CH3), 19.75 (CH3), 8.52 (CH3);

HRMS (APCI pos): m/z calc'd for C$_{42}$H$_{56}$ClIr$_2$N$_2$O$_2$ [M-Cl]$^+$ 1041.3283; measured 1041.3293.

[Example 35] Synthesis of [Cp*$_2$Ir$_2$Cl$_2$(μ-N,N'-bis(5-(adamantan-1-yl)-2-methylphenyl)oxamidato)] (Ir-10)

[Formula 85]

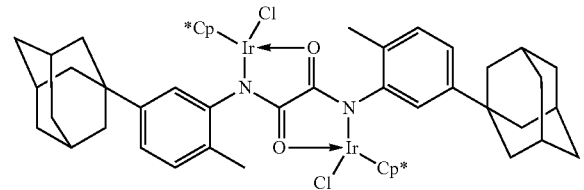

A 50 mL Schlenk tube was charged with N,N'-bis(5-(adamantan-1-yl)-2-methylphenyl)oxamide (135.7 mg, 0.253 mmol), [Cp*IrCl$_2$]$_2$ (401.7 mg, 1.01 mmol; calculated as Ir) and potassium carbonate (141.7 mg, 1.03 mmol), and then purged with nitrogen. After addition of acetonitrile (20 mL), the mixture was stirred at 60° C. for 6 hours. The resulting suspension was allowed to stand, followed by decantation to remove the liquid phase. The solid was washed five times with acetonitrile (5 mL). Then, degassed water (5 mL) was added to the solid, followed by stirring. After the suspension was filtered, the solid was washed with degassed water (5 mL) and then washed twice with acetonitrile (5 mL). The solid was dried under reduced pressure to obtain the titled compound (160 mg) as a yellow solid (yield: 50%).

$^{13}$C-NMR (126 MHz, CDCl$_3$): σ=170.80 (C), 148.79 (C), 144.18 (C), 131.41 (C), 128.82 (CH), 122.14 (CH), 121.56 (CH), 83.74 (C), 43.29 (CH2), 36.86 (CH2), 36.00 (C), 29.02 (CH), 19.65 (CH3), 8.58 (CH3);

HRMS (APPI pos): m/z calc'd for C$_{56}$H$_{72}$ClIr$_2$N$_2$O$_2$ [M-Cl]$^+$ 1225.4535; measured 1225.4520.

[Example 36] Synthesis of [(mesitylene)$_2$Ru$_2$Cl$_2$(μ-N,N'-bis(5-isopropyl-2-methylphenyl)oxamidato)] (Ru-1)

[Formula 86]

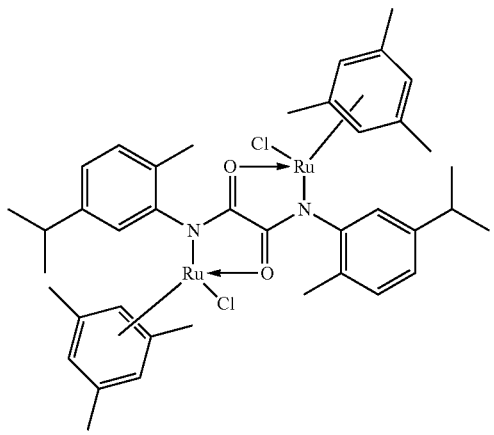

A 20 mL Schlenk tube was charged with N,N'-bis(5-isopropyl-2-methyl-phenyl)oxamide (120.2 mg, 0.341 mmol), [(mesitylene)RuCl$_2$]$_2$ (200.0 mg, 0.685 mmol; calculated as Ru) and potassium carbonate (190.4 mg, 1.38 mmol), and then purged with nitrogen. After addition of acetonitrile (10 mL), the mixture was stirred at 60° C. for 7 hours. The resulting suspension was allowed to stand, followed by decantation to remove the liquid phase. The solid was washed twice with acetonitrile (5 mL). Then, degassed water (5 mL) was added to the solid, followed by stirring. After the suspension was filtered, the solid was washed with degassed water (5 mL) and then washed twice with acetonitrile (5 mL). The solid collected by filtration was dried under reduced pressure to obtain the titled compound (248 mg) as a yellow solid (yield: 84%).

$^1$H-NMR (500 MHz, CDCl$_3$): 7.70 (d, J=1.6 Hz, 2H), 7.07 (d, J=7.8 Hz, 2H), 6.95 (dd, J=1.6 Hz, 7.8 Hz), 4.62 (s, 6H), 2.91 (sept, J=6.9 Hz, 2H), 2.28 (s, 6H), 1.79 (s, 18H), 1.30-1.25 (m, 12H);

$^{13}$C-NMR (126 MHz, CDCl$_3$): 168.45 (C), 146.38 (C), 146.01 (C), 132.00 (C), 129.32 (CH), 123.72 (CH), 123.09 (CH), 98.77 (CH), 33.67 (CH), 24.48 (CH3), 23.99 (CH3), 20.07 (CH3), 17.84 (CH3);

HRMS (APPI pos): m/z calc'd for C$_{40}$H$_{50}$Cl$_2$N$_2$O$_4$Ru$_2$ [M]$^+$ 864.1331; measured 864.1358.

[Example 37] Synthesis of [(p-cymene)$_2$Ru$_2$Cl$_2$(μ-N,N'-bis(5-isopropyl-2-methylphenyl)oxamidato)] (Ru-2)

[Formula 87]

A 20 mL Schlenk tube was charged with N,N'-bis(5-isopropyl-2-methyl-phenyl)oxamide (115.1 mg, 0.326 mmol), [(p-cymene)RuCl$_2$]$_2$ (199.6 mg, 0.652 mmol; calculated as Ru) and potassium carbonate (179.5 mg, 1.30 mmol), and then purged with nitrogen. After addition of acetonitrile (10 mL), the mixture was stirred at 60° C. for 7 hours. The resulting suspension was allowed to stand, followed by decantation to remove the liquid phase. The solid was washed twice with acetonitrile (5 mL). Then, degassed water (5 mL) was added to the solid, followed by stirring. After the suspension was filtered, the solid was washed with degassed water (5 mL) and then washed twice with acetonitrile (5 mL). The solid collected by filtration was dried under reduced pressure to obtain the titled compound (151 mg) as a yellow solid (yield: 52%).

$^1$H-NMR (500 MHz, CDCl$_3$): 7.45-7.35 (m, 2H), 7.13 (d, J=7.8 Hz, 2H), 6.98 (dd, J=1.9, 7.8 Hz, 2H), 5.20 (d, J=5.9 Hz, 2H), 5.13 (d, J=5.6 Hz, 2H), 5.07 (d, J=5.9 Hz, 2H), 4.61 (d, J=5.6 Hz, 2H), 2.88 (sept, J=6.9 Hz, 2H), 2.40 (sept, J=6.9 Hz, 2H), 2.31 (s, 6H), 1.74 (s, 6H), 1.25-1.20 (m, 12H), 1.12 (d, J=6.9 Hz, 6H), 1.02 (d, J=6.9 Hz, 6H);

$^{13}$C-NMR (126 MHz, CDCl$_3$): 168.45 (C), 147.25 (C), 146.63 (C), 130.12 (C), 129.68 (CH), 123.51 (CH), 122.77 (CH), 102.34 (C), 91.13 (C), 84.23 (CH), 82.26 (CH), 79.41 (CH), 77.91 (CH), 33.70 (CH3), 30.61 (CH3), 24.23 (CH3), 24.01 (CH3), 22.00 (CH3), 21.90 (CH3), 18.85 (CH3), 17.57 (CH3);

HRMS (APPI pos): m/z calc'd for C$_{42}$H$_{54}$Cl$_2$N$_2$O$_2$Ru$_2$ [M]$^+$ 892.1644; measured 892.1663.

[Example 38] Synthesis of Hexadecane-2,15-dione (Ir-2 to Ir-10)

[Formula 88]

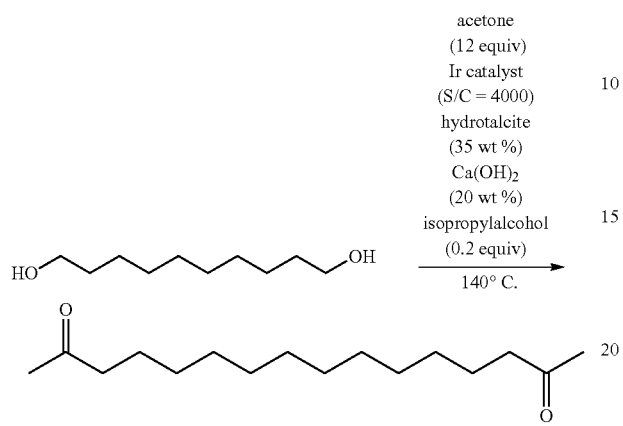

A 100 mL autoclave containing a magnetic stirrer was charged with decane-1,10-diol (5.00 g, 28.7 mmol), hydrotalcite (1.75 g, 35% by mass), calcium hydroxide (1.00 g, 20% by mass) and an Ir catalyst (S/C=4000), and then purged with nitrogen. Acetone (25 mL, 12 equivalents) and isopropyl alcohol (0.44 mL, 0.2 equivalents) were introduced into the autoclave, followed by initiation of heating and stirring. After stirring at 140° C. for 17 to 18 hours in total across 2 days, the autoclave was cooled. The hydrotalcite and calcium hydroxide were removed by filtration, and the filtrate was analyzed by gas chromatography. The results obtained are shown in Table 2. The results shown in Table 2 indicate that the catalytic activity is particularly high and the desired compound is obtained in high yield when using metal complexes having a methyl group at the 2-position.

It should be noted that, for example, the stirring time expressed as 7+10 hours means that stirring was conducted at a preset temperature across 2 days for 7 and 10 hours, respectively, i.e., for 17 hours in total.

TABLE 2

| Ir catalyst | Stirring time (hour) | GC area % | | | Quantitative yield (%) Hexadecane-2,15-dione |
| --- | --- | --- | --- | --- | --- |
| | | Decane-1,10-diol | 13-Hydroxy-tridecan-2-one | Hexa-decane-2,15-dione | |
| Ir-2 | 7 + 10 | 0 | 0 | 82 | 77 |
| Ir-3 | 9 + 9 | 0 | 4 | 70 | 50 |
| Ir-4 | 8 + 10 | 0 | 22 | 38 | 24 |
| Ir-5 | 8 + 9 | 0 | 5 | 65 | 42 |
| Ir-6 | 8 + 10 | 0 | 3 | 78 | 61 |
| Ir-7 | 7 + 11 | 0 | 2 | 80 | 65 |
| Ir-8 | 9 + 9 | 0 | 20 | 41 | 23 |
| Ir-9 | 8 + 10 | 0 | 0 | 82 | 73 |
| Ir-10 | 8 + 10 | 0 | 0 | 84 | 78 |
| Reference Example 1 | 8 + 10 | 0 | 21 | 43 | 27 |
| Reference Example 2 | 8 + 10 | 0 | 29 | 26 | 15 |

[Example 39] Synthesis of Hexadecane-2,15-dione (Reaction Time: Consecutive 24 Hours)

A 100 mL autoclave containing a magnetic stirrer was charged with decane-1,10-diol (5.00 g, 28.7 mmol), hydrotalcite (1.75 g, 35% by mass), calcium hydroxide (1.00 g, 20% by mass) and Ir-2 (4.1 mg, S/C=4000), and then purged with nitrogen. Acetone (25 mL, 12 equivalents) and isopropyl alcohol (0.44 mL, 0.2 equivalents) were introduced into the autoclave, followed by initiation of heating and stirring. After stirring at 120° C. for 24 hours, the autoclave was cooled. The hydrotalcite and calcium hydroxide were removed by filtration, and the filtrate was analyzed by gas chromatography, indicating that the quantitative yield of hexadecane-2,15-dione was 87%.

[Example 40] Synthesis of Hexadecane-2,15-dione (effect of N,N'-diphenyloxamide Addition)

A 100 mL autoclave containing a magnetic stirrer was charged with decane-1,10-diol (5.00 g, 28.7 mmol), hydrotalcite (1.75 g, 35% by mass), calcium hydroxide (1.00 g, 20% by mass), Ir-2 and N,N'-diphenyloxamide, and then purged with nitrogen. Acetone (25 mL, 12 equivalents) and isopropyl alcohol (0.44 mL, 0.2 equivalents) were introduced into the autoclave, followed by initiation of heating and stirring. After stirring at 120° C., the autoclave was cooled. The hydrotalcite and calcium hydroxide were removed by filtration, and the filtrate was analyzed by gas chromatography. The results obtained are shown in Table 3.

TABLE 3

| S/C | N,N'-Diphenyloxamide (equivalent relative to Ir) | Stirring time (hour) | Quantitative yield (%) Hexadecane-2,15-dione |
| --- | --- | --- | --- |
| 6000 | None | 9 + 9 | 70 |
| 6000 | 35 | 9 + 9 | 80 |
| 9000 | 50 | 24 | 73 |
| 12,000 | 50 | 24 | 71 |

[Example 41] Synthesis of Hexadecane-2,15-dione ([Cp*IrCl$_2$]$_2$+N,N'-diphenyloxamide, S/C=3000)

A 1000 mL autoclave equipped with an anchor-shaped stirring paddle was charged with decane-1,10-diol (100.0 g, 578.8 mmol), hydrotalcite (35.0 g, 35% by mass), calcium hydroxide (20.00 g, 20% by mass), [Cp*IrCl$_2$]$_2$ (76.2 mg, S/C=3000) and N,N'-diphenyloxamide (1.61 g, 35 equivalents relative to Ir), and then purged with nitrogen. Acetone (505 mL, 12 equivalents) and isopropyl alcohol (8.8 mL, 0.2 equivalents) were introduced into the autoclave, followed by initiation of heating and stirring. After stirring for 24 hours at 120° C., the autoclave was cooled. The hydrotalcite and calcium hydroxide were removed by filtration, and the filtrate was analyzed by gas chromatography, indicating that the quantitative yield of hexadecane-2,15-dione was 77% and the pure content thereof was 112.0 g.

The reaction mixture was concentrated with an evaporator for crude distillation to obtain a crude product of hexadecane-2,15-dione (116.5 g). The crude product was analyzed by gas chromatography, indicating that its purity was 88% by mass and its pure content was 101.9 g (yield: 70%).

[Example 42] Synthesis of Hexadecane-2,15-dione (Ir-2, Hydrotalcite S/C=6000)

A 200 mL autoclave equipped with an anchor-shaped stirring paddle was charged with decane-1,10-diol (20.0 g, 114.8 mmol), hydrotalcite (7.0 g, 35% by mass), calcium hydroxide (4.00 g, 20% by mass), Ir-2 (10.6 mg, S/C=6000) and N,N'-diphenyloxamide (161 mg, 35 equivalents relative to Ir), and then purged with nitrogen. Acetone (101 mL, 12 equivalents) and isopropyl alcohol (1.8 mL, 0.2 equivalents) were introduced into the autoclave, followed by initiation of heating and stirring. After stirring for 15 hours (8 hours+7 hours) at 120° C., the autoclave was cooled. The hydrotalcite and calcium hydroxide were removed by filtration, and the filtrate was analyzed by gas chromatography, indicating that the quantitative yield of hexadecane-2,15-dione was 75%.

[Example 43] Synthesis of Hexadecane-2,15-dione (Ir-2, Magnesium Aluminometasilicate)

A 200 mL autoclave equipped with an anchor-shaped stirring paddle was charged with decane-1,10-diol (20.0 g, 114.8 mmol), magnesium aluminometasilicate (7.0 g, 35% by mass), calcium hydroxide (4.00 g, 20% by mass), Ir-2 (10.6 mg, S/C=6000) and N,N'-diphenyloxamide (161 mg, 35 equivalents relative to Ir), and then purged with nitrogen. Acetone (101 mL, 12 equivalents) and isopropyl alcohol (1.8 mL, 0.2 equivalents) were introduced into the autoclave, followed by initiation of heating and stirring. After stirring for 20 hours (7 hours+9 hours+4 hours) at 120° C., the autoclave was cooled. The magnesium aluminometasilicate and calcium hydroxide were removed by filtration, and the filtrate was analyzed by gas chromatography, indicating that the quantitative yield of hexadecane-2,15-dione was 74%.

[Example 44] Synthesis of Hexadecane-2,15-dione (Ir-2, Magnesium Aluminosilicate)

A 200 mL autoclave equipped with an anchor-shaped stirring paddle was charged with decane-1,10-diol (20.0 g, 114.8 mmol), magnesium aluminosilicate (7.0 g, 35% by mass), calcium hydroxide (4.00 g, 20% by mass), Ir-2 (10.6 mg, S/C=6000) and N,N'-diphenyloxamide (161 mg, 35 equivalents relative to Ir), and then purged with nitrogen. Acetone (101 mL, 12 equivalents) and isopropyl alcohol (1.8 mL, 0.2 equivalents) were introduced into the autoclave, followed by initiation of heating and stirring. After stirring for 15 hours (8 hours+7 hours) at 120° C., the autoclave was cooled. The magnesium aluminosilicate and calcium hydroxide were removed by filtration, and the filtrate was analyzed by gas chromatography, indicating that the quantitative yield of hexadecane-2,15-dione was 65%.

[Example 45] Synthesis of Hexadecane-2,15-dione (Calcium Hydroxide)

A 200 mL autoclave equipped with an anchor-shaped stirring paddle was charged with decane-1,10-diol (20.0 g, 114.8 mmol), calcium hydroxide (11.0 g, 55% by mass), [Cp*IrCl$_2$]$_2$ (15.2 mg, S/C=3000) and N,N'-diphenyloxamide (321 mg, 35 equivalents relative to Ir), and then purged with nitrogen. Acetone (101 mL, 12 equivalents) and isopropyl alcohol (1.8 mL, 0.2 equivalents) were introduced into the autoclave, followed by initiation of heating and stirring. After stirring for 15 hours (8 hours+7 hours) at 120° C., the autoclave was cooled. The calcium hydroxide was removed by filtration, and the filtrate was analyzed by gas chromatography, indicating that the quantitative yield of hexadecane-2,15-dione was 37%.

[Example 46] Synthesis of Octan-2-one

[Formula 89]

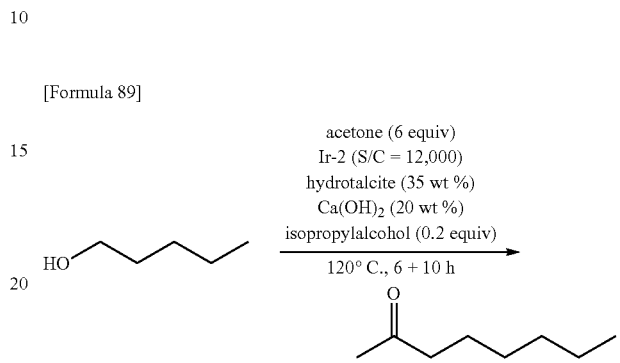

A 100 mL autoclave containing a magnetic stirrer was charged with hydrotalcite (1.75 g, 35% by mass), calcium hydroxide (1.00 g, 20% by mass) and Ir-2 (2.7 mg, S/C=12,000), and then purged with nitrogen. 1-Pentanol (5.00 g, 56.7 mmol), acetone (25 mL, 6 equivalents) and isopropyl alcohol (0.87 mL, 0.2 equivalents) were introduced into the autoclave, followed by initiation of heating and stirring. After stirring at 120° C. for 6+10 hours, the autoclave was cooled. The hydrotalcite and calcium hydroxide were removed by filtration, and the filtrate was analyzed by gas chromatography, indicating that the quantitative yield of octan-2-one was 80%.

[Example 47] Synthesis of Octan-2-one (Ruthenium Complex)

[Formula 90]

A 100 mL autoclave containing a magnetic stirrer was charged with magnesium aluminometasilicate (1.75 g, 70% by mass), calcium hydroxide (1.00 g, 40% by mass) and Ru-1 (12 mg, S/C=1000), and then purged with nitrogen. 1-Pentanol (2.5 g, 28.4 mmol), acetone (12.5 mL, 6 equivalents) and isopropyl alcohol (0.43 mL, 0.2 equivalents) were introduced into the autoclave, followed by initiation of heating and stirring. After stirring at 120° C., the autoclave was cooled. The solid base and calcium hydroxide were removed by filtration, and the filtrate was analyzed by gas chromatography. The results obtained are shown in Table 4.

TABLE 4

| Solid base | Stirring time (hour) | Quantitative yield (%) Octan-2-one |
|---|---|---|
| Hydrotalcite | 7 + 9 | 46 |
| Magnesium aluminometasilicate | 7 + 8 | 65 |

[Example 48] Synthesis of Nonan-3-one

[Formula 91]

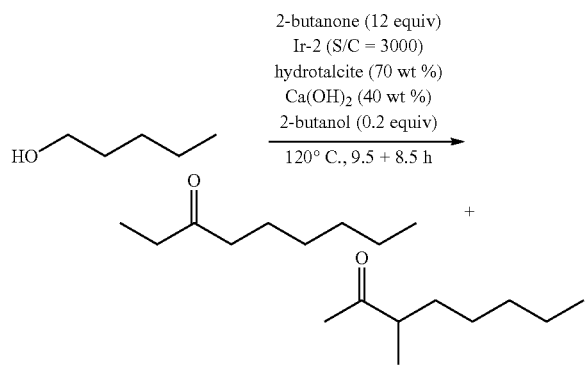

A 100 mL autoclave containing a magnetic stirrer was charged with hydrotalcite (1.75 g, 70% by mass), calcium hydroxide (1.00 g, 40% by mass) and Ir-2 (5.3 mg, S/C=3000), and then purged with nitrogen. 1-Pentanol (2.50 g, 28.4 mmol), 2-butanone (30.5 mL, 12 equivalents) and 2-butanol (0.52 mL, 0.2 equivalents) were introduced into the autoclave, followed by initiation of heating and stirring. After stirring at 120° C. for 9.5+8.5 hours, the autoclave was cooled. The hydrotalcite and calcium hydroxide were removed by filtration, and the filtrate was analyzed by gas chromatography, indicating that nonan-3-one (71%) and 3-methyloctan-2-one (25%) were produced (expressed in GC area %). It should be noted that the quantitative yield of nonan-3-one in this case was 67%.

[Example 49] Synthesis of Decan-4-one

[Formula 92]

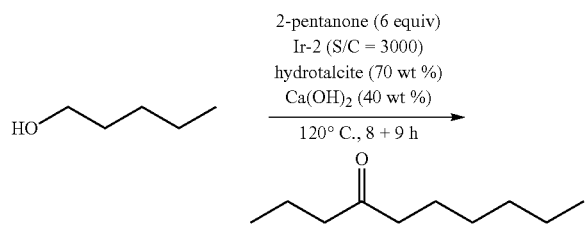

A 100 mL autoclave containing a magnetic stirrer was charged with hydrotalcite (1.75 g, 70% by mass), calcium hydroxide (1.00 g, 40% by mass) and Ir-2 (5.1 mg, S/C=3000), and then purged with nitrogen. 1-Pentanol (2.51 g, 28.5 mmol) and 2-pentanone (18.2 mL, 6 equivalents) were introduced into the autoclave, followed by initiation of heating and stirring. After stirring at 120° C. for 8+9 hours, the autoclave was cooled. The hydrotalcite and calcium hydroxide were removed by filtration, and the filtrate was analyzed by gas chromatography, indicating that decan-4-one was given in a quantitative yield of 93%.

[Example 50] Synthesis of 8-nonen-2-one

[Formula 93]

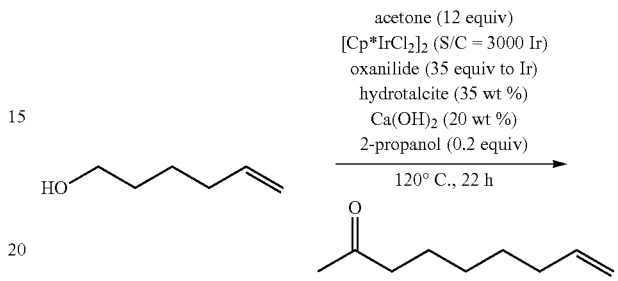

A 1000 mL mechanical autoclave was charged with [Cp*IrCl$_2$]$_2$ (76.2 mg, S/C=3000; calculated as Ir), N,N'-diphenyloxamide (1.61 g, 35 equivalents relative to Ir), hydrotalcite (20.1 g, 35% by mass) and Ca(OH)$_2$ (11.5 g, 20% by mass), and then purged with nitrogen. Through the inlet, 5-hexen-1-ol (57.5 g, 574 mmol), acetone (400 g, 12 equivalents) and isopropyl alcohol (6.9 g, 0.2 equivalents) were added under a nitrogen stream with a syringe, and the inlet was then closed. After stirring at 120° C. for 22 hours, the autoclave was cooled. The reaction mixture was analyzed by gas chromatography, indicating that 8-nonen-2-one was obtained in a quantitative yield of 87%.

INDUSTRIAL APPLICABILITY

The method of the present invention for converting a hydroxyl group of an alcohol enables the conversion of a hydroxyl group of a relatively inexpensive alcohol to thereby achieve the alkylation of a compound having an active proton, and is therefore useful in the production of valuable substances such as pharmaceutical compounds, flavors and fragrances.

The invention claimed is:

1. A method for converting a hydroxyl group of an alcohol, comprising reacting:
   in the presence of a metal complex of Groups 7 to 11 in the periodic table and at least one solid base selected from the group consisting of a layered double hydroxide, a composite oxide and calcium hydroxide;
   an alcohol represented by the following general formula (1):

[Formula 1]

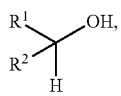

(1)

wherein:
   $R^1$ and $R^2$ are each independently a hydrogen atom, an optionally substituted alkyl group, an optionally substituted aryl group, an optionally substituted heterocyclyl group or an optionally substituted aralkyl group, where at least one of $R^1$ and $R^2$ may have a hydroxyl group as a substituent, and/or $R^1$ and $R^2$ may be joined together to form a ring; with a compound having an active proton represented by the following general formula (2):

[Formula 2]

$$H\text{-}Nu \quad (2),$$

wherein:
Nu is a group represented by $-CHX^1\text{-}EWG^1$ or $-NR^3R^4$, where $X^1$ is a hydrogen atom or a substituent, $EWG^1$ is an electron-withdrawing group, and $R^3$ and $R^4$ are each independently a hydrogen atom, an optionally substituted alkyl group, an optionally substituted aryl group, an optionally substituted heterocyclyl group or an optionally substituted aralkyl group, where $R^3$ and $R^4$ may be joined together to form a ring; or when $R^1$ in general formula (1) is attached to $X^1$ or $R^3$ in Nu in general formula (2) such that the alcohol and the compound having an active proton form a single molecule, the reaction occurs within the molecule;

to produce a compound represented by the following general formula (3):

[Formula 3]

$$\begin{array}{c} R^1 \\ R^2 \end{array}\!\!\!\!\!\!\diagdown\!\!\!\!\!\!\diagup\!\!\!\!\text{Nu}, \quad (3)$$
(with H)

wherein:
$R^1$, $R^2$ and Nu are as defined above, where $R^1$ and $X^1$ or $R^3$ in Nu may be joined together to form a ring, and wherein the solid base is (a) a layered double hydroxide or (b) a composite oxide comprising two or more metal elements, at least one of which is a metal element selected from the group consisting of aluminum, magnesium and calcium.

2. The method for converting a hydroxyl group of claim 1, wherein the solid base is a layered double hydroxide.

3. The method for converting a hydroxyl group of claim 2, wherein the layered double hydroxide is a hydrotalcite-type compound.

4. The method for converting a hydroxyl group of claim 1, wherein the solid base is a composite oxide comprising two or more metal elements, at least one of which is a metal element selected from the group consisting of aluminum, magnesium and calcium.

5. The method for converting a hydroxyl group of claim 1, wherein the compound having an active proton represented by general formula (2) is a carbonyl compound represented by the following general formula (2-1):

[Formula 4]

$$\underset{H}{\overset{H}{\diagdown}}\!C(X^1)\!-\!C(=O)\!-\!R^5, \quad (2\text{-}1)$$

wherein:
$X^1$ is as defined above, and
$R^5$ is a hydrogen atom, an optionally substituted alkyl group, an optionally substituted alkenyl group, an optionally substituted alkynyl group, an optionally substituted aryl group, an optionally substituted heterocyclyl group, an optionally substituted aralkyl group, an optionally substituted alkoxy group, an optionally substituted aryloxy group, an optionally substituted amino group or an optionally substituted carbonyl group,
where $X^1$ and $R^5$ may be joined together to form a ring.

6. The method for converting a hydroxyl group of claim 1, wherein the metal complex of Groups 7 to 11 in the periodic table is an iridium complex or a ruthenium complex.

7. The method for converting a hydroxyl group of claim 6, wherein the iridium complex is:
a compound represented by the following general formula (4-1) or a dimer thereof:

[Formula 5]

(4-1)

wherein:
$Y^1$ is an optionally substituted cyclopentadienyl group or an optionally substituted indenyl group,
$Z^1$ is a hydrido or anionic group,
$A^1$ is an optionally substituted aryl group, an optionally substituted heterocyclyl group or an optionally substituted carbonyl group, where $A^1$ may partially coordinate to the iridium atom,
$X^4$, $X^5$, $X^6$, $X^7$ and $X^8$ are each independently a hydrogen atom or a substituent,
where $X^4$ and $X^5$, $X^5$ and $X^6$, $X^6$ and $X^7$ as well as $X^7$ and $X^8$ may each be joined together to form a ring, and/or $Y^1$ and $A^1$ as well as $Y^1$ and $X^4$ may each be joined together to form a ring, and
m is 1 or 2, and n is 1 or 0, provided that n is 1 when m is 1, and n is 0 when m is 2; or
a compound represented by the following general formula (4-2):

[Formula 6]

(4-2)

wherein:

$Y^1$, $Z^1$, $X^4$, $X^5$, $X^6$, $X^7$ and $X^8$ are as defined above.

8. The method for converting a hydroxyl group of claim 6, wherein the iridium complex is formed within the reaction system by mixing an iridium compound represented by the following general formula (5-1) or a dimer thereof:

   (5-1), wherein:

$Y^1$ is an optionally substituted cyclopentadienyl group or an optionally substituted indenyl group, and $Z^1$ is a hydrido or anionic group; with an anilide represented by the following general formula (6-1):

[Formula 7]

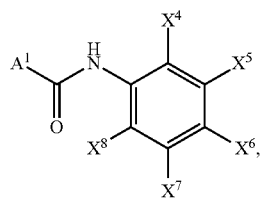   (6-1)

wherein:

$A^1$ is an optionally substituted aryl group, an optionally substituted heterocyclyl group or an optionally substituted carbonyl group, and $X^4$, $X^5$, $X^6$, $X^7$ and $X^8$ are each independently a hydrogen atom or a substituent, where $X^4$ and $X^5$, $X^5$ and $X^6$, $X^6$ and $X^7$ as well as $X^7$ and $X^8$ may each be joined together to form a ring; or with an anilide represented by the following general formula (6-2):

[Formula 8]

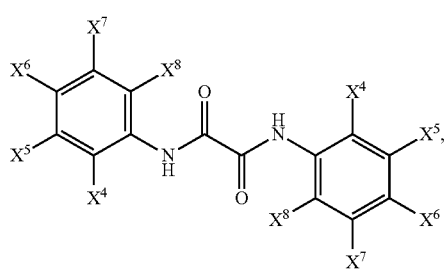   (6-2)

wherein:

$X^4$, $X^5$, $X^6$, $X^7$ and $X^8$ are as defined above.

9. The method for converting a hydroxyl group of claim 6, wherein the ruthenium complex is:

a compound represented by the following general formula (4-3) or a dimer thereof:

[Formula 9]

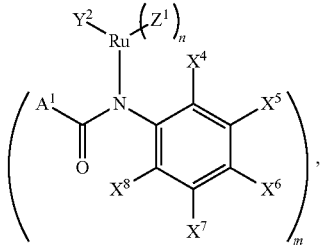   (4-3)

wherein:

$Y^2$ an optionally substituted arene, $Z^1$ is a hydrido or anionic group, $A^1$ is an optionally substituted aryl group, an optionally substituted heterocyclyl group or an optionally substituted carbonyl group, where $A^1$ may partially coordinate to the ruthenium atom, $X^4$, $X^5$, $X^6$, $X^7$ and $X^8$ are each independently a hydrogen atom or a substituent, where $X^4$ and $X^5$, $X^5$ and $X^6$, $X^6$ and $X^7$ as well as $X^7$ and $X^8$ may each be joined together to form a ring, and/or $Y^1$ and $A^1$ as well as $Y^1$ and $X^4$ may each be joined together to form a ring, and m is 1 or 2, and n is 1 or 0, provided that n is 1 when m is 1, and n is 0 when m is 2; or a compound represented by the following general formula (4-4):

[Formula 10]

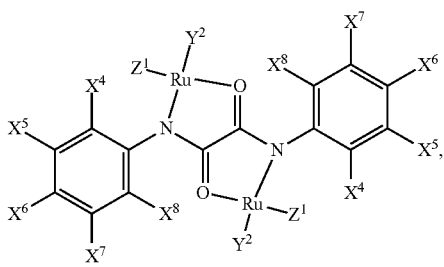   (4-4)

wherein:

$Y^2$, $Z^1$, $X^4$, $X^5$, $X^6$, $X^7$ and $X^8$ are as defined above.

10. The method for converting a hydroxyl group of claim 6, wherein the ruthenium complex is formed within the reaction system by mixing a ruthenium compound represented by the following general formula (5-3) or a dimer thereof:

$[Y^2RuZ^1{}_2]$   (5-3), wherein:

$Y^2$ is an optionally substituted arene, and $Z^1$ is a hydrido or anionic group; with an anilide represented by the following general formula (6-1):

[Formula 11]

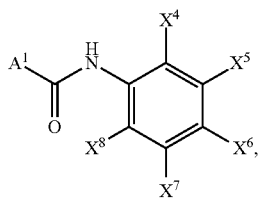
(6-1)

wherein:
A¹ is an optionally substituted aryl group, an optionally substituted heterocyclyl group or an optionally substituted carbonyl group, and
$X^4$, $X^5$, $X^6$, $X^7$ and $X^8$ are each independently a hydrogen atom or a substituent,
where $X^4$ and $X^5$, $X^5$ and $X^6$, $X^6$ and $X^7$ as well as $X^7$ and $X^8$ may each be joined together to form a ring;
or with
an anilide represented by the following general formula (6-2):

[Formula 12]

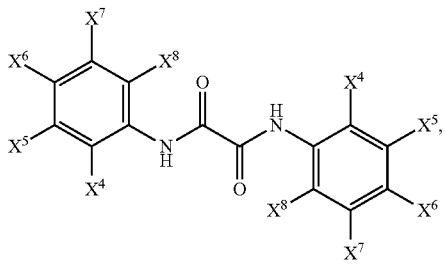
(6-2)

wherein:
$X^4$, $X^5$, $X^6$, $X^7$ and $X^8$ are as defined above.

11. The method for converting a hydroxyl group of claim 5, wherein the carbonyl compound represented by general formula (2-1) is acetone.

12. An iridium complex selected from the group consisting of:
a compound represented by the following general formula (4-1a) or a dimer thereof:

[Formula 13]

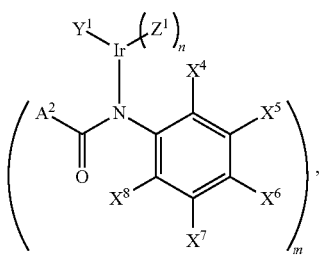
(4-1a)

wherein:
Y¹ is an optionally substituted cyclopentadienyl group or an optionally substituted indenyl group,
Z¹ is a hydrido or anionic group,
A² is an optionally substituted aryl group or an optionally substituted carbonyl group, where A² may partially coordinate to the iridium atom,
$X^4$, $X^5$, $X^6$, $X^7$ and $X^8$ are each independently a hydrogen atom or a substituent,
where $X^4$ and $X^5$, $X^5$ and $X^6$, $X^6$ and $X^7$ as well as $X^7$ and $X^8$ may each be joined together to form a ring, and/or Y¹ and A¹ as well as Y¹ and $X^4$ may each be joined together to form a ring, and
m is 1 or 2, and n is 1 or 0, provided that n is 1 when m is 1, and n is 0 when m is 2; and
a compound represented by the following general formula (4-2):

[Formula 14]

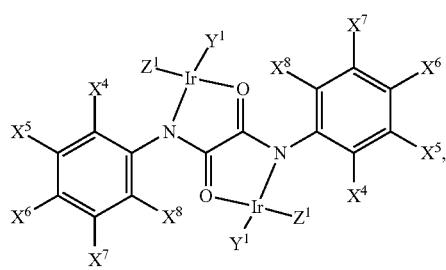
(4-2)

wherein:
Y¹, Z¹, $X^4$, $X^5$, $X^6$, $X^7$ and $X^8$ are as defined above,
except for the case where Y¹ is pentamethylcyclopentadienyl, Z¹ is a chlorine atom, $X^4$, $X^5$, $X^7$ and $X^8$ are each a hydrogen atom, and $X^6$ is a hydrogen atom or a methyl group and wherein in formula (4-2) at least one of $X^4$, $X^5$, $X^7$ and $X^8$ is a substituent selected from the group consisting of an alkyl group, an alkoxy group, a halogeno group and an optionally protected amino group.

13. The iridium complex of claim 12, which is a catalyst for use in the reaction of converting a hydroxyl group of an alcohol.

14. A ruthenium complex selected from the group consisting of:
a compound represented by the following general formula (4-3) or a dimer thereof:

[Formula 15]

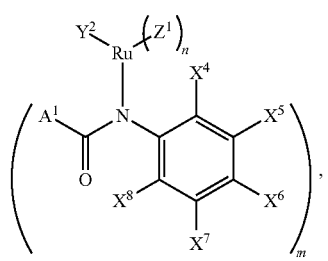
(4-3)

wherein:
Y² is an optionally substituted arene,
Z¹ is a hydrido or anionic group,
A¹ is an optionally substituted aryl group, an optionally substituted heterocyclyl group or an optionally substituted carbonyl group, where A¹ may partially coordinate to the ruthenium atom, $X^4$, $X^5$, $X^6$, $X^7$ and $X^8$ are each independently a hydrogen atom or a substituent,
where $X^4$ and $X^5$, $X^5$ and $X^6$, $X^6$ and $X^7$ as well as $X^7$ and $X^8$ may each be joined together to form a ring, and/or $Y^1$ and $A^1$ as well as $Y^1$ and $X^4$ may each be joined together to form a ring, and
m is 1 or 2, and n is 1 or 0, provided that n is 1 when m is 1, and n is 0 when m is 2; or
a compound represented by the following general formula (4-4):

[Formula 16]

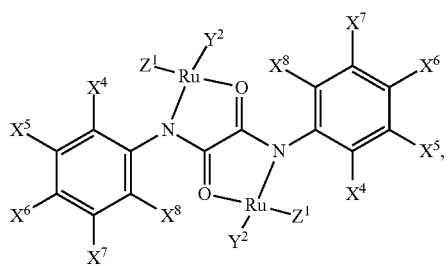

(4-4)

wherein:
$Y^2$, $Z^1$, $X^4$, $X^5$, $X^6$, $X^7$ and $X^8$ are as defined above and wherein in formula (4-4) at least one of $X^4$, $X^5$, $X^7$ and $X^8$ is a substituent selected from the group consisting of an alkyl group, an alkoxy group, a halogeno group and an optionally protected amino group.

15. The ruthenium complex of claim 14, which is a catalyst for use in the reaction of converting a hydroxyl group of an alcohol.

16. The iridium complex of claim 12, which is the compound of the general formula (4-1a).

17. The iridium complex of claim 12, which is the compound of the general formula (4-2).

18. The ruthenium complex of claim 14, which is the compound of the general formula (4-3).

19. The ruthenium complex of claim 14, which is the compound of the general formula (4-4).

* * * * *

UNITED STATES PATENT AND TRADEMARK OFFICE
CERTIFICATE OF CORRECTION

| | | |
|---|---|---|
| PATENT NO. | : 11,407,703 B2 | Page 1 of 1 |
| APPLICATION NO. | : 17/051261 | |
| DATED | : August 9, 2022 | |
| INVENTOR(S) | : Shimizu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 21 days.

Signed and Sealed this
Twentieth Day of May, 2025

Coke Morgan Stewart
*Acting Director of the United States Patent and Trademark Office*